United States Patent [19]
Sheffield et al.

[11] Patent Number: 6,087,107
[45] Date of Patent: Jul. 11, 2000

[54] THERAPEUTICS AND DIAGNOSTICS FOR CONGENITAL HEART DISEASE BASED ON A NOVEL HUMAN TRANSCRIPTION FACTOR

[75] Inventors: Val C. Sheffield, Coralville; Wallace L. M. Alward; Edwin M. Stone, both of Iowa City; Darryl Nishimura, Coralville; Shiva Patil, Iowa City, all of Iowa

[73] Assignee: The University of Iowa Research Foundation, Iowa City, Iowa

[21] Appl. No.: 09/083,351

[22] Filed: May 22, 1998

Related U.S. Application Data

[60] Provisional application No. 60/081,870, Apr. 15, 1998.

[51] Int. Cl.$^7$ .............................. C07H 21/04; C12Q 1/68; G01N 33/53
[52] U.S. Cl. ............................ 435/6; 435/7.1; 536/24.31; 536/24.33
[58] Field of Search ........................ 435/6, 7.1; 536/24.3, 536/24.31, 24.33

[56] References Cited

FOREIGN PATENT DOCUMENTS

WO 99/16899   8/1999   WIPO .

OTHER PUBLICATIONS

Stone, E.M., et al., Identification of a gene that causes primary open angle glaucoma. Science 275, 668–670 (1997).

Stoilov, I., et al., Identification of three different truncating mutations in cytochrome P4501B1 (CYP1B) as the principal cause of primary congenital glaucoma (Buphthalmos) in families linked to the GLC3A locus on chromosome 2p21. Hum. Mol. Genet. 6, 641–647 (1997).

Semina, E.V. et al., Cloning and characterization of a novel bicoid–related homebox transcription factor gene, RIEG, involved in Rieger syndrome. Nat. Genet. 14, 392–399 (1996).

Alward, W.L.M. et al., Autosomal Dominant Iris Hypoplasia is Caused By a Mutation In the Rieger–Syndrome (Rieg/Pitx2) Gene. Am. J. Opthalmol. 125, 98–100 (1998).

Akarsu, A.N. et al., A second locus (GLC3B) for primary confenital glaucoma (Buphthalmos) maps to the 1p36 region. Hum. Mol. Genet. 5, 1199–1203 (1996).

Phillips, J.C. et al., A second locus for Rieger syndrome maps to chromosome 13q14. Am. J. Hu. Genet. 59, 613–619 (1996).

Stoilova, D. et al., Localization of a locus (GLCIB) for adult–onset primary open angle glaucoma to the 2cen–q13 region. Genomics 36, 142–150 (1996).

Wirtz, M.K. et al., Mapping a gene for adult–onset primary open–angle glaucoma to chromosome 3q. Am. J. Hum. Genet. 60, 296–304 (1997).

Mears, A.J., et al., Autosomal dominant iridogoniodysgenesis anomaly maps to 6p25. Am. J. Hum. Genet. 59, 1321–1327 (1996).

Gould, D.B. et al., Autosomal dominant Axenfeld–Rieger anomaly maps to 6p25 [letter], Am. J. Hum. Genet. 61, 765–768 (1997).

Jordan, T. et al., Familial glaucoma iridogoniodysplasia maps to a 6p25 region implicated in primary congenital glaucoma and iridogoniodysgenesis anomaly, Am. J. Hum. Genet. 61, 882–888 (1997).

Graff, C., et al., Fine Mapping of the Gene for Autosomal Dominant Juvenile–Onset Glaucoma with Iridogoniodysgenesis in 6p25–Tel. Hum. Genet. 101, 130–134 (1997).

Murray, J.C. et al., A Comprehensive Human Linkage Map with Centimorgan Density. Cooperative Human Linkage Center (CHLC) Science 265, 2049–2054 (1994).

Dorin, J.R. et al., Gene Targeting for Somatic Cell Manipulation: Rapid Analysis of Reduced Chromosome Hybrids by Alu–PCR Fingerprinting and Chronosome Painting. Hum. Mol. Genet. 1, 53–59 (1992).

Li, Y. et al., Analysis of 43 kb of the Chlorella virus PBCV–1 330–kb genome: Map Positions 45 to 88. Virology 212, 134–150 (1995).

Stevenson, G. et al., Organization of the Escherichia coli K–12 Gene Cluster Responsible for Production of the Extracellular Polysaccharide Colanic Acid. J. Bacteriol. 178, 4885–4893 (1996).

Bonin, C.P. et al., The MUR1 Gene of Arabidopsis Thaliana Encodes an Isoform of GDP–D–mannose–4, 6–dehydratase, Catalyzing the First Step in the De Novo Synthesis of GDP–L–fucose. Proc. Natl. Acad. Sci. USA 94, 2085–2090 (1997).

Glaser, T. et al., Genomic Structure, Evolutionary Conservation and Aniridia Mutations in the Human PAX6 Gene. Nat. Genet. 2, 232–239 (1992).

Jordan, T. et al., The Human PAX6 Gene is Mutated in Two Patients with Aniridia. Nat. Genet. 1, 328–332 (1992).

Attree, O. et al., The Lowe's Oculocerebrorenal Syndrome Gene Encodes a Protein Highly Homologous to Inositol Polyphosphate–5–Phosphatase. Nature 358, 239–242 (1992).

Fantes, J. et al., Aniridia–associated Cytogenetic Rearrangements Suggest That a Position Effect May Cause the Mutant Phenotype. Hum. Mol. Genet. 4, 415–422 (1995).

Galili, N. et al., Fusion of a Fork Head Domain Gene to PAX3 in the Solid Tumour Alveolar Rhabdomyosarcoma. Nat. Genet. 5, 230–235 (1993).

Clark, K.L., et al., Co–crystal Structure of the HNF–3/fork head DNA–recognition Motif Resembles Histone H5. Nature 364, 412–4420 (1993).

Pierrou,S. et al., Cloning and Characterization of Seven Human Forkhead Proteins: Binding Site Specificity and DNA Bending. EMBO Journal 13, 5002–5012 (1994).

(List continued on next page.)

Primary Examiner—Robert A. Schwartzman
Attorney, Agent, or Firm—Foley, Hoag & Eliot, LLP; Beth E. Arnold, Esq.

[57] ABSTRACT

Methods and compositions for treating a congenital heart disease and methods and compositions for prognosing or diagnosing a congenital heart disease in a subject are disclosed.

18 Claims, 4 Drawing Sheets

OTHER PUBLICATIONS

Larsson, C., et al., Chromosomal Localization of Six Human Forkhead Genes, freac–1 (FKHL5), –3 (FKHL7), –4 (FKHL8) –5 (FKHL9) –6 (FKHL10) and –8 (FKHL12). Genomics 30, 464–469 (1995).

Darryl Y. Nishimura, et al., The Forkhead Transcription Factor Gene FKHL7 is Responsible For Glaucoma Phenotypes which Map to 6p25. Nature Genet. 19 140–147 (1998).

Vitovski, S., et al., Invasive Isolates of Neisseria Meningitidis Possess Enhanced Immunoglobulin A1 Protease Activity Compared to Colonizing Strains, FASEB J. 13, 331–337 (1999).

Meyer, T.F., et al., Mechanism of Extracellular Secretion of an IgA Protease by Gram–Negavtive Host Cells, Adv. Exp. Med. Biol. 216B: 1271–1281 (1987).

Wallace L. M. Alward, et al., Molecular Genetics of Glaucoma: Current Status, (1996) J. Glaucoma 5, 276–284.

Ying Xu, et al., Recognizing Exons in Genomic Sequence Using Grail II, (1994) Gen. Engin. 16, 241–253.

Database EMBLhum#: SEQ ID: HSMFH1 AC: Y08223 H. sapiens MFH–1 gene., Mar. 1997, pp. XP002122926.

Database EMBLest20, SEQ ID:HS1223780 AN: AA42466 H. sapiens cDNA clone 767110 3', May 1997, XP002122927.

Nishimura et al., "The forkhead transcription factor gene FKHL7 is responsible for glaucoma phenotypes which map to 6p25", Nat. Gen., vol. 19, no. 2, Jun. 1998, pp. 140–147, XP002095717.

Mears, A.J. et al., Mutations of the forkhead/winged–helix gene, FKHL7, in patients with Am. J. of Hum. Gen., vol. 63, no. 5, Nov. 1998, pp.1316–1328, XP002095718.

```
  1  cgagaaaaggtgacgcggggcccgggcaggcggccggcgcgcggccccccccccccccgc
 61  cctggttatttggccgccttcgccggcagctcagggcagagtctcctggaaggcgcaggc
121  agtgtggcgagaagggcgcctgcttgttctttcttttgtctgctttccccgtttgcgc
181  ctggaagctgcgccgcgagttcctgcaaggcggtctgccgcggccgggcccggccttctc
241  ccctcgcagcgaccccgcctcgcggcgcgcgggccccgaggtagcccggagcgccggag
301  gagccagccccagcgagcgccgggagaggcggcagcgcagccggacgcacagcgcagcgg
361  gccggcaccagctcggccgggcccggactcggactcggcggccggcgcggcgcggcccgg
421  cccgagcgagggtggggggcggcgggcggcgcgggg
```

| | | |
|---|---|---|
| 457 | cggcggcgagcgggggccATGCAGGCGCGCTACTCCGTGTCCAGCCCCAACTCC<br>................METGlnAlaArgTyrSerValSerSerProAsnSer | 12 |
| 511 | CTGGGAGTGGTGCCCTACCTCGGCGGCGAGCAGAGCTACTACCGCGCGGCGGCC<br>LeuGlyValValProTyrLeuGlyGlyGluGlnSerTyrTyrArgAlaAlaAla | 30 |
| 565 | GCGGCGGCCGGGGGCGGCTACACCGCCATGCCGGCCCCCATGAGCGTGTACTCG<br>AlaAlaAlaGlyGlyGlyTyrThrAlaMETProAlaProMETSerValTyrSer | 48 |
| 619 | CACCCTGCGCACGCCGAGCAGTACCCGGGCGGCATGGCCCGCGCCTACGGGCCC<br>HisProAlaHisAlaGluGlnTyrProGlyGlyMETAlaArgAlaTyrGlyPro | 66 |
| 673 | TACACGCCGCAGCCGCAGCCCAAGGACATGGTGAAGCCGCCCTATAGCTACATC<br>TyrThrProGlnProGlnProLysAspMETValLysProProTyrSerTyrIle | 84 |
| 727 | GCGCTCATCACCATGGCCATCCAGAACGCCCCGGACAAGAAGATCACCCTGAAC<br>AlaLeuIleThrMETAlaIleGlnAsnAlaProAspLysLysIleThrLeuAsn | 102 |
| 781 | GGCATCTACCAGTTCATCATGGACCGCTTCCCCTTCTACCGGGACAACAAGCAG<br>GlyIleTyrGlnPheIleMETAspArgPheProPheTyrArgAspAsnLysGln | 120 |
| 835 | GGCTGGCAGAACAGCATCCGCCACAACCTCTCGCTCAACGAGTGCTTCGTCAAG<br>GlyTrpGlnAsnSerIleArgHisAsnLeuSerLeuAsnGluCysPheValLys | 138 |
| 889 | GTGCCGCGCGACGACAAGAAGCCGGGCAAGGGCAGCTACTGGACGCTGGACCCG<br>ValProArgAspAspLysLysProGlyLysGlySerTyrTrpThrLeuAspPro | 156 |
| 943 | GACTCCTACAACATGTTCGAGAACGGCAGCTTCCTGCGGCGGCGGCGGCGCTTC<br>AspSerTryAsnMETPheGluAsnGlySerPheLeuArgArgArgArgArgPhe | 174 |
| 997 | AAGAAGAAGGACGCGGTGAAGGACAAGGAGGAGAAGGACAGGCTGCACCTCAAG<br>LysLysLysAspAlaValLysAspLysGluGluLysAspArgLeuHisLeuLys | 192 |
| 1051 | GAGCCGCCCCCGCCCGGCCGCCAGCCCCCGCCCGCCGCCGGAGCAGGCCGAC<br>GluProProProProGlyArgGlnProProAlaProProGluGlnAlaAsp | 210 |
| 1105 | GGCAACGCGCCCGGTCCGCAGCCGCCGCCCGTGCGCATCCAGGACATCAAGACC<br>GlyAsnAlaProGlyProGlnProProValArgIleGlnAspIleLysThr | 228 |
| 1159 | GAGAACGGTACGTGCCCCTCGCCGCCCCAGCCCCTGTCCCCGGCCGCCGCCCTG<br>GluAsnGlyThrCysProSerProProGlnProLeuSerProAlaAlaAlaLeu | 246 |
| 1213 | GGCAGCGGCAGCGCCGCCGCGGTGCCCAAGATCGAGAGCCCCGACAGCAGCAGC<br>GlySerGlySerAlaAlaAlaValProLysIleGluSerProAspSerSerSer | 264 |
| 1267 | AGCAGCCTGTCCAGCGGGAGCAGCCCCCCGGGCAGCCTGCCGTCGGCGCGGCCG<br>SerSerLeuSerSerGlySerSerProProGlySerLeuProSerAlaArgPro | 282 |
| 1321 | CTCAGCCTGGACGGTGCGGATTCCGCGCCGCCGCCGCCCGCGCCCTCCGCCCCG<br>LeuSerLeuAspGlyAlaAspSerAlaProProProAlaProSerAlaPro | 300 |
| 1375 | CCGCCGCACCATAGCCAGGGCTTCAGCGTGGACAACATCATGACGTCGCTGCGG<br>ProProHisHisSerGlnGlyPheSerValAspAsnIleMETThrSerLeuArg | 318 |
| 1429 | GGGTCGCCGCAGAGCGCGGCCGCGGAGCTCAGCTCCGGCCTTCTGGCCTCGGCG<br>GlySerProGlnSerAlaAlaAlaGluLeuSerSerGlyLeuLeuAlaSerAla | 336 |
| 1483 | GCCGCGTCCTCGCGCGCGGGGATCGCACCCCCGCTGGCGCTCGGCGCCTACTCG<br>AlaAlaSerSerArgAlaGlyIleAlaProProLeuAlaLeuGlyAlaTyrSer | 354 |
| 1537 | CCCGGCCAGAGCTCCCTCTACAGCTCCCCCTGCAGCCAGACCTCCAGCGCGGGC<br>ProGlyGlnSerSerLeuTyrSerSerProCysSerGlnThrSerSerAlaGly | 372 |

Fig. 1A

```
1591  AGCTCGGGCGGCGGCGGCGGCGGCGCGGGGCCCGCGGGGGGCGCGGGCGGCGCC
      SerSerGlyGlyGlyGlyGlyGlyAlaGlyAlaAlaGlyGlyAlaGlyGlyAla          390

1645  GGGACCTACCACTGCAACCTGCAAGCCATGAGCCTGTACGCGGCCGGCGAGCGC
      GlyThrTyrHisCysAsnLeuGlnAlaMETSerLeuTyrAlaAlaGlyGluArg          408

1699  GGGGGCCACTTGCAGGGCGCGCCCGGGGGCGCGGGCGGCTCGGCCGTGGACAAC
      GlyGlyHisLeuGlnGlyAlaProGlyGlyAlaGlyGlySerAlaValAspAsn          426

1753  CCCCTGCCCGACTACTCTCTGCCTCCGGTCACCAGCAGCAGCTCGTCGTCCCTG
      ProLeuProAspTyrSerLeuProProValThrSerSerSerSerSerSerLeu          444

1807  AGTCACGGCGGCGGCGGCGGCGGCGGCGGGGGAGGCCAGGAGGCCGGCCACCAC
      SerHisGlyGlyGlyGlyGlyGlyGlyGlyGlyGlnGluAlaGlyHisHis            462

1861  CCTGCGGCCCACCAAGGCCGCCTCACCTCGTGGTACCTGAACCAGGCGGGCGGA
      ProAlaAlaHisGlnGlyArgLeuThrSerTrpTyrLeuAsnGlnAlaGlyGly          480

1915  GACCTGGGCCACTTGGCAAGCGCGGCGGCGGCGGCGGCGGCCGCAGGCTACCCG
      AspLeuGlyHisLeuAlaSerAlaAlaAlaAlaAlaAlaAlaAlaGlyTyrPro          498

1969  GGCCAGCAGCAGAACTTCCACTCGGTGCGGGAGATGTTCGAGTCACAGAGGATC
      GlyGlnGlnGlnAsnPheHisSerValArgGluMETPheGluSerGlnArgIle          516

2023  GGCTTGAACAACTCTCCAGTGAACGGGAATAGTAGCTGTCAAATGGCCTTCCCT
      GlyLeuAsnAsnSerProValAsnGlyAsnSerSerCysGlnMETAlaPhePro          534

2077  TCCAGCCAGTCTCTGTACCGCACGTCCGGAGCTTTCGTCTACGACTGTAGCAAG
      SerSerGlnSerLeuTyrArgThrSerGlyAlaPheValTyrAspCysSerLys          552

2131  TTTTGAcacaccctcaaagccgaactaaatcgaaccccaaagcaggaaaagcta
      PheSTP                                                          554

2185  aaggaacccatcaaggcaaaatcgaaactaaaaaaaaaaaatccaattaaaaaaaaacccc
2245  tgagaatattcaccacaccagcgaacagaatatccctccaaaaattcagctcaccagcac
2305  cagcacgaagaaaactctattttcttaaccgattaattcagagccacctccactttgcct
2365  tgtctaaataaacaaacccgtaaactgttttatacagagacagcaaaatcttggtttatt
2425  aaaggacagtgttactccagataacacgtaagtttcttcttgcttttcagagacctgctt
2485  tccccctcctcccgtctccctctcttgccttcttccttgcctctcacctgtaagatatta
2545  ttttatcctatgttgaagggagggggaaagtccccgtttatgaaagtcgctttctttttta
2605  ttcatggacttgttttaaaatgtaaattgcaacatagtaatttattttttaatttgtagtt
2665  ggatgtcgtggaccaaacgccagaaagtgttcccaaaacctgacgttaaattgcctgaaa
2725  ctttaaattgtgcttttttttctcattataaaaagggaaactgtattaatcttattctatc
2785  ctcttttcttttctttttgttgaacatattcattgtttgtttattaataaattaccattca
2845  gtttgaatgagacctatatgtctggatactttaatagagctttaattattacgaaaaaag
2905  atttcagagataaaacactagaagttacctattctccacctaaatctctgaaaaatggag
2965  aaaccctctgactagtccatgtcaaattttactaaaagtcttttttgtttagatttatttt
3025  cctgcagcatcttctgcaaaatgtactatatagtcagcttgctttgaggctagtaaaaag
3085  atattttctaaacagattggagttggcatataaacaaatacgttttctcactaatgaca
3145  gtccatgattcggaaatttaagcccatgaatcagccgcggtcttaccacggtgatgcct
3205  gtgtgccgagagatgggactgtgcggccagatatgcacagataaatatttggcttgtgta
3265  ttccatataaaattgcagtgcatattatacatccctgtgagccagatgctgaatagattt
3325  tttcctattatttcagtcctttataaaaggaaaaataaaccagttttttaaatgtatgtat
3485  ataattctcccccatttacaatccttcatgtattacatagaaggattgctttttttaaaa
3445  tatactgcgggttggaaagggatattttaatctttgagaaactattttagaaaatatgttt
3505  gtagaacaattattttttgaaaaagattttaaagcaataacaagaaggaaggcgagaggagc
3565  agaacattttggtctagggtggtttctttttaaaccattttttcttgttaatttacagtt
3625  aaacctaggggacaatccggattggccctcccccttttgtaaataacccaggaaatgtaa
3685  taaattcattatcttagggtgatctgccctgccaatcagactttggggagatggcgattt
3745  gattacagacgttcgggggggtgggggggcttgcagtttgttttggagataatacagtttc
3805  ctgctatctgccgctccatctagaggcaacacttaagcagtaattgctgttgcttgttg
3865  tcaaaatttgatcattgttaaaggattgctgcaaataaatacactttaatttcagtcaaa
3925  aaaaaaaaaaaaaaaaaaaa
```

| Clone Name | Image Number | Organism | Vector | Loc | 5' Sequence | 3" Sequence | Insert Size | Tissue | Contig |
|---|---|---|---|---|---|---|---|---|---|
| zr45a08 | 666326 | Human | | 3' | AA232742 | AA232201 | | NhHMPu | |
| zw04a06 | 768274 | Human | | 3' | | AA424787 | | NhHMPu | |
| zv90g12 | 767110 | Human | | 3' | AA424381 | AA424466 | | NhHMPu | |
| yw76b12 | 258143 | Human | pT7T3D | 3' | N40575 | | | Placenta, 8 to 9 wk | |
| ze13t07 | 358885 | Human | | 3' | | W94629 | | Fetal Heart | |
| yw78d12 | 258359 | Human | | 3' | | N25875 | | Placenta, 8 to 9 wk | |
| zw05a06 | 768370 | Human | pT7T3D | 3' | AA495846 | AA885880 | | NhHMPu | |
| oj36t08 | 1500423 | Human | | 3' | | | | NCI_CGAP_Lu5 | |
| zd71b11 | 346077 | Human | | 3' | W77980 | | | Fetal Heart, 19 wk | |
| ah14c11 | 1156628 | Human | | 3' | | AA776534 | | Wilms Tumor | |
| oh48b09 | 1469849 | Human | | 3' | | AA865139 | | NCI_CGAP_GC4 | |
| zd71b12 | 346079 | Human | | 3' | | W73917 | | Fetal Heart, 19 wk | |
| ze71a01 | 364392 | Human | pT7T3D | 3' | AA022618 | AA022755 | 722 | Fetal Heart, 19 wk | |
| ze13t07 | 358885 | Human | | 3' | W94714 | | | Fetal Heart, 19 wk | |
| ok90g07 | 1521276 | Human | | 3' | | AA902429 | | NCI_CGAP_Lu5 | |
| yw78b12 | 258335 | Human | | 3' | H89575 | N25867 | | Placenta, 8 to 9 wk | |
| yw28c11 | 253556 | Human | pBlue SK- | 3' | AA348051 | | | Fetal Cochlea | |
| EST54452 | | Human | | 3' | AA334694 | | | Fetal Heart | |
| EST38957 | | Human | | 3' | N75774 | | | Embryo, 9 wk | |
| yw30d03 | 253733 | Human | pBlue SK- | 3' | AA551599 | N22552 | 919 | Fetal Cochlea | |
| nj57a04 | 996558 | Human | | 5' | N40582 | | | NCI_CGAP_Pr9 | |
| yw76d12 | 258167 | Human | pT7T3D | 5' | | AA688135 | | Placenta, 8 to 9 wk | |
| nv16g07 | 1220412 | Human | | 5' | D56550 | | | NCI_CGAP_Pr22 | |
| GEN-206f07 | | Human | | 3' | | AA886687 | 475 | Aorta | |
| oj39l04 | 1500703 | Human | | 3' | D57248 | | | NCI_CGAP_Kid3 | |
| GEN-288A05 | | Human | pSPORT1 | 3' | | | | Aorta | |
| vc30a07 | 7776052 | Mouse | pT7T3D | 3' | AA276025 | | | Kidney, 6 wk | |
| vu08t03 | 1180061 | Mouse | | 5' | AA673797 | | | Myotubes | |
| vw64c01 | 1248576 | Mouse | | 5' | AA960591 | AA759405 | | Mammary Gland, 4 wk | |
| vg45c07 | 864300 | Mouse | pT7T3D | 3' | | AA458089 | 936 | Mammary Gland, 4 wk | |
| md53e12 | 372142 | Mouse | pT7T3D | 5' | | W57082 | | Embryo, 13.5-14.5 dy | |
| mt72a07 | 419796 | Mouse | pT7T3D | 5' | W91182 | | | Embryo, 13.5-14.5 dy | |
| vv53d11 | 1226133 | Mouse | pT7T3D | 5' | AA739434 | | | Thymus, 4 wk | |
| me94t07 | 403237 | Mouse | pT7T3D | 3' | | | | Embryo, 13.5-14.5 dy | |
| vc85b07 | | Human | pSPORT1 | 3' | | | | | |
| mo83c06 | | Human | | 3' | | | | Embryo, 11.5 dy | |
| UI-R-AO-al-b-03 | | Rat | | 3' | AA819240 | | | Embryo | |
| UI-R-E1-go-e-12 | | Rat | | 3' | AA964464 | | | | |

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
        (A) LENGTH: 3946 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 475..2133

(xi) SEQUENCE DESCRIPTION: SEQ ID NO:1:

```
CGAGAAAAGG TGACGCGGGG CCCGGGCAGG CGGCCGGCGC GCGGCCCCCC CCCCCCCGC      60

CCTGGTTATT TGGCCGCCTT CGCCGGCAGC TCAGGGCAGA GTCTCCTGGA AGGCGCAGGC    120

AGTGTGGCGA GAAGGGCGCC TGCTTGTTCT TTCTTTTTGT CTGCTTTCCC CCGTTTGCGC    180

CTGGAAGCTG CGCCGCGAGT TCCTGCAAGG CGGTCTGCCG CGGCCGGGCC CGGCCTTCTC    240
```

-continued

```
CCCTCGCAGC GACCCCGCCT CGCGGCCGCG CGGGCCCCGA GGTAGCCCGA GGCGCCGGAG      300

GAGCCAGCCC CAGCGAGCGC CGGGAGAGGC GGCAGCGCAG CCGGACGCAC AGCGCAGCGG      360

GCCGGCACCA GCTCGGCCGG GCCCGGACTC GGACTCGGCG GCCGGCGCGG CGCGGCCCGG      420

CCCGAGCGAG GGTGGGGGGC GGCGGGCGGC GCGGGGCGGC GGCGAGCGGG GGCC ATG       477
                                                           Met
                                                             1

CAG GCG CGC TAC TCC GTG TCC AGC CCC AAC TCC CTG GGA GTG GTG CCC       525
Gln Ala Arg Tyr Ser Val Ser Ser Pro Asn Ser Leu Gly Val Val Pro
          5                  10                  15

TAC CTC GGC GGC GAG CAG AGC TAC TAC CGC GCG GCG GCC GCG GCG GCC       573
Tyr Leu Gly Gly Glu Gln Ser Tyr Tyr Arg Ala Ala Ala Ala Ala Ala
         20                  25                  30

GGG GGC GGC TAC ACC GCC ATG CCG GCC CCC ATG AGC GTG TAC TCG CAC       621
Gly Gly Gly Tyr Thr Ala Met Pro Ala Pro Met Ser Val Tyr Ser His
     35                  40                  45

CCT GCG CAC GCC GAG CAG TAC CCG GGC GGC ATG GCC CGC GCC TAC GGG       669
Pro Ala His Ala Glu Gln Tyr Pro Gly Gly Met Ala Arg Ala Tyr Gly
 50                  55                  60                  65

CCC TAC ACG CCG CAG CCG CAG CCC AAG GAC ATG GTG AAG CCG CCC TAT       717
Pro Tyr Thr Pro Gln Pro Gln Pro Lys Asp Met Val Lys Pro Pro Tyr
                 70                  75                  80

AGC TAC ATC GCG CTC ATC ACC ATG GCC ATC CAG AAC GCC CCG GAC AAG       765
Ser Tyr Ile Ala Leu Ile Thr Met Ala Ile Gln Asn Ala Pro Asp Lys
             85                  90                  95

AAG ATC ACC CTG AAC GGC ATC TAC CAG TTC ATC ATG GAC CGC TTC CCC       813
Lys Ile Thr Leu Asn Gly Ile Tyr Gln Phe Ile Met Asp Arg Phe Pro
        100                 105                 110

TTC TAC CGG GAC AAC AAG CAG GGC TGG CAG AAC AGC ATC CGC CAC AAC       861
Phe Tyr Arg Asp Asn Lys Gln Gly Trp Gln Asn Ser Ile Arg His Asn
    115                 120                 125

CTC TCG CTC AAC GAG TGC TTC GTC AAG GTG CCG CGC GAC GAC AAG AAG       909
Leu Ser Leu Asn Glu Cys Phe Val Lys Val Pro Arg Asp Asp Lys Lys
130                 135                 140                 145

CCG GGC AAG GGC AGC TAC TGG ACG CTG GAC CCG GAC TCC TAC AAC ATG       957
Pro Gly Lys Gly Ser Tyr Trp Thr Leu Asp Pro Asp Ser Tyr Asn Met
                150                 155                 160

TTC GAG AAC GGC AGC TTC CTG CGG CGG CGG CGG CGC TTC AAG AAG AAG      1005
Phe Glu Asn Gly Ser Phe Leu Arg Arg Arg Arg Arg Phe Lys Lys Lys
            165                 170                 175

GAC GCG GTG AAG GAC AAG GAG GAG AAG GAC AGG CTG CAC CTC AAG GAG      1053
Asp Ala Val Lys Asp Lys Glu Glu Lys Asp Arg Leu His Leu Lys Glu
        180                 185                 190

CCG CCC CCG CCC GGC CGC CAG CCC CCG CCC GCG CCG CCG GAG CAG GCC      1101
Pro Pro Pro Pro Gly Arg Gln Pro Pro Pro Ala Pro Pro Glu Gln Ala
    195                 200                 205

GAC GGC AAC GCG CCC GGT CCG CAG CCG CCG CCC GTG CGC ATC CAG GAC      1149
Asp Gly Asn Ala Pro Gly Pro Gln Pro Pro Pro Val Arg Ile Gln Asp
210                 215                 220                 225

ATC AAG ACC GAG AAC GGT ACG TGC CCC TCG CCG CCC CAG CCC CTG TCC      1197
Ile Lys Thr Glu Asn Gly Thr Cys Pro Ser Pro Pro Gln Pro Leu Ser
                230                 235                 240

CCG GCC GCC GCC CTG GGC AGC GGC AGC GCC GCC GCG GTG CCC AAG ATC      1245
Pro Ala Ala Ala Leu Gly Ser Gly Ser Ala Ala Ala Val Pro Lys Ile
            245                 250                 255

GAG AGC CCC GAC AGC AGC AGC AGC AGC CTG TCC AGC GGG AGC AGC CCC      1293
Glu Ser Pro Asp Ser Ser Ser Ser Ser Leu Ser Ser Gly Ser Ser Pro
        260                 265                 270

CCG GGC AGC CTG CCG TCG GCG CGG CCG CTC AGC CTG GAC GGT GCG GAT      1341
```

-continued

```
Pro Gly Ser Leu Pro Ser Ala Arg Pro Leu Ser Leu Asp Gly Ala Asp
    275                 280                 285

TCC GCG CCG CCG CCG CCC GCG CCC TCC GCC CCG CCG CCG CAC CAT AGC       1389
Ser Ala Pro Pro Pro Ala Pro Ser Ala Pro Pro Pro His His Ser
290                 295                 300                 305

CAG GGC TTC AGC GTG GAC AAC ATC ATG ACG TCG CTG CGG GGG TCG CCG       1437
Gln Gly Phe Ser Val Asp Asn Ile Met Thr Ser Leu Arg Gly Ser Pro
                    310                 315                 320

CAG AGC GCG GCC GCG GAG CTC AGC TCC GGC CTT CTG GCC TCG GCG GCC       1485
Gln Ser Ala Ala Ala Glu Leu Ser Ser Gly Leu Leu Ala Ser Ala Ala
                325                 330                 335

GCG TCC TCG CGC GCG GGG ATC GCA CCC CCG CTG GCG CTC GGC GCC TAC       1533
Ala Ser Ser Arg Ala Gly Ile Ala Pro Pro Leu Ala Leu Gly Ala Tyr
            340                 345                 350

TCG CCC GGC CAG AGC TCC CTC TAC AGC TCC CCC TGC AGC CAG ACC TCC       1581
Ser Pro Gly Gln Ser Ser Leu Tyr Ser Ser Pro Cys Ser Gln Thr Ser
355                 360                 365

AGC GCG GGC AGC TCG GGC GGC GGC GGC GGC GCG GGG GCC GCG GGG           1629
Ser Ala Gly Ser Ser Gly Gly Gly Gly Gly Ala Gly Ala Ala Gly
370                 375                 380                 385

GGC GCG GGC GGC GCC GGG ACC TAC CAC TGC AAC CTG CAA GCC ATG AGC       1677
Gly Ala Gly Gly Ala Gly Thr Tyr His Cys Asn Leu Gln Ala Met Ser
                    390                 395                 400

CTG TAC GCG GCC GGC GAG CGC GGG GGC CAC TTG CAG GGC GCG CCC GGG       1725
Leu Tyr Ala Ala Gly Glu Arg Gly Gly His Leu Gln Gly Ala Pro Gly
                405                 410                 415

GGC GCG GGC GGC TCG GCC GTG GAC AAC CCC CTG CCC GAC TAC TCT CTG       1773
Gly Ala Gly Gly Ser Ala Val Asp Asn Pro Leu Pro Asp Tyr Ser Leu
            420                 425                 430

CCT CCG GTC ACC AGC AGC AGC TCG TCG TCC CTG AGT CAC GGC GGC GGC       1821
Pro Pro Val Thr Ser Ser Ser Ser Ser Ser Leu Ser His Gly Gly Gly
435                 440                 445

GGC GGC GGC GGC GGG GGA GGC CAG GAG GCC GGC CAC CAC CCT GCG GCC       1869
Gly Gly Gly Gly Gly Gly Gly Gln Glu Ala Gly His His Pro Ala Ala
450                 455                 460                 465

CAC CAA GGC CGC CTC ACC TCG TGG TAC CTG AAC CAG GCG GGC GGA GAC       1917
His Gln Gly Arg Leu Thr Ser Trp Tyr Leu Asn Gln Ala Gly Gly Asp
                    470                 475                 480

CTG GGC CAC TTG GCA AGC GCG GCG GCG GCG GCG GCC GCA GGC TAC           1965
Leu Gly His Leu Ala Ser Ala Ala Ala Ala Ala Ala Ala Gly Tyr
                485                 490                 495

CCG GGC CAG CAG CAG AAC TTC CAC TCG GTG CGG GAG ATG TTC GAG TCA      2013
Pro Gly Gln Gln Gln Asn Phe His Ser Val Arg Glu Met Phe Glu Ser
            500                 505                 510

CAG AGG ATC GGC TTG AAC AAC TCT CCA GTG AAC GGG AAT AGT AGC TGT      2061
Gln Arg Ile Gly Leu Asn Asn Ser Pro Val Asn Gly Asn Ser Ser Cys
515                 520                 525

CAA ATG GCC TTC CCT TCC AGC CAG TCT CTG TAC CGC ACG TCC GGA GCT      2109
Gln Met Ala Phe Pro Ser Ser Gln Ser Leu Tyr Arg Thr Ser Gly Ala
530                 535                 540                 545

TTC GTC TAC GAC TGT AGC AAG TTT TGACACACCC TCAAAGCCGA ACTAAATCGA     2163
Phe Val Tyr Asp Cys Ser Lys Phe
                    550

ACCCCAAAGC AGGAAAAGCT AAAGGAACCC ATCAAGGCAA AATCGAAACT AAAAAAAAAA   2223

AATCCAATTA AAAAAACCC CTGAGAATAT TCACCACACC AGCGAACAGA ATATCCCTCC    2283

AAAAATTCAG CTCACCAGCA CCAGCACGAA GAAAACTCTA TTTTCTTAAC CGATTAATTC   2343

AGAGCCACCT CCACTTTGCC TTGTCTAAAT AAACAAACCC GTAAACTGTT TTATACAGAG   2403
```

```
ACAGCAAAAT CTTGGTTTAT TAAAGGACAG TGTTACTCCA GATAACACGT AAGTTTCTTC    2463

TTGCTTTTCA GAGACCTGCT TTCCCCTCCT CCCGTCTCCC CTCTCTTGCC TTCTTCCTTG    2523

CCTCTCACCT GTAAGATATT ATTTTATCCT ATGTTGAAGG GAGGGGGAAA GTCCCCGTTT    2583

ATGAAAGTCG CTTTCTTTTT ATTCATGGAC TTGTTTTAAA ATGTAAATTG CAACATAGTA    2643

ATTTATTTTT AATTTGTAGT TGGATGTCGT GGACCAAACG CCAGAAAGTG TTCCCAAAAC    2703

CTGACGTTAA ATTGCCTGAA ACTTTAAATT GTGCTTTTTT TCTCATTATA AAAGGGAAA    2763

CTGTATTAAT CTTATTCTAT CCTCTTTTCT TTCTTTTTGT TGAACATATT CATTGTTTGT    2823

TTATTAATAA ATTACCATTC AGTTTGAATG AGACCTATAT GTCTGGATAC TTTAATAGAG    2883

CTTTAATTAT TACGAAAAAA GATTTCAGAG ATAAAACACT AGAAGTTACC TATTCTCCAC    2943

CTAAATCTCT GAAAATGGA GAAACCCTCT GACTAGTCCA TGTCAAATTT TACTAAAAGT    3003

CTTTTTGTTT AGATTTATTT TCCTGCAGCA TCTTCTGCAA AATGTACTAT ATAGTCAGCT    3063

TGCTTTGAGG CTAGTAAAAA GATATTTTTC TAAACAGATT GGAGTTGGCA TATAAACAAA    3123

TACGTTTTCT CACTAATGAC AGTCCATGAT TCGGAAATTT TAAGCCCATG AATCAGCCGC    3183

GGTCTTACCA CGGTGATGCC TGTGTGCCGA GAGATGGGAC TGTGCGGCCA GATATGCACA    3243

GATAAATATT TGGCTTGTGT ATTCCATATA AAATTGCAGT GCATATTATA CATCCCTGTG    3303

AGCCAGATGC TGAATAGATT TTTTCCTATT ATTTCAGTCC TTTATAAAAG GAAAATAAA    3363

CCAGTTTTTA AATGTATGTA TATAATTCTC CCCCATTTAC AATCCTTCAT GTATTACATA    3423

GAAGGATTGC TTTTTTAAAA ATATACTGCG GGTTGGAAAG GGATATTTAA TCTTTGAGAA    3483

ACTATTTTAG AAAATATGTT TGTAGAACAA TTATTTTTGA AAAAGATTTA AAGCAATAAC    3543

AAGAAGGAAG GCGAGAGGAG CAGAACATTT TGGTCTAGGG TGGTTTCTTT TTAAACCATT    3603

TTTTCTTGTT AATTTACAGT TAAACCTAGG GGACAATCCG GATTGGCCCT CCCCCTTTTG    3663

TAAATAACCC AGGAAATGTA ATAAATTCAT TATCTTAGGG TGATCTGCCC TGCCAATCAG    3723

ACTTTGGGGA GATGGCGATT TGATTACAGA CGTTCGGGGG GGTGGGGGGC TTGCAGTTTG    3783

TTTTGGAGAT AATACAGTTT CCTGCTATCT GCCGCTCCTA TCTAGAGGCA ACACTTAAGC    3843

AGTAATTGCT GTTGCTTGTT GTCAAAATTT GATCATTGTT AAAGGATTGC TGCAAATAAA    3903

TACACTTTAA TTTCAGTCAA AAAAAAAAAA AAAAAAAAA AAA                       3946

(2) INFORMATION FOR SEQ ID NO:2:

(i) SEQUENCE CHARACTERISTICS:
        (A) LENGTH: 553 amino acids
        (B) TYPE: amino acid
        (D) TOPOLOGY: linear (ii) MOLECULE TYPE: protein (xi) SEQUENCE DESCRIPTION: SEQ ID NO:2:

Met Gln Ala Arg Tyr Ser Val Ser Ser Pro Asn Ser Leu Gly Val Val
 1               5                  10                  15

Pro Tyr Leu Gly Gly Glu Gln Ser Tyr Tyr Arg Ala Ala Ala Ala
            20                  25                  30

Ala Gly Gly Gly Tyr Thr Ala Met Pro Ala Pro Met Ser Val Tyr Ser
        35                  40                  45

His Pro Ala His Ala Glu Gln Tyr Pro Gly Gly Met Ala Arg Ala Tyr
    50                  55                  60

Gly Pro Tyr Thr Pro Gln Pro Gln Pro Lys Asp Met Val Lys Pro Pro
65                  70                  75                  80
```

-continued

```
Tyr Ser Tyr Ile Ala Leu Ile Thr Met Ala Ile Gln Asn Ala Pro Asp
                85                  90                  95

Lys Lys Ile Thr Leu Asn Gly Ile Tyr Gln Phe Ile Met Asp Arg Phe
            100                 105                 110

Pro Phe Tyr Arg Asp Asn Lys Gln Gly Trp Gln Asn Ser Ile Arg His
        115                 120                 125

Asn Leu Ser Leu Asn Glu Cys Phe Val Lys Val Pro Arg Asp Asp Lys
    130                 135                 140

Lys Pro Gly Lys Gly Ser Tyr Trp Thr Leu Asp Pro Asp Ser Tyr Asn
145                 150                 155                 160

Met Phe Glu Asn Gly Ser Phe Leu Arg Arg Arg Arg Phe Lys Lys
            165                 170                 175

Lys Asp Ala Val Lys Asp Lys Glu Glu Lys Asp Arg Leu His Leu Lys
                180                 185                 190

Glu Pro Pro Pro Pro Gly Arg Gln Pro Pro Ala Pro Pro Glu Gln
                195                 200                 205

Ala Asp Gly Asn Ala Pro Gly Pro Gln Pro Pro Val Arg Ile Gln
    210                 215                 220

Asp Ile Lys Thr Glu Asn Gly Thr Cys Pro Ser Pro Pro Gln Pro Leu
225                 230                 235                 240

Ser Pro Ala Ala Ala Leu Gly Ser Gly Ser Ala Ala Val Pro Lys
                245                 250                 255

Ile Glu Ser Pro Asp Ser Ser Ser Ser Ser Leu Ser Ser Gly Ser Ser
                260                 265                 270

Pro Pro Gly Ser Leu Pro Ser Ala Arg Pro Leu Ser Leu Asp Gly Ala
            275                 280                 285

Asp Ser Ala Pro Pro Pro Ala Pro Ser Ala Pro Pro His His
    290                 295                 300

Ser Gln Gly Phe Ser Val Asp Asn Ile Met Thr Ser Leu Arg Gly Ser
305                 310                 315                 320

Pro Gln Ser Ala Ala Ala Glu Leu Ser Ser Gly Leu Leu Ala Ser Ala
                325                 330                 335

Ala Ala Ser Ser Arg Ala Gly Ile Ala Pro Pro Leu Ala Leu Gly Ala
                340                 345                 350

Tyr Ser Pro Gly Gln Ser Ser Leu Tyr Ser Ser Pro Cys Ser Gln Thr
            355                 360                 365

Ser Ser Ala Gly Ser Ser Gly Gly Gly Gly Gly Ala Gly Ala Ala
    370                 375                 380

Gly Gly Ala Gly Gly Ala Gly Thr Tyr His Cys Asn Leu Gln Ala Met
385                 390                 395                 400

Ser Leu Tyr Ala Ala Gly Glu Arg Gly Gly His Leu Gln Gly Ala Pro
            405                 410                 415

Gly Gly Ala Gly Gly Ser Ala Val Asp Asn Pro Leu Pro Asp Tyr Ser
                420                 425                 430

Leu Pro Pro Val Thr Ser Ser Ser Ser Ser Leu Ser His Gly Gly
        435                 440                 445

Gly Gly Gly Gly Gly Gly Gly Gln Glu Ala Gly His His Pro Ala
    450                 455                 460

Ala His Gln Gly Arg Leu Thr Ser Trp Tyr Leu Asn Gln Ala Gly Gly
465                 470                 475                 480

Asp Leu Gly His Leu Ala Ser Ala Ala Ala Ala Ala Ala Gly
            485                 490                 495

Tyr Pro Gly Gln Gln Gln Asn Phe His Ser Val Arg Glu Met Phe Glu
```

-continued

```
                500                 505                 510
Ser Gln Arg Ile Gly Leu Asn Asn Ser Pro Val Asn Gly Asn Ser Ser
            515                 520                 525

Cys Gln Met Ala Phe Pro Ser Ser Gln Ser Leu Tyr Arg Thr Ser Gly
            530                 535                 540

Ala Phe Val Tyr Asp Cys Ser Lys Phe
545                 550
```

(2) INFORMATION FOR SEQ ID NO:3:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
ATGCAGGCGC GCTACTCCGT GTCCAGCCCC AACTCCCTGG GAGTGGTGCC CTACCTCGGC      60
GGCGAGCAGA GCTACTACCG CGCGGCGGCC GCGGCGGCCG GGGGCGGCTA CACCGCCATG     120
CCGGCCCCCA TGAGCGTGTA CTCGCACCCT GCGCACGCCG AGCAGTACCC GGGCGGCATG     180
GCCCGCGCCT ACGGGCCCTA CACGCCGCAG CCGCAGCCCA AGGACATGGT GAAGCCGCCC     240
TATAGCTACA TCGCGCTCAT CACCATGGCC ATCCAGAACG CCCCGGACAA GAAGATCACC     300
CTGAACGGCA TCTACCAGTT CATCATGGAC CGCTTCCCCT TCTACCGGGA CAACAAGCAG     360
GGCTGGCAGA ACAGCATCCG CCACAACCTC TCGCTCAACG AGTGCTTCGT CAAGGTGCCG     420
CGCGACGACA AGAAGCCGGG CAAGGGCAGC TACTGGACGG TGGACCCCGA CTCCTACAAC     480
ATGTTCGAGA ACGGCAGCTT CCTGCGGCGG CGGCGGCGCT TCAAGAAGAA GGACGCGGTG     540
AAGGACAAGG AGGAGAAGGA CAGGCTGCAC CTCAAGGAGC CGCCCCCGCC CGGCCGCCAG     600
CCCCCGCCCG CGCCGCCGGA GCAGGCCGAC GGCAACGCGC CCGGTCCGCA GCCGCCGCCC     660
GTGCGCATCC AGGACATCAA GACCGAGAAC GGTACGTGCC CCTCGCCGCC CCAGCCCCTG     720
TCCCCGGCCG CCGCCCTGGG CAGCGGCAGC GCCGCCGCGG TGCCCAAGAT CGAGAGCCCC     780
GACAGCAGCA GCAGCAGCCT GTCCAGCGGG AGCAGCCCCC CGGGCAGCCT GCCGTCGGCG     840
CGGCCGCTCA GCCTGGACGG TGCGGATTCC GCGCCGCCGC CGCCCGCGCC CTCCGCCCCG     900
CCGCCGCACC ATAGCCAGGG CTTCAGCGTG GACAACATCA TGACGTCGCT GCGGGGGTCG     960
CCGCAGAGCG CGGCCGCGGA GCTCAGCTCC GGCCTTCTGG CCTCGGCGGC CGCGTCCTCG    1020
CGCGCGGGGA TCGCACCCCC GCTGGCGCTC GGCGCCTACT CGCCCGGCCA GAGCTCCCTC    1080
TACAGCTCCC CCTGCAGCCA GACCTCCAGC GCGGGCAGCT CGGGCGGCGG CGGCGGCGGC    1140
GCGGGGGCCG CGGGGGGCGC GGGCGGCGCC GGGACCTACC ACTGCAACCT GCAAGCCATG    1200
AGCCTGTACG CGGCCGGCGA GCGCGGGGGC CACTTGCAGG GCGCGCCCGG GGGCGCGGGC    1260
GGCTCGGCCG TGGACAACCC CCTGCCCGAC TACTCTCTGC CTCCGGTCAC CAGCAGCAGC    1320
TCGTCGTCCC TGAGTCACGG CGGCGGCGGC GGCGGCGGCG GGGAGGCCA GGAGGCCGGC     1380
CACCACCCTG CGGCCCACCA AGGCCGCCTC ACCTCGTGGT ACCTGAACCA GGCGGGCGGA    1440
GACCTGGGCC ACTTGGCAAG CGCGGCGGCG GCGGCGGCGG CCGCAGGCTA CCCGGGCCAG    1500
CAGCAGAACT TCCACTCGGT GCGGGAGATG TTCGAGTCAC AGAGGATCGG CTTGAACAAC    1560
TCTCCAGTGA ACGGGAATAG TAGCTGTCAA ATGGCCTTCC CTTCCAGCCA GTCTCTGTAC    1620
CGCACGTCCG GAGCTTTCGT CTACGACTGT AGCAAGTTT                          1659
```

(2) INFORMATION FOR SEQ ID NO:4:

(i) SEQUENCE CHARACTERISTICS:
        (A) LENGTH: 106 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

```
Ser Tyr Thr His Ala Lys Pro Pro Tyr Ser Tyr Ile Ser Leu Ile Thr
1               5                   10                  15

Met Ala Ile Gln Asn Asn Pro Thr Arg Met Leu Thr Leu Ser Glu Ile
            20                  25                  30

Tyr Gln Phe Ile Met Asp Leu Phe Pro Phe Tyr Arg Gln Asn Gln Gln
                35                  40                  45

Arg Trp Gln Asn Ser Ile Arg His Ser Leu Ser Phe Asn Asp Cys Phe
        50                  55                  60

Val Lys Ile Pro Arg Thr Pro Asp Lys Pro Gly Lys Gly Ser Phe Trp
65                  70                  75                  80

Thr His Leu Pro Asp Ser Gly Asn Met Phe Glu Asn Gly Cys Tyr Leu
                    85                  90                  95

Arg Arg Gln Lys Arg Phe Lys Cys Asp Lys
                100                 105
```

(2) INFORMATION FOR SEQ ID NO:5:

(i) SEQUENCE CHARACTERISTICS:
        (A) LENGTH: 106 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

```
Pro Lys Asp Met Val Lys Pro Pro Tyr Ser Tyr Ile Ala Leu Ile Thr
1               5                   10                  15

Met Ala Ile Gln Asn Ala Pro Asp Lys Lys Ile Thr Leu Asn Gly Ile
            20                  25                  30

Tyr Gln Phe Ile Met Asp Arg Phe Pro Phe Tyr Arg Asp Asn Lys Gln
                35                  40                  45

Gly Trp Gln Asn Ser Ile Arg His Asn Leu Ser Leu Asn Glu Cys Phe
        50                  55                  60

Val Lys Val Pro Arg Asp Asp Lys Lys Pro Gly Lys Gly Ser Tyr Trp
65                  70                  75                  80

Thr Leu Asp Pro Asp Ser Tyr Asn Met Phe Glu Asn Gly Ser Phe Leu
                    85                  90                  95

Arg Arg Arg Arg Arg Phe Lys Lys Lys Asp
                100                 105
```

(2) INFORMATION FOR SEQ ID NO:6:

(i) SEQUENCE CHARACTERISTICS:
        (A) LENGTH: 106 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

```
Pro Lys Asp Leu Val Lys Pro Pro Tyr Ser Tyr Ile Ala Leu Ile Thr
1               5                   10                  15

Met Ala Ile Gln Asn Ala Pro Glu Lys Lys Ile Thr Leu Asn Gly Ile
                20                  25                  30

Tyr Gln Phe Ile Met Asp Arg Phe Pro Phe Tyr Arg Glu Asn Lys Gln
                35                  40                  45

Gly Trp Gln Asn Ser Ile Arg His Asn Leu Ser Leu Asn Glu Cys Phe
            50                  55                  60

Val Lys Val Pro Arg Asp Asp Lys Pro Gly Lys Gly Ser Tyr Trp
65                  70                  75                  80

Thr Leu Asp Pro Asp Ser Tyr Asn Met Phe Glu Asn Gly Ser Phe Leu
                85                  90                  95

Arg Arg Arg Arg Arg Phe Lys Lys Lys Asp
                100                 105
```

(2) INFORMATION FOR SEQ ID NO:7:

(i) SEQUENCE CHARACTERISTICS:
        (A) LENGTH: 106 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

```
Thr Thr Glu Pro Thr Lys Pro Pro Tyr Ser Tyr Ile Ala Leu Ile Ala
1               5                   10                  15

Met Ala Ile Gln Ser Ser Pro Gly Gln Arg Ala Thr Leu Ser Gly Ile
                20                  25                  30

Tyr Arg Tyr Ile Met Gly Arg Phe Ala Phe Tyr Arg His Asn Arg Pro
                35                  40                  45

Gly Trp Gln Asn Ser Ile Arg His Asn Leu Ser Leu Asn Glu Cys Phe
            50                  55                  60

Val Lys Val Pro Arg Asp Asp Arg Lys Pro Gly Lys Gly Ser Tyr Trp
65                  70                  75                  80

Thr Leu Asp Pro Asp Cys His Asp Met Phe Glu His Gly Ser Phe Leu
                85                  90                  95

Arg Arg Arg Arg Arg Phe Thr Arg Gln Thr
                100                 105
```

(2) INFORMATION FOR SEQ ID NO:8:

(i) SEQUENCE CHARACTERISTICS:
        (A) LENGTH: 106 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

```
Ala Glu Thr Pro Gln Lys Pro Pro Tyr Ser Tyr Ile Ala Leu Ile Ala
1               5                   10                  15

Met Ala Ile Gln Asp Ala Pro Glu Gln Arg Val Thr Leu Asn Gly Ile
                20                  25                  30

Tyr Gln Phe Ile Met Asp Arg Phe Pro Phe Tyr His Asp Asn Arg Gln
                35                  40                  45
```

```
Gly Trp Gln Asn Ser Ile Arg His Asn Leu Ser Leu Asn Asp Cys Phe
    50                  55                  60

Val Lys Val Pro Arg Glu Lys Gly Arg Pro Gly Lys Gly Ser Tyr Trp
65              70                  75                      80

Thr Leu Asp Pro Arg Cys Leu Asp Met Phe Glu Asn Gly Asn Phe Leu
                85                  90                  95

Arg Arg Lys Arg Lys Pro Lys Pro Gly Pro
            100                 105
```

(2) INFORMATION FOR SEQ ID NO:9:

(i) SEQUENCE CHARACTERISTICS:
        (A) LENGTH: 106 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:9:

```
Pro Leu Gln Arg Gly Lys Pro Pro Tyr Ser Tyr Ile Ala Leu Ile Ala
1               5                   10                  15

Met Ala Leu Ala His Ala Pro Gly Arg Arg Leu Thr Leu Ala Ala Ile
            20                  25                  30

Tyr Arg Phe Ile Thr Glu Arg Phe Ala Phe Tyr Arg Asp Ser Pro Arg
            35                  40                  45

Lys Trp Gln Asn Ser Ile Arg His Asn Leu Thr Leu Asn Asp Cys Phe
    50                  55                  60

Val Lys Val Pro Arg Glu Pro Gly Asn Pro Gly Lys Gly Asn Tyr Trp
65              70                  75                      80

Thr Leu Asp Pro Ala Ala Ala Asp Met Phe Asp Asn Gly Ser Phe Leu
                85                  90                  95

Pro Arg Arg Lys Arg Phe Lys Arg Ala Glu
            100                 105
```

(2) INFORMATION FOR SEQ ID NO:10:

(i) SEQUENCE CHARACTERISTICS:
        (A) LENGTH: 106 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

```
Pro Leu Gln Arg Gly Lys Pro Pro Tyr Ser Tyr Ile Ala Leu Ile Ala
1               5                   10                  15

Met Ala Ile Ala His Ala Pro Glu Arg Arg Leu Thr Leu Gly Gly Ile
            20                  25                  30

Tyr Lys Phe Ile Thr Glu Arg Phe Pro Phe Tyr Arg Asp Asn Pro Lys
            35                  40                  45

Lys Trp Gln Asn Ser Ile Arg His Asn Leu Thr Leu Asn Asp Cys Phe
    50                  55                  60

Leu Lys Ile Pro Arg Glu Ala Gly His Pro Gly Lys Gly Asn Tyr Trp
65              70                  75                      80

Ala Leu Asp Pro Asn Ala Glu Asp Met Phe Glu Ser Gly Ser Phe Leu
                85                  90                  95

Arg Arg Arg Lys Arg Phe Lys Arg Ser Asp
            100                 105
```

(2) INFORMATION FOR SEQ ID NO:11:

(i) SEQUENCE CHARACTERISTICS:
        (A) LENGTH: 106 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:11:

```
Ala Arg Gln Pro Ala Lys Pro Pro Ser Ser Tyr Ile Ala Leu Ile Thr
 1               5                  10                  15

Met Ala Ile Leu Gln Ser Pro His Lys Arg Leu Thr Leu Ser Gly Ile
             20                  25                  30

Cys Ala Phe Ile Ser Asp Arg Phe Pro Tyr Tyr Arg Arg Lys Phe Pro
             35                  40                  45

Gly Trp Gln Asn Ser Ile Arg His Asn Leu Ser Leu Asn Arg Cys Phe
         50                  55                  60

Val Lys Ile Pro Arg Glu Pro Gly Arg Pro Gly Lys Gly Asn Tyr Trp
 65                  70                  75                  80

Ser Leu Asp Pro Ala Ser Gln Asp Met Phe Asp Asn Gly Ser Phe Leu
                 85                  90                  95

Arg Arg Arg Lys Arg Phe Gln Arg His Gln
                100                 105
```

(2) INFORMATION FOR SEQ ID NO:12:

(i) SEQUENCE CHARACTERISTICS:
        (A) LENGTH: 106 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

```
Arg Thr Arg Leu Val Lys Pro Pro Tyr Ser Tyr Ile Ala Leu Ile Thr
 1               5                  10                  15

Met Ala Ile Leu Gln Ser Pro Lys Lys Arg Leu Thr Leu Ser Glu Ile
             20                  25                  30

Cys Glu Phe Ile Ser Gly Arg Phe Pro Tyr Tyr Arg Glu Lys Phe Pro
             35                  40                  45

Ala Trp Gln Asn Ser Ile Arg His Asn Leu Ser Leu Asn Asp Cys Phe
         50                  55                  60

Val Lys Ile Pro Arg Glu Pro Gly Asn Pro Gly Lys Gly Asn Tyr Trp
 65                  70                  75                  80

Thr Leu Asp Pro Glu Ser Ala Asp Met Phe Asp Asn Gly Ser Phe Leu
                 85                  90                  95

Arg Arg Arg Lys Arg Phe Lys Arg Gln Pro
                100                 105
```

(2) INFORMATION FOR SEQ ID NO:13:

(i) SEQUENCE CHARACTERISTICS:
        (A) LENGTH: 106 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:13:

Arg Ser Pro Leu Val Lys Pro Pro Tyr Ser Tyr Ile Ala Leu Ile Thr
1               5                   10                  15

Met Ala Ile Leu Gln Ser Pro Lys Lys Arg Leu Thr Leu Ser Glu Ile
            20                  25                  30

Cys Glu Phe Ile Ser Gly Arg Phe Pro Tyr Tyr Arg Glu Lys Phe Pro
            35                  40                  45

Ala Trp Gln Asn Ser Ile Arg His Asn Leu Ser Leu Asn Asp Cys Phe
        50                  55                  60

Val Lys Ile Pro Arg Glu Pro Gly Asn Pro Gly Lys Gly Asn Tyr Trp
65                  70                  75                  80

Thr Leu Asp Pro Glu Ser Ala Asp Met Phe Asp Asn Gly Ser Phe Leu
                85                  90                  95

Arg Arg Arg Lys Arg Phe Lys Arg Gln Pro
                100                 105

(2) INFORMATION FOR SEQ ID NO:14:

(i) SEQUENCE CHARACTERISTICS:
         (A) LENGTH: 106 amino acids
         (B) TYPE: amino acid
         (C) STRANDEDNESS:
         (D) TOPOLOGY: linear (ii) MOLECULE TYPE: protein (xi) SEQUENCE DESCRIPTION: SEQ ID NO:14:

Ile Arg Arg Pro Glu Lys Pro Pro Tyr Ser Tyr Ile Ala Leu Ile Val
1               5                   10                  15

Met Ala Ile Gln Ser Ser Pro Thr Lys Arg Leu Thr Leu Ser Glu Ile
            20                  25                  30

Tyr Gln Phe Leu Gln Ser Arg Phe Pro Phe Phe Arg Gly Ser Tyr Gln
            35                  40                  45

Gly Trp Lys Asn Ser Val Arg His Asn Leu Ser Leu Asn Glu Cys Phe
        50                  55                  60

Ile Lys Leu Pro Lys Gly Leu Gly Arg Pro Gly Lys Gly His Tyr Trp
65                  70                  75                  80

Thr Ile Asp Pro Ala Ser Glu Phe Met Phe Glu Asn Gly Ser Phe Arg
                85                  90                  95

Arg Arg Arg Arg Gly Phe Arg Arg Lys Cys
                100                 105

(2) INFORMATION FOR SEQ ID NO:15:

(i) SEQUENCE CHARACTERISTICS:
         (A) LENGTH: 106 amino acids
         (B) TYPE: amino acid
         (C) STRANDEDNESS:
         (D) TOPOLOGY: linear (ii) MOLECULE TYPE: protein (xi) SEQUENCE DESCRIPTION: SEQ ID NO:15:

Leu Arg Arg Pro Glu Lys Pro Pro Tyr Ser Tyr Ile Ala Leu Ile Val
1               5                   10                  15

Met Ala Ile Gln Ser Ser Pro Ser Lys Arg Leu Thr Leu Ser Glu Ile
            20                  25                  30

Tyr Gln Phe Leu Gln Ala Arg Phe Pro Phe Phe Arg Gly Ala Tyr Gln

```
                35                  40                  45
Gly Trp Lys Asn Ser Val Arg His Asn Leu Ser Leu Asn Glu Cys Phe
 50                  55                  60

Ile Lys Leu Pro Lys Gly Leu Gly Arg Pro Gly Lys Gly His Tyr Trp
 65                  70                  75                  80

Thr Ile Asp Pro Ala Ser Glu Phe Met Phe Glu Asn Gly Ser Phe Arg
                 85                  90                  95

Arg Arg Arg Arg Gly Phe Arg Arg Lys Cys
                100                 105
```

(2) INFORMATION FOR SEQ ID NO:16:

(i) SEQUENCE CHARACTERISTICS:
        (A) LENGTH: 106 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:16:

```
Asn Gly Lys Tyr Glu Lys Pro Pro Phe Ser Tyr Asn Ala Leu Ile Met
 1               5                  10                  15

Met Ala Ile Arg Gln Ser Pro Glu Lys Arg Leu Thr Leu Asn Gly Ile
                 20                  25                  30

Tyr Glu Phe Ile Met Lys Asn Phe Pro Tyr Tyr Arg Glu Asn Lys Gln
                 35                  40                  45

Gly Trp Gln Asn Ser Ile Arg His Asn Leu Ser Leu Asn Lys Cys Phe
 50                  55                  60

Val Lys Val Pro Arg His Tyr Asp Asp Pro Gly Lys Gly Asn Tyr Trp
 65                  70                  75                  80

Met Leu Asp Pro Ser Ser Asp Asp Val Phe Ile Gly Gly Thr Thr Gly
                 85                  90                  95

Lys Leu Arg Arg Arg Ser Thr Thr Ser Pro
                100                 105
```

(2) INFORMATION FOR SEQ ID NO:17:

(i) SEQUENCE CHARACTERISTICS:
        (A) LENGTH: 106 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:17:

```
Asn Gly Lys Tyr Glu Lys Pro Pro Phe Ser Tyr Asn Ala Leu Ile Met
 1               5                  10                  15

Met Ala Met Arg Gln Ser Pro Glu Lys Arg Leu Thr Leu Asn Gly Ile
                 20                  25                  30

Tyr Glu Phe Ile Met Lys Asn Phe Pro Tyr Tyr Arg Glu Asn Lys Gln
                 35                  40                  45

Gly Trp Gln Asn Ser Ile Arg His Asn Leu Ser Leu Asn Lys Cys Phe
 50                  55                  60

Val Lys Val Pro Arg His Tyr Asp Asp Pro Gly Lys Gly Asn Tyr Trp
 65                  70                  75                  80

Met Leu Asp Pro Ser Ser Asp Asp Val Phe Ile Gly Gly Thr Thr Gly
                 85                  90                  95
```

```
Lys Leu Arg Arg Ser Thr Thr Ser Pro Ala
            100                 105
```

(2) INFORMATION FOR SEQ ID NO:18:

(i) SEQUENCE CHARACTERISTICS:
       (A) LENGTH: 106 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:18:

```
Gly Lys Tyr Glu Lys Pro Pro Phe Ser Tyr Asn Ala Leu Ile Met
1               5                   10                  15

Met Ala Ile Arg Gln Ser Pro Glu Lys Arg Leu Thr Leu Asn Gly Ile
            20                  25                  30

Tyr Glu Phe Ile Met Lys Asn Phe Pro Tyr Tyr Arg Glu Asn Lys Gln
            35                  40                  45

Gly Trp His Asn Ser Ile Arg Asp Asn Leu Ser Leu Asn Lys Cys Phe
            50                  55                  60

Val Lys Val Pro Arg His Tyr Asp Asp Pro Gly Lys Gly Asn Tyr Trp
65                  70                  75                  80

Met Leu Asp Pro Ser Ser Asp Asp Val Phe Ile Gly Gly Thr Thr Gly
                85                  90                  95

Lys Leu Arg Arg Arg Ser Thr Thr Ser Arg
            100                 105
```

(2) INFORMATION FOR SEQ ID NO:19:

(i) SEQUENCE CHARACTERISTICS:
       (A) LENGTH: 76 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:19:

```
Leu Met Lys Leu Val Arg Pro Pro Tyr Ser Tyr Ser Ala Leu Ile Ala
1               5                   10                  15

Met Ala Ile His Gly Ala Pro Asp Lys Arg Leu Thr Leu Ser Gln Ile
            20                  25                  30

Tyr Gln Tyr Val Ala Asp Asn Phe Pro Phe Tyr Asn Lys Ser Lys Ala
            35                  40                  45

Gly Trp Gln Asn Ser Ile Arg His Asn Leu Ser Leu Asn Asp Cys Phe
            50                  55                  60

Lys Lys Val Pro Arg Asp Glu Asp Asp Pro Gly Lys
65                  70                  75
```

(2) INFORMATION FOR SEQ ID NO:20:

(i) SEQUENCE CHARACTERISTICS:
       (A) LENGTH: 106 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:20:

```
Thr Asn Pro His Val Lys Pro Pro Tyr Ser Tyr Ala Thr Leu Ile Cys
```

-continued

```
 1               5                   10                  15
Met Ala Met Gln Ala Ser Lys Ala Thr Lys Ile Tyr Leu Ser Ala Ile
                20                  25              30

Tyr Lys Trp Ile Thr Asp Asn Phe Cys Tyr Phe Arg His Ala Asp Pro
            35              40              45

Thr Trp Gln Asn Ser Ile Arg His Asn Leu Ser Leu Asn Lys Cys Phe
        50              55              60

Ile Lys Val Pro Arg Glu Lys Asp Glu Pro Gly Lys Gly Gly Phe Trp
65                  70              75                      80

Arg Ile Asp Pro Gln Tyr Ala Glu Arg Leu Leu Ser Gly Ala Phe Lys
                85              90              95

Lys Arg Arg Leu Pro Phe Val His Ile His
            100             105
```

(2) INFORMATION FOR SEQ ID NO:21:

(i) SEQUENCE CHARACTERISTICS:
        (A) LENGTH: 99 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:21:

```
Trp Gly Asn Leu Ser Tyr Ala Asp Leu Ile Thr Lys Ala Ile Glu Ser
1               5                   10                  15

Ser Ala Glu Lys Arg Leu Thr Leu Ser Gln Ile Tyr Glu Trp Met Val
                20                  25              30

Lys Ser Val Pro Tyr Phe Lys Asp Lys Gly Asp Ser Asn Ser Ser Ala
            35              40              45

Gly Trp Lys Asn Ser Ile Arg His Asn Leu Ser Leu His Ser Lys Phe
        50              55              60

Ile Arg Val Gln Asn Glu Gly Thr Gly Lys Ser Ser Trp Trp Met Leu
65                  70              75                      80

Asn Pro Glu Gly Gly Lys Ser Cys Lys Ser Pro Arg Arg Arg Ala Ala
                85              90              95

Ser Met Asp
```

(2) INFORMATION FOR SEQ ID NO:22:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

```
Arg Thr Ala Ala Tyr Ala
1               5
```

THERAPEUTICS AND DIAGNOSTICS FOR CONGENITAL HEART DISEASE BASED ON A NOVEL HUMAN TRANSCRIPTION FACTOR

This application claims priority to provisional patent application 60/081,870, filed Apr. 15, 1998.

GOVERNMENT FUNDING

This invention was partially funded by NIH Grant No. RO1-EY-10564; the government, therefore, has certain rights to the invention.

1. BACKGROUND OF THE INVENTION

"Congenital heart disease" refers to defects in the heart and major great vessels produced by abnormalities at various stages of fetal development and present at birth, but which may not be diagnosed until later. The incidence of such anomalies is 1/120 live births (The Merck Manual of Diagnosis and Therapy, $16^{th}$ Ed. (1992) p. 2051). "Atrial septal defect" is form of congenital heart disease in which there is an opening in the septum that normally separates the atria. The typical murmur of atrial septal defect is usually present after age 1 yr., when pulmonary blood flow has increased significantly.

Many congenital heart diseases have a genetic basis. However, surgery offers the only therapeutic option for many of these disorders. In addition, current identification and diagnosis of congenital heart disease depends on the recognition of affected cardiac function, such as heart murmurs representing turbulent flow, altered systemic and pulmonary blood flow, shunting in either direction, and evidences of altered work load of the cardiac chambers. Routine history, physical examination, ECG, and chest x-ray are usually performed for specific anatomic diagnosis, with supportive and confirmatory data from echocardiography, cardiac catheterization, angiocardiography and other laboratory data.

Improved therapies and diagnostics for genetically based congenital heart diseases are needed.

2. SUMMARY OF THE INVENTION

The present invention is based, at least in part, on the discovery of a novel human gene, which encodes a novel human protein. These newly identified genes and proteins are referred to herein as "FKHL7". FKHL7 is a monomeric DNA binding protein that shares a core binding site (RTAAAYA; SEQ ID NO:22) with four other FKHL7-like proteins. In addition, the forkhead domain of this protein shows strong homology to the human gene, FKHL14 and the mouse genes, Fkh1 and Fkh14, by BLASTN analysis.

A 9.8 kb subclone of BAC471g19 was partially sequenced and determined to contain the entire coding region of FKHL7 as well as 5' and 3' untranslated sequences (SEQ ID NO. 1). The human FKHL7 coding sequence is 1.7 kb in size and contains no introns. The 1659 bp open reading frame (SEQ ID NO. 3) encodes a 553 amino acid polypeptide (SEQ ID NO. 2). The COOH-terminal domain contains several stretches of homopolymeric runs of alanine and glycine. The FKHL7 coding region contains 5 recognition sites for the restriction enzyme NotI. A BLASTN screen of the public dbEST database with the FKHL7 genomic sequence yields only partial human and mouse cDNA coverage of this gene. Based on the analysis of cDNA clones identified in the public databases, there is evidence for the utilization of at least two different polyadenylation signals within the 3' untranslated region.

Human FKHL7 is most abundantly expressed during embryogenesis and of the adult tissue tested, significant expression was observed in adult eye, heart, kidney and lung, while relatively little to no expression was observed in adult skeletal muscle, spleen or liver.

In one aspect, the invention features isolated FKHL7 nucleic acid molecules. In one embodiment, the FKHL7 nucleic acid is from a vertebrate. In a preferred embodiment, the FKHL7 nucleic acid is from a mammal, e.g. a human. In an even more preferred embodiment, the nucleic acid has the nucleic acid sequence set forth in SEQ ID NO. 1 or 3 or a portion thereof The disclosed molecules can be non-coding, (e.g. a probe, antisense, or ribozyme molecule) or can encode a functional FKHL7 polypeptide (e.g. a polypeptide which functions as either an agonist or antagonist of at least one bioactivity of the human FKHL7 polypeptide). In one embodiment, the nucleic acid of the present invention can hybridize to a vertebrate FKHL7 gene or to the complement of a vertebrate FKHL7 gene. In a further embodiment, the claimed nucleic acid can hybridize with a nucleic acid sequence shown in FIG. 1 (SEQ ID NOS. 1 and 3) or a complement thereof. In a preferred embodiment, the hybridization is conducted under mildly stringent or stringent conditions.

In further embodiments, the nucleic acid molecule is an FKHL7 nucleic acid that is at least about 70%, preferably about 80%, more preferably about 85%, and even more preferably at least about 90% or 95% homologous to the nucleic acid shown as SEQ ID NOS: 1 or 3 or to the complement of the nucleic acid shown as SEQ ID NOS: 1 or 3.

The invention also provides probes and primers comprising substantially purified oligonucleotides, which correspond to a region of nucleotide sequence which hybridizes to at least about 6, at least about 10, at least about 15, at least about 20, or preferably at least about 25 consecutive nucleotides of the sequence set forth as SEQ ID NO. 1 or SEQ ID NO. 3 or complements of the sequence set forth as SEQ ID NOS. 1 or 3 or naturally occurring mutants or allelic variants thereof In preferred embodiments, the probe/primer further includes a label group attached thereto, which is capable of being detected.

For expression, the subject nucleic acids can be operably linked to a transcriptional regulatory sequence, e.g., at least one of a transcriptional promoter (e.g., for constitutive expression or inducible expression) or transcriptional enhancer sequence. Such regulatory sequences in conjunction with an FKHL7 nucleic acid molecule can provide a useful vector for gene expression. This invention also describes host cells transfected with said expression vector whether prokaryotic or eukaryotic and in vitro (e.g. cell culture) and in vivo (e.g. transgenic) methods for producing FKHL7 proteins by employing said expression vectors.

In another aspect, the invention features isolated FKHL7 polypeptides, preferably substantially pure preparations, e.g. of plasma purified or recombinantly produced polypeptides. The FKHL7 polypeptide can comprise a full length protein or can comprise smaller fragments corresponding to one or more particular motifs/domains, or fragments comprising at least about 5, 10, 25, 50, 75, 100, 125, 150, 175, 200, 225, 250, 275, 300, 325, 350, 375, 400, 425, 450, 475, 500, 510, 520, 530 or 540 amino acids in length. In particularly preferred embodiments, the subject polypeptide is capable of binding to an upstream region of a gene and/or otherwise regulating expression of a gene.

In a preferred embodiment, the polypeptide is encoded by a nucleic acid, which hybridizes with the nucleic acid sequence represented in SEQ ID NOS. 1 or 3. In a further preferred embodiment, the FKHL7 polypeptide is comprised of the amino acid sequence set forth in SEQ ID NO. 2. The subject FKHL7 protein also includes within its scope modified proteins, e.g. proteins which are resistant to post-translational modification, for example, due to mutations which alter modification sites (such as tyrosine, threonine, serine or asparagine residues), or which prevent glycosylation of the protein, or which prevent interaction of the protein with intracellular proteins involved in signal transduction.

The FKHL7 polypeptides of the present invention can be glycosylated, or conversely, by choice of the expression system or by modification of the protein sequence to preclude glycosylation, reduced carbohydrate analogs can also be provided. Glycosylated forms can be obtained, for example, based on derivatization with glycosaminoglycan chains.

In yet another preferred embodiment, the invention features a purified or recombinant polypeptide, which has the ability to modulate, e.g., mimic or antagonize, an activity of a wild-type FKHL7 protein. Preferably, the polypeptide comprises an amino acid sequence identical or homologous to a sequence designated in SEQ ID NO. 2.

Another aspect of the invention features chimeric molecules (e.g., fusion proteins) comprising an FKHL7 protein. For instance, the FKHL7 protein can be provided as a recombinant fusion protein which includes a second polypeptide portion, e.g., a second polypeptide having an amino acid sequence unrelated (heterologous) to the FKHL7 polypeptide. A preferred FKHL7 fusion protein is an immunoglobulin-FKHL7 fusion protein, in which an immunoglobulin constant region is fused to an FKHL7 polypeptide.

Yet another aspect of the present invention concerns an immunogen comprising an FKHL7 polypeptide in an immunogenic preparation, the immunogen being capable of eliciting an immune response specific for an FKHL7 polypeptide; e.g. a humoral response, an antibody response and/or cellular response. In a preferred embodiment, the immunogen comprises an antigenic determinant, e.g. a unique determinant of a protein encoded by the nucleic acid set forth in SEQ ID NO. 1 or 3; or as set forth in SEQ ID NO. 2.

A still further aspect of the present invention features antibodies and other binding proteins or peptides that are specifically reactive with an epitope of an FKHL7 protein.

The invention also features transgenic non-human animals which include (and preferably express) a heterologous form of an FKHL7 gene described herein, or which misexpress an endogenous FKHL7 gene (e.g., an animal in which expression of one or more of the subject FKHL7 proteins is disrupted). Such transgenic animals can serve as animal models for studying cellular and/or tissue disorders comprising mutated or mis-expressed FKHL7 alleles or for use in drug screening. Alternatively, such transgenic animals can be useful for expressing recombinant FKHL7 polypeptides.

The invention further features assays and kits for determining whether an individual's FKHL7 genes and/or proteins are defective or deficient (e.g in activity and/or level), and/or for determining the identity of FKHL7 alleles. In one embodiment, the method comprises the step of determining the level of FKHL7 protein, the level of FKHL7 mRNA and/or the transcription rate of an FKHL7 gene. In another preferred embodiment, the method comprises detecting, in a tissue of the subject, the presence or absence of a genetic alteration, which is characterized by at least one of the following: a deletion of one or more nucleotides from a gene; an addition of one or more nucleotides to the gene; a substitution of one or more nucleotides of the gene; a gross chromosomal rearrangement of the gene; an alteration in the level of a messenger RNA transcript of the gene; the presence of a non-wild type splicing pattern of a messenger RNA transcript of the gene; and/or a non-wild type level of the FKHL7 protein.

FKHL7 mutations that are particularly likely to cause or contribute to the development of congenital heart disease include mutations that result in an FKHL7 protein that lacks or contains a substantially impaired FKHL7 gene.

FKHL7 mutations can be detected by: i) providing a probe/primer comprised of an oligonucleotide which hybridizes to a sense or antisense sequence of an FKHL7 gene or naturally occurring mutants thereof, or 5' or 3' flanking sequences naturally associated with the FKHL7 gene; (ii) contacting the probe/primer with an appropriate nucleic acid containing sample; and (iii) detecting, by hybridization of the probe/primer to the nucleic acid, the presence or absence of the genetic alteration. Particularly preferred embodiments comprise: 1) sequencing at least a portion of an FKHL7 gene, 2) performing a single strand conformation polymorphism (SSCP) analysis to detect differences in electrophoretic mobility between mutant and wild-type nucleic acids; and 3) detecting or quantitating the level of an FKHL7 protein in an immunoassay using an antibody which is specifically immunoreactive with a wild-type or mutated FKHL7 protein.

Information obtained using the diagnostic assays described herein (alone or in conjunction with information on another genetic defect, which contributes to the same disease) is useful for diagnosing or confirming that a symptomatic subject has a genetic defect (e.g. in an FKHL7 gene or in a gene that regulates the expression of an FKHL7 gene), which causes or contributes to the particular disease or disorder. Alternatively, the information (alone or in conjunction with information on another genetic defect, which contributes to the same disease) can be used prognostically for predicting whether a non-symptomatic subject is likely to develop a disease or condition, which is caused by or contributed to by an abnormal FKHL7 activity or protein level in a subject. In particular, the assays permit one to ascertain an individual's predilection to develop a condition associated with a mutation in FKHL7, where the mutation is a single nucleotide polymorphism (SNP). Based on the prognostic information, a doctor can recommend a regimen (e.g. diet or exercise) or therapeutic protocol useful for preventing or prolonging onset of a congenital heart disease in the individual.

In addition, knowledge of the particular alteration or alterations, resulting in defective or deficient FKHL7 genes or proteins in an individual, alone or in conjunction with information on other genetic defects contributing to the same disease (the genetic profile of the particular disease) allows customization of therapy to the individual's genetic profile, the goal of pharmacogenomics. For example, an individual's FKHL7 genetic profile or the genetic profile of the congenital heart disease can enable a doctor to: 1) more effectively prescribe a drug that will address the molecular basis of glaucoma; and 2) better determine the appropriate dosage of a particular drug. For example, the expression level of FKHL7 proteins, alone or in conjunction with the expression level of other genes known to be involved in glaucoma, can be measured in many patients at various stages of the disease to generate a transcriptional or expression profile of the congenital heart disease. Expression patterns of individual patients can then be compared to the expression profile of the congenital heart disease to determine the appropriate drug and dose to administer to the patient.

The ability to target populations expected to show the highest clinical benefit, based on the FKHL7 or congenital heart disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since the use of FKHL7 as a marker is useful for optimizing effective dose).

In another aspect, the invention provides methods for identifying a compound which modulates an FKHL7 activity, e.g. the interaction between an FKHL7 polypeptide and a target peptide In a preferred embodiment, the method includes the steps of (a) forming a reaction mixture, which includes: (i) an FKHL7 polypeptide, (ii) an FKHL7 binding partner and (iii) a test compound; and (b) detecting interaction of the FKHL7 polypeptide and the FKHL7 binding partner. A statistically significant change (potentiation or inhibition) in the interaction of the FKHL7 polypeptide and FKHL7 binding partner in the presence of the test compound, relative to the interaction in the absence of the test compound, indicates a potential agonist (mimetic or potentiator) or antagonist (inhibitor) of FKHL7 bioactivity for the test compound. The reaction mixture can be a cell-free protein preparation, e.g., a reconstituted protein mixture or a cell lysate, or it can be a recombinant cell including a heterologous nucleic acid recombinantly expressing the FKHL7 binding partner.

In preferred embodiments, the step of detecting interaction of the FKHL7 and FKHL7 binding partner is a competitive binding assay. In other preferred embodiments, at least one of the FKHL7 polypeptide and the FKHL7 binding partner comprises a detectable label, and interaction of the FKHL7 and FKHL7 binding partner is quantified by detecting the label in the complex. The detectable label can be, e.g., a radioisotope, a fluorescent compound, an enzyme, or an enzyme co-factor. In other embodiments, the complex is detected by an immunoassay.

Yet another exemplary embodiment provides an assay for screening test compounds to identify agents which modulate the amount of FKHL7 produced by a cell. In one embodiment, the screening assay comprises contacting a cell transfected with a reporter gene operably linked to an FKHL7 promoter with a test compound and determining the level of expression of the reporter gene. The reporter gene can encode, e.g., a gene product that gives rise to a detectable signal such as: color, fluorescence, luminescence, cell viability, relief of a cell nutritional requirement, cell growth, and drug resistance. For example, the reporter gene can encode a gene product selected from the group consisting of chloramphenicol acetyl transferase, luciferase, beta-galactosidase and alkaline phosphatase.

Also within the scope of the invention are methods for treating a congenital heart disease, comprising administering (e.g., either locally or systemically) to a subject, a pharmaceutically effective amount of a composition comprising an FKHL7 therapeutic.

Other features and advantages of the invention will be apparent from the following detailed description and claims.

3. BRIEF DESCRIPTION OF THE FIGURES

FIGS. 1A–1B is a DNA sequence of the human FKHL7 gene including the 5' and 3' untranslated regions (UTRs) (SEQ. ID. No. 1). The 1659 base pair open reading frame is provided herein as SEQ ID NO. 3 and the (SEQ ID NO. 3) 553 amino acid human FKHL7 protein is provided herein as SEQ ID No. 2. The forkhead region of the protein is indicated by underline.

Figure 2:
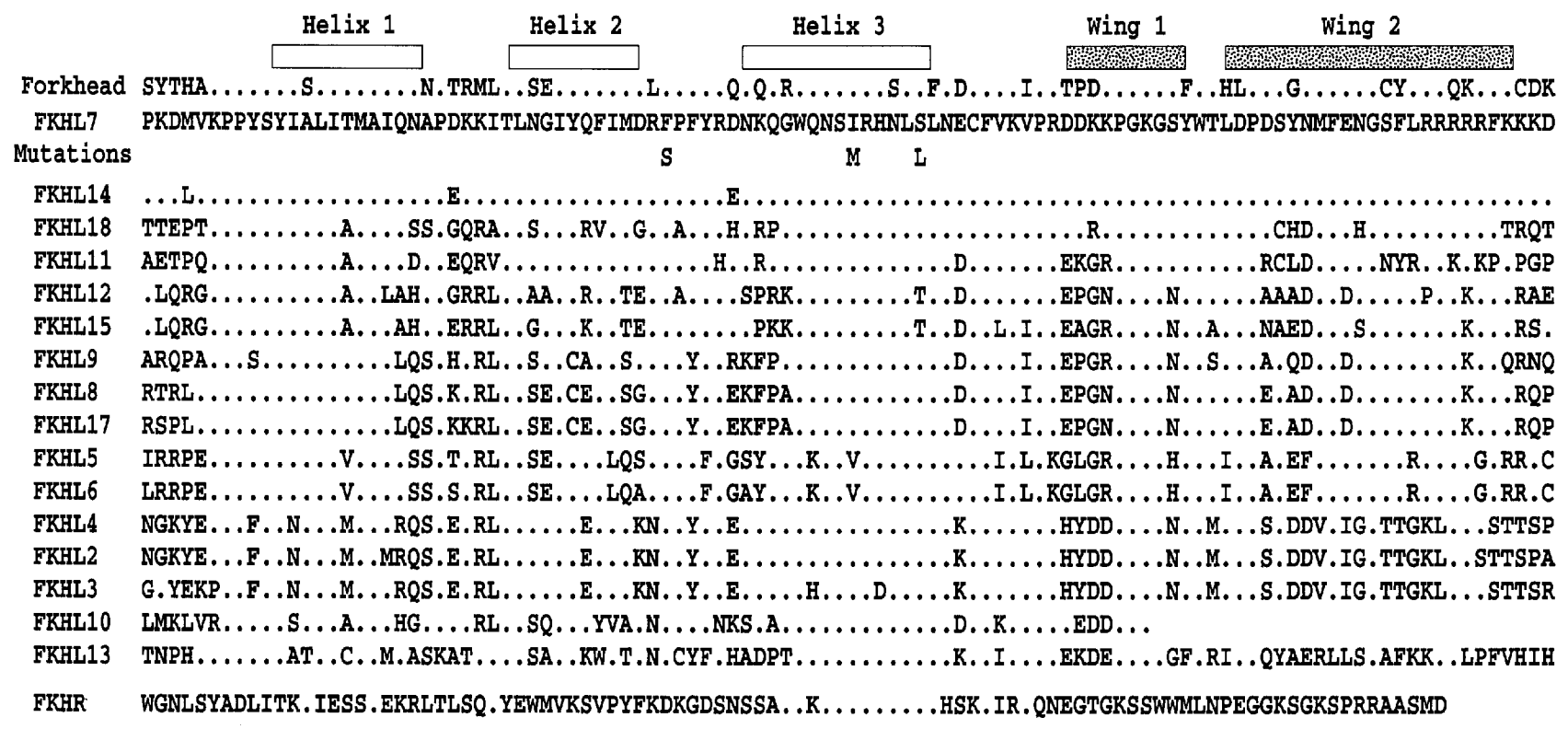

FIG. 2 shows an amino acid comparison of the forkhead domains of different members of the FKHL-family of genes corresponding to SEQ ID NOS:4–21, respectively. The locations of the three alpha helices and the two wing domains are shown (Clark, K. L. et al., Nature 364:412–420 (1993)). The Drosophila forkhead gene sequence is shown above that for FKHL7, while the positions of the three missense mutations are shown below FKHL7. Translation of the 11 base pair deletion (bp del) mutation results in total loss of the forkhead domain. The other FKHL family members are shown below FKHL7 for comparison. For FKHL10, only partial sequence is available for the forkhead domain. The last sequence shown is that for the distantly related FKHR which has been mapped to 13Q14 near the RIEG2 locus.

FIG. 3 provides the identity and location of Expressed Sequence Tags (ESTs) that map to regions of the human FKHL7 gene.

4. DETAILED DESCRIPTION OF THE INVENTION

4.1. General

The present invention is based, at least in part, on the discovery of a novel human gene, termed "hFKHL7" and the finding that defects in the gene result in the development of congenital heart disease. More particularly, a one base pair deletion upstream of the FKHL7 forkhead domain, resulting in a truncated protein that lacks the forkhead domain was found in two individuals from a nuclear family. The proband was found to have Rieger anomaly similar to other patients as well as an atrial septal defect. His mother has Rieger anomaly. Both individuals were found to harbor this mutation. However, the mutation was not found in 128 normal Caucasian individuals. In addition, as shown in the following FIG. 3, of the 26 human ESTs identified in a BLASTN search, 5 were found to be derived from a fetal heart library and 2 were from an aorta cDNA library. Furthermore, an additional 4 ESTs were from a pooled library of three tissues (melanocytes, uterus and fetal heart). The fact that such a large proportion of the ESTs are derived from heart further supports the finding that mutations in the gene can result in congenital heart defects. Expression of FKHL7 by Northern blot analysis has been confirmed in human and mouse heart.

hFKHL7 maps to human chromosome 6p25. The FKHL7 protein is a monomeric DNA binding protein that shares a core binding site (RTAAAYA; SEQ ID NO: 22) with four other FKHL7-like proteins. The human FKHL7 coding sequence is 1.7 kb in size and contains no introns. The 1659 bp open reading frame (SEQ ID NO. 3) encodes a 553 amino acid polypeptide (SEQ ID NO. 2). The first in-frame ATG was found to match well with the Kozak consensus sequence (Kozak, M. *Mamm. Genome* 7: 5630574 (1996) and Kozak, M. *Annu. Rev. Cell. Biol.* 8: 197–225 (1992)). The COOH-terminal domain contains several stretches of homopolymeric runs of alanine and glycine. The FKHL7 coding region contains 5 recognition sites for the restriction enzyme NotI. A BLASTN screen of the public dbEST database with the FKHL7 genomic sequence yields only partial human and mouse cDNA coverage of this gene (SEE FIG. 1). Based on the analysis of cDNA clones identified in the public databases, there is evidence for the utilization of at least two different polyadenylation signals within the 3' untranslated region.

Human FKHL7 is most abundantly expressed during embryogenesis and of the adult tissues tested, significant expression was observed in adult eye, heart, kidney and lung, while relatively little to no expression was observed in adult skeletal muscle, spleen or liver.

4.2 Definitions

For convenience, the meaning of certain terms and phrases employed in the specification, examples, and appended claims are provided below.

The term "agonist", as used herein, is meant to refer to an agent that mimics or upregulates (e.g. potentiates or supplements) an FKHL7 bioactivity. An FKHL7 agonist can be a wild-type FKHL7 protein or derivative thereof having at least one bioactivity of the wild-type FKHL7. An FKHL7 therapeutic can also be a compound that upregulates expression of an FKHL7 gene or which increases at least one bioactivity of an FKHL7 protein. An agonist can also be a compound which increases the interaction of an FKHL7 polypeptide with another molecule, e.g., an upstream region of a gene, which is regulated by an FKHL7 transcription factor.

"Antagonist" as used herein is meant to refer to an agent that downregulates (e.g. suppresses or inhibits) at least one FKHL7 bioactivity. An FKHL7 antagonist can be a compound which inhibits or decreases the interaction between an FKHL7 protein and another molecule, e.g, an upstream region of a gene, which is regulated by an FKHL7 transcription factor. Accordingly, a preferred antagonist is a compound which inhibits or decreases binding to an upstream region of a gene, which is regulated by an FKHL7 transcription factor and thereby blocks subsequent activation of the FKHL7. An antagonist can also be a compound that downregulates expression of an FKHL7 gene or which reduces the amount of FKHL7 protein present. The FKHL7 antagonist can be a dominant negative form of an FKHL7 polypeptide, e.g., a form of an FKHL7 polypeptide which is capable of interacting with an upstream region of a gene, which is regulated by an FKHL7 transcription factor, but which is not capable of regulating transcription. The FKHL7 antagonist can also be a nucleic acid encoding a dominant negative form of an FKHL7 polypeptide, an FKHL7 antisense nucleic acid, or a ribozyme capable of interacting specifically with an FKHL7 RNA. Yet other FKHL7 antagonists are molecules which bind to an FKHL7 polypeptide and inhibit its action. Such molecules include peptides, antibodies and small molecules.

The term "allele", which is used interchangeably herein with "allelic variant" refers to alternative forms of a gene or portions thereof Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation. The term "allelic variant of a polymorphic region of an FKHL7 gene" refers to a region of an FKHL7 gene having one or several nucleotide sequences found in that region of the gene in other individuals.

"Biological activity" or "bioactivity" or "activity" or "biological function", which are used interchangeably, for the purposes herein means an effector or antigenic function that is directly or indirectly performed by an FKHL7 polypeptide (whether in its native or denatured conformation), or by any subsequence thereof Biological activities include binding to a target nucleic acid e.g., an upstream region of a gene, which is regulated by an FKHL7 transcription factor. An FKHL7 bioactivity can be modulated by directly affecting an FKHL7 polypeptide. Alternatively, an FKHL7 bioactivity can be modulated by modulating the level of an FKHL7 polypeptide, such as by modulating expression of an FKHL7 gene.

As used herein the term "bioactive fragment of an FKHL7 polypeptide" refers to a fragment of a full-length FKHL7 polypeptide, wherein the fragment specifically mimics or antagonizes the activity of a wild-type FKHL7 polypeptide. The bioactive fragment preferably is a fragment capable of interacting with e.g, an upstream region of a gene, which is regulated by an FKHL7 transcription factor.

The term "an aberrant activity", as applied to an activity of a polypeptide such as FKHL7, refers to an activity which differs from the activity of the wild-type or native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in an activity. For example an aberrant polypeptide can interact with a different target peptide. A cell can have an aberrant FKHL7 activity due to overexpression or underexpression of the gene encoding FKHL7.

"Cells", "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric polypeptide" or "fusion polypeptide" is a fuision of a first amino acid sequence encoding one of the subject FKHL7 polypeptides with a second amino acid sequence defining a domain (e.g. polypeptide portion) foreign to and not substantially homologous with any domain of an FKHL7 polypeptide. A chimeric polypeptide may present a foreign domain which is found (albeit in a different polypeptide) in an organism which also expresses the first polypeptide, or it may be an "interspecies", "intergenic", etc. fusion of polypeptide structures expressed by different kinds of organisms. In general, a fusion polypeptide can be represented by the general formula X-FKHL7Y, wherein FKHL7 represents a portion of the polypeptide which is derived from an FKHL7 polypeptide, and X and Y are independently absent or represent amino acid sequences which are not related to an FKHL7 sequence in an organism, including naturally occurring mutants.

"Congenital heart disease" refers to defects in the heart and major great vessels produced by abnormalities at various stages of fetal development and present at birth, but which may not be diagnosed until later. Examples include: ventricular septal defect, atrial septal defect, patent ductus arteriosus, atrioventricular canal defects, congential aortic valve stenosis, pulmonic valve stenosis, peripheral pulmonic stenosis, coarctation of the aorta, tetralogy of fallot, transposition of the great arteries, complex cyanotic congenital heart disease and underdeveloped left ventricle syndrome.

The term "nucleotide sequence complementary to the nucleotide sequence set forth in SEQ ID NO. x" refers to the nucleotide sequence of the complementary strand of a nucleic acid strand having SEQ ID NO. x. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID NO. x refers to the complementary strand of the strand having SEQ ID NO. x or to any nucleic acid having the nucleotide sequence of the complementary strand of SEQ ID NO. x. When referring to a single stranded nucleic acid having the nucleotide sequence SEQ ID NO. x, the complement of this nucleic acid is a nucleic acid having a nucleotide sequence which is complementary to that of SEQ ID NO. x. The nucleotide sequences and complementary sequences thereof are always given in the 5' to 3' direction.

A "delivery complex" shall mean a targeting means (e.g. a molecule that results in higher affinity binding of a gene, protein, polypeptide or peptide to a target cell surface and/or increased cellular or nuclear uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding an FKHL7 polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide, yet still encode a polypeptide with the same biological activity.

The term "FKHL7 nucleic acid" refers to a nucleic acid encoding an FKHL7 protein, such as nucleic acids having SEQ ID NOS. 1 or 3, as well as fragments thereof, complements thereof, and derivatives thereof.

The terms "FKHL7 polypeptide" and "FKHL7 protein" are intended to encompass polypeptides comprising the amino acid sequence shown as SEQ ID NO. 2 or fragments thereof, and homologs thereof and include agonist and antagonist polypeptides.

The term "FKHL7 therapeutic" refers to various forms of FKHL7 polypeptides, as well as peptidomimetics, nucleic acids, or small molecules, which can modulate at least one activity of an FKHL7 polypeptide, e.g., binding to and/or otherwise regulating expression of a gene, by mimicking or potentiating (agonizing) or inhibiting (antagonizing) the effects of a naturally-occurring FKHL7 polypeptide. An FKHL7 therapeutic which mmics or potentiates the activity of a wild-type FKHL7 polypeptide is a "FKHL7 agonist". Conversely, an FKHL7 therapeutic which inhibits the activity of a wild-type FKHL7 polypeptide is a "FKHL7 antagonist".

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. An "unrelated" or "non-homologous" sequence shares less than about 40% identity, though preferably less than about 25% identity, with one of the FKHL7 sequences of the present invention.

The term "interact" as used herein is meant to include detectable relationships or associations (e.g. biochemical interactions) between molecules, such as interaction between protein—protein, protein-nucleic acid, nucleic acid-nucleic acid, and protein-small molecule or nucleic acid-small molecule in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject FKHL7 polypeptides preferably includes no more than about 10 kilobases (kb) of nucleic acid sequence which naturally immediately flanks the FKHL7 gene in genomic DNA, more preferably no more than about 5 kb of such naturally occurring flanking sequences, and most preferably less than about 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "modulation" as used herein refers to both upregulation (i.e., activation or stimulation (e.g., by agonizing or potentiating)) and downregulation (i.e. inhibition or suppression (e.g., by antagonizing, decreasing or inhibiting)).

The term "mutated gene" refers to an allelic form of a gene, which is capable of altering the phenotype of a subject having the mutated gene relative to a subject which does not have the mutated gene. Ifa subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous subject (for that gene), the mutation is said to be co-dominant.

The "non-human animals" of the invention include mammals such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant gene is expressed in some but not all cells of the animal. The term "tissue-specific chimeric animal" indicates that one of the recombinant FKHL7 genes is present and/or expressed or disrupted in some tissues but not others.

As used herein, the term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs and as applicable to the embodiment being described, single (sense or antisense) and double-stranded polynucleotides.

The term "polymorphism" refers to the coexistence of more than one form of a gene or portion (e.g., allelic variant) thereof A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long.

A "polymorphic gene" refers to a gene having at least one polymorphic region.

As used herein, the term "promoter" refers to a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to a gene product.

The term "recombinant protein" refers to a polypeptide of the present invention which is produced by recombinant DNA techniques, wherein generally, DNA encoding an FKHL7 polypeptide is inserted into a suitable expression vector which is in turn used to transform a host cell to produce the heterologous protein. Moreover, the phrase "derived from", with respect to a recombinant FKHL7 gene, is meant to include within the meaning of "recombinant protein" those proteins having an amino acid sequence of a native FKHL7 polypeptide, or an amino acid sequence similar thereto which is generated by mutations including substitutions and deletions (including truncation) of a naturally occurring form of the polypeptide.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention to identify compounds that modulate an FKHL7 bioactivity.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400, 425, 450, 475 or 500 consecutive nucleotides of a vertebrate gene, preferably an FKHL7 gene.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the FKHL7 genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of a FKHL7 polypeptide.

As used herein, the term "transfection" means the introduction of a nucleic acid, e.g., via an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of an FKHL7 polypeptide or, in the case of anti-sense expression from the transferred gene, the expression of a naturally-occurring form of the FKHL7 polypeptide is disrupted.

As used herein, the term "transgene" means a nucleic acid sequence (encoding, e.g., one of the FKHL7 polypeptides, or an antisense transcript thereto) which has been introduced into a cell. A transgene could be partly or entirely heterologous, i.e., foreign, to the transgenic animal or cell into which it is introduced, or, can be homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the FKHL7 polypeptides, e.g. either agonistic or antagonistic forms. However, transgenic animals in which the recombinant FKHL7 gene is silent are also contemplated, as for example, the FLP or CRE recombinase dependent constructs described below. Moreover, "transgenic animal" also includes those recombinant animals in which gene disruption of one or more FKHL7 genes is caused by human intervention, including both recombination and antisense techniques.

The term "treating" as used herein is intended to encompass curing as well as ameliorating at least one symptom of the condition or disease.

The term "vector" refers to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

4.3. Nucleic Acids of the Present Invention

The invention provides FKHL7 nucleic acids, homologs thereof, and portions thereof. Preferred nucleic acids have a sequence, which is at least about 60%, 61%, 62%, 63%, 64%, 65%, 66%, 67%, 68%, 69%, 70%, 71%, 72%, 73%, 74%, 75%, 76%, 77%, 78%, 79%, 80%, and more preferably 85% homologous with a nucleotide sequence of an FKHL7 gene, e.g., such as a sequence shown in one of SEQ ID NOS: 1 or 3 or complements thereof. Nucleic acids at least 90%, more preferably 95%, and most preferably at least about 98–99% homologous with a nucleic sequence represented in one of SEQ ID NOS. 1 or 3 or a complement thereof are of course also within the scope of the invention.

The invention also pertains to isolated nucleic acids comprising a nucleotide sequence encoding FKHL7 polypeptides, variants and/or equivalents of such nucleic acids. The term equivalent is understood to include nucleotide sequences encoding functionally equivalent FKHL7 polypeptides or functionally equivalent peptides having an activity of an FKHL7 protein such as described herein. Equivalent nucleotide sequences will include sequences that differ by one or more nucleotide substitutions, additions or deletions, such as allelic variants; and therefore includes sequences that differ from the nucleotide sequence of the FKHL7 gene shown in SEQ ID NOS. 1 or 3, due to the degeneracy of the genetic code.

Preferred nucleic acids are vertebrate FKHL7 nucleic acids. Particularly preferred vertebrate FKHL7 nucleic acids are mammalian. Regardless of species, particularly preferred FKHL7 nucleic acids encode polypeptides that are at least about 60%, 65%, 70%, 72%, 74%, 76%, 78%, 80%, 90%, or 95% similar or identical to an amino acid sequence of a vertebrate FKHL7 protein. In one embodiment, the nucleic acid is a cDNA encoding a polypeptide having at least one bio-activity of the subject FKHL7 polypeptide. Preferably, the nucleic acid includes all or a portion of the nucleotide sequence corresponding to the nucleic acid of SEQ ID NOS. 1 or 3.

Still other preferred nucleic acids of the present invention encode an FKHL7 polypeptide which is comprised of at least 50, 100, 150, 200, 250, 300, 350, 400, 450 or 500 amino acid residues. For example, such nucleic acids can comprise about 150, 300, 450, 600, 750, 900, 1050, 1200, 1350 or 1500 base pairs. Also within the scope of the invention are nucleic acid molecules for use as probes/primer or antisense molecules (i.e. noncoding nucleic acid molecules), which can comprise at least about 6, 12, 20, 30, 50, 60, 70, 80, 90 or 100 base pairs in length.

Another aspect of the invention provides a nucleic acid which hybridizes under stringent conditions to a nucleic acid represented by SEQ ID NOS. 1 or 3 or a complement thereof. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature and salt concentration may be held constant while the other variable is changed. In a preferred embodiment, an FKHL7 nucleic acid of the present invention will bind to one of SEQ ID NOS. 1 or 3 or complement thereof under moderately stringent conditions, for example at about 2.0×SSC and about 40° C. In a particularly preferred embodiment, an FKHL7 nucleic acid of the present invention will bind to one of SEQ ID NOS. 1 or 3 or a complement thereof under high stringency conditions.

Nucleic acids having a sequence that differs from the nucleotide sequences shown in one of SEQ ID NOS. 1 or 3 or a complement thereof due to degeneracy in the genetic code are also within the scope of the invention. Such nucleic acids encode functionally equivalent peptides (i.e., peptides having a biological activity of an FKHL7 polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of an FKHL7 polypeptide. However, it is expected that DNA sequence polymorphisms that do lead to changes in the amino acid sequences of the subject FKHL7 polypeptides will exist among mammals. One skilled in the art will appreciate that these variations in one or more nucleotides (e.g., up to about 3–5% of the nucleotides) of the nucleic acids encoding polypeptides having an activity of an FKHL7 polypeptide may exist among individuals of a given species due to natural allelic variation.

The polynucleotide of the present invention may also be fused in frame to a marker sequence, also referred to herein as "Tag sequence" encoding a "Tag peptide", which allows for marking and/or purification of the polypeptide of the present invention. In a preferred embodiment, the marker sequence is a hexahistidine tag, e.g., supplied by a PQE-9 vector. Numerous other Tag peptides are available commercially. Other frequently used Tags include myc-epitopes (e.g., see Ellison et al. (1991) *J Biol Chem* 266:21150–21157) which includes a 10-residue sequence from c-myc, the pFLAG system (International Biotechnologies, Inc.), the pEZZ-protein A system (Pharmacia, N.J.), and a 16 amino acid portion of the Haemophilus influenza hemagglutinin protein. Furthermore, any polypeptide can be used as a Tag so long as a reagent, e.g., an antibody interacting specifically with the Tag polypeptide is available or can be prepared or identified.

In another embodiment, a fusion gene coding for a purification leader sequence, such as a poly-(His)/ enterokinase cleavage site sequence at the N-terminus of the desired portion of the recombinant protein, can allow purification of the expressed fusion protein by affinity chromatography using a $Ni^{2+}$ metal resin. The purification leader sequence can then be subsequently removed by treatment with enterokinase to provide the purified protein (e.g., see Hochuli et al. (1987) J. Chromatography 411:177; and Janknecht et al. PNAS 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al. John Wiley & Sons: 1992).

Other preferred FKHL7 fusion proteins include FKHL7-immunoglobuhin (FKHL7-Ig) polypeptides. An FKHL7-Ig polypeptide can comprise the entire extracellular domain of FKHL7, e.g, human FKHL7, or a variant thereof For example, an FKHL7-Ig fusion proteins can be prepared as described e.g., in U.S. Pat. No. 5,434,131.

As indicated by the examples set out below, FKHL7 protein-encoding nucleic acids can be obtained from mRNA present in any of a number of eukaryotic cells, e.g., from cardiac tissue. It should also be possible to obtain nucleic acids encoding FKHL7 polypeptides of the present invention from genomic DNA from both adults and embryos. For example, a gene encoding an FKHL7 protein can be cloned from either a cDNA or a genomic library in accordance with protocols described herein, as well as those generally known to persons skilled in the art. cDNA encoding an FKHL7 protein can be obtained by isolating total mRNA from a cell, e.g., a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding an FKHL7 protein can also be cloned using established polymerase chain reaction techniques in accordance with the nucleotide sequence information provided by the invention. The nucleic acid of the invention can be DNA or RNA or analogs thereof. A preferred nucleic acid is a cDNA represented by a sequence selected from the group consisting of SEQ ID NOS. 1 or 3.

Preferred nucleic acids encode a vertebrate FKHL7 polypeptide comprising an amino acid sequence that is at least about 60% homologous, more preferably at least about 70% homologous and most preferably at least about 80% homologous with an amino acid sequence contained in SEQ ID NO. 2. Nucleic acids which encode polypeptides with at least about 90%, more preferably at least about 95%, and most preferably at least about 98–99% homology with an amino acid sequence represented in SEQ ID NO. 2 are also within the scope of the invention. In one embodiment, the nucleic acid is a cDNA encoding a peptide having at least one activity of the subject vertebrate FKHL7 polypeptide. Preferably, the nucleic acid includes all or a portion of the nucleotide sequence corresponding to the coding region of SEQ ID NOS. 1 or 3.

Preferred nucleic acids encode a bioactive fragment of a vertebrate FKHL7 polypeptide comprising an amino acid sequence, which is at least about 60% homologous or identical, more preferably at least about 70% homologous or identical, still more preferably at least about 75% homologous or identical and most preferably at least about 80% homologous or identical with an amino acid sequence of SEQ ID NO. 2. Nucleic acids which encode polypeptides which are at least about 90%, more preferably at least about 95%, and most preferably at least about 98–99% homologous or identical, with an amino acid sequence represented in SEQ ID NO. 2 are also within the scope of the invention.

Bioactive fragments of FKHL7 polypeptides can be polypeptides, which bind upstream of and/or regulate the expression of a gene. Assays for determining whether an FKHL7 polypeptide has any of these or other biological activities are known in the art and are further described herein.

Nucleic acids encoding modified forms or mutant forms of FKHL7 also include those encoding FKHL7 proteins having mutated glycosylation sites, such that either the encoded FKHL7 protein is not glycosylated, partially glycosylated and/or has a modified glycosylation pattern.

Other preferred nucleic acids of the invention include nucleic acids encoding derivatives of FKHL7 polypeptides which lack one or more biological activities of FKHL7 polypeptides. Such nucleic acids can be obtained, e.g., by a first round of screening of libraries for the presence or absence of a first activity and a second round of screening for the presence or absence of another activity.

Also within the scope of the invention are nucleic acids encoding splice variants or nucleic acids representing transcripts synthesized from an alternative transcriptional initiation site, such as those whose transcription was initiated from a site in an intron.

In preferred embodiments, the FKHL7 nucleic acids can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *PNAS* 93: 14670–675.

PNAs of FKHL7 can be used in therapeutic and diagnostic applications and are further described herein. Such modified nucleic acids can be used as antisense or antigene agents for sequence-specific modulation of gene expression or in the analysis of single base pair mutations in a gene by, e.g., PNA directed PCR clamping or as probes or primers for DNA sequence and hybridization (Hyrup B. et al (1996) supra; Perry-O'Keefe supra).

PNAs of FKHL7 can further be modified, e.g., to enhance their stability or cellular uptake, e.g., by attaching lipophilic or other helper groups to the FKHL7 PNA, by the formation of PNA—DNA chimeras, or by the use of liposomes or other techniques of drug delivery known in the art. FKHL7 PNAs can also be linked to DNA as described, e.g., in Hyrup B. (1996)supra and Finn P. J. et al. (1996) *Nucleic Acids Research* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used between the PNA and the 5' end of DNA (Mag, M. et al. (1989) *Nucleic Acid Res.* 17: 5973–88). PNA monomers are then coupled in a stepwise manner to produce a chimeric molecule with a 5'PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med Chem. Lett.* 5: 1119–11124).

In other embodiments, FKHL7 nucleic acids may include other appended groups such as peptides (e.g., for targeting host cell receptors in vivo), or agents that facilitate transport across the cell membrane as described herein.

4.3.1 Probes and Primers

The nucleotide sequences determined from the cloning of FKHL7 genes from mammalian organisms will further allow for the generation of probes and primers designed for use in identifying and/or cloning FKHL7 homologs in other cell types, e.g., from other tissues, as well as FKHL7 homologs from other mammalian organisms. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of sense or anti-sense sequence selected from the group consisting of SEQ ID NOS. 1 and 3 or naturally occurring mutants thereof. For instance, primers based on the nucleic acid represented in SEQ ID NOS. 1 or 3 can be used in PCR reactions to clone FKHL7 homologs.

Likewise, probes based on the subject FKHL7 sequences can be used to detect transcripts or genoric sequences encoding the same or homologous proteins, for use, e.g, in prognostic or diagnostic assays (further described below). In preferred embodiments, the probe further comprises a label group attached thereto and able to be detected, e.g., the label group is selected from amongst radioisotopes, fluorescent compounds, enzymes, and enzyme co-factors.

Probes and primers can be prepared and modified, e.g., as previously described herein for other types of nucleic acids.

4.3.2 Antisense, Ribozyme and Triplex Techniques

Another aspect of the invention relates to the use of the isolated nucleic acid in "antisense" therapy. As used herein, "antisense" therapy refers to administration or in situ generation of oligonucleotide molecules or their derivatives which specifically hybridize (e.g., bind) under cellular conditions, with the cellular mRNA and/or genomic DNA encoding one or more of the subject FKHL7 proteins so as to inhibit expression of that protein, e.g., by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes an FKHL7 protein. Alternatively, the antisense construct is an oligonucleotide probe which is generated ex vivo and which, when introduced into the cell causes inhibition of expression by hybridizing with the mRNA and/or genomic sequences of an FKHL7 gene. Such oligonucleotide probes are preferably modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphorothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958–976; and Stein et al. (1988) Cancer Res 48:2659–2668. With respect to antisense DNA, oligodeoxyribonucleotides derived from the translation initiation site, e.g., between the −10 and +10 regions of the FKHL7 nucleotide sequence of interest, are preferred.

Antisense approaches involve the design of oligonucleotides (either DNA or RNA) that are complementary to FKHL7 mRNA. The antisense oligonucleotides will bind to the FKHL7 mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. Nature 372:333). Therefore, oligonucleotides complementary to either the 5' or 3' untranslated, non-coding regions of an FKHL7 gene could be used in an antisense approach to inhibit translation of endogenous FKHL7 mRNA. Oligonucleotides complementary to the 5' untranslated region of the mRNA should include the complement of the AUG start codon. Antisense oligonucleotides complementary to mRNA coding regions are less efficient inhibitors of translation but could also be used in accordance with the invention. Whether designed to hybridize to the 5', 3' or coding region of FKHL7 mRNA, antisense nucleic acids should be at least six nucleotides in length, and are preferably less than about 100 and more preferably less than about 50, 25, 17 or 10 nucleotides in length.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the ohigonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their ability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate olignucleotides can be prepared by use of controlled pore glass polymer supports (Sarin et al., 1988, Proc. Natl. Acad. Sci. U.S.A. 85:7448–7451), etc.

While antisense nucleotides complementary to the FKHL7 coding region sequence can be used, those complementary to the transcribed untranslated region and to the region comprising the initiating methionine are most preferred.

The antisense molecules can be delivered to cells which express FKHL7 in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense sufficient to suppress translation on endogenous mRNAs in certain instances. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous FKHL7 transcripts and thereby prevent translation of the FKHL7 mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive and can include but not be limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al, 1982, Nature 296:39–42), etc. Any type of plasmid, cosmid, YAC or viral vector can be used to prepare the recombinant DNA construct which can be introduced directly into the tissue site. Alternatively, viral vectors can be used which selectively infect the desired tissue, in which case administration may be accomplished by another route (e.g., systematically).

Ribozyme molecules designed to catalytically cleave FKHL7 mRNA transcripts can also be used to prevent translation of FKHL7 mRNA and expression of FKHL7 (See, e.g., PCT International Publication WO90/11364, published Oct. 4, 1990; Sarver et al., 1990, Science 247:1222–1225 and U.S. Pat. No. 5,093,246). While ribozymes that cleave mRNA at site specific recognition sequences can be used to destroy FKHL7 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. There are a number of potential hammerhead ribozyme cleavage sites within the nucleotide sequence of human FKHL7 cDNA. Preferably the ribozyme is engineered so that the cleavage recognition site is located near the 5' end of the FKHL7 mRNA; i.e., to increase efficiency and minimize the intracellular accumulation of non-functional mRNA transcripts.

The ribozymes of the present invention can also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in an FKHL7 gene.

As in the antisense approach, the ribozymes can be composed of modified oligonucleotides (e.g., for improved stability, targeting, etc.) and should be delivered to cells which express the FKHL7 gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous FKHL7 messages and inhibit translation. Because ribozymes unlike antisense molecules, are catalytic, a lower intracellular concentration is required for efficiency.

Endogenous FKHL7 gene expression can also be reduced by inactivating or "knocking out" the FKHL7 gene or its promoter using targeted homologous recombination. (e.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional FKHL7 (or a completely unrelated DNA sequence) flanked by DNA homologous to the endogenous FKHL7 gene (either the coding regions or regulatory regions of the FKHL7 gene) can be used, with or without a selectable marker and/or a negative selectable marker, to transfect cells that express FKHL7 in vivo. Insertion of the DNA construct, via targeted homologous recombination, results in inactivation of the FKHL7 gene. Such approaches are particularly suited in the agricultural field where modifications to ES (embryonic stem) cells can be used to generate animal offspring with an inactive FKHL7 (e.g., see Thomas & Capecchi 1987 and Thompson 1989, supra). However this approach can be adapted for use in humans provided the recombinant DNA constructs are directly administered or targeted to the required site in vivo using appropriate viral vectors.

Alternatively, endogenous FKHL7 gene expression can be reduced by targeting deoxyribonucleotide sequences complementary to the regulatory region of the FKHL7 gene (i.e., the FKHL7 promoter and/or enhancers) to form triple helical structures that prevent transcription of the FKHL7 gene in target cells in the body. (See generally, Helene, C. 1991, Anticancer Drug Des., 6(6):569–84; Helene, C., et al., 1992, Ann. N.Y. Acad. Sci., 660:27–36; and Maher, L. J., 1992, Bioassays 14(12):807–15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

4.3.3. Vectors Encoding FKHL7 Proteins and FKHL7 Expressing Cells

The invention further provides plasmids and vectors encoding an FKHL7 protein, which can be used to express an FKHL7 protein in a host cell. The host cell may be any prokaryotic or eukaryotic cell. Thus, a nucleotide sequence derived from the cloning of mammalian FKHL7 proteins, encoding all or a selected portion of the full-length protein, can be used to produce a recombinant form of an FKHL7 polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial) cells, are standard procedures well known in the art.

Vectors that allow expression of a nucleic acid in a cell are referred to as expression vectors. Typically, expression vectors used for expressing an FKHL7 protein contain a nucleic acid encoding an FKHL7 polypeptide, operably linked to at least one transcriptional regulatory sequence. Regulatory sequences are art-recognized and are selected to direct expression of the subject FKHL7 proteins. Transcriptional regulatory sequences are described in Goeddel; Gene Expression Technology: Methods in Enzymology 185, Academic Press, San Diego, Calif. (1990). In one embodiment, the expression vector includes a recombinant gene encoding a peptide having an agonistic activity of a subject FKHL7 polypeptide, or alternatively, encoding a peptide which is an antagonistic form of an FKHL7 protein.

Suitable vectors for the expression of an FKHL7 polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in Experimental Manipulation of Gene Expression, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, an FKHL7 polypeptide is produced recombinantly utilizing an expression vector generated by sub-cloning the coding sequence of one of the FKHL7 genes represented in SEQ ID NOS. 1 or 3.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, $2^{nd}$ Ed., ed. by Sambrook, Fritsch and Maniatis (Cold Spring Harbor Laboratory Press: 1989) Chapters 16 and 17.

In some instances, it may be desirable to express the recombinant FKHL7 polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of an FKHL7 protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) J. Bacteriol. 169:751–757) and *Salmonella typhimurium* and its in vitro activity has been demonstrated on recombinant proteins (Miller et al. (1987) PNAS 84:2718–1722). Therefore, removal of an N-terminal methionine, if desired, can be achieved either in vivo by expressing FKHL7 derived polypeptides in a host which produces MAP (e.g., *E. coli* or CM89 or *S. cerevisiae*), or in vitro by use of purified MAP (e.g., procedure of Miller et al., supra).

Moreover, the gene constructs of the present invention can also be used as part of a gene therapy protocol to deliver nucleic acids encoding either an agonistic or antagonistic form of one of the subject FKHL7 proteins. Thus, another aspect of the invention features expression vectors for in vivo or in vitro transfection and expression of an FKHL7 polypeptide in particular cell types so as to reconstitute the function of, or alternatively, abrogate the function of FKHL7 in a tissue. This could be desirable, for example, when the naturally-occurring form of the protein is misexpressed or the natural protein is mutated and less active.

In addition to viral transfer methods, non-viral methods can also be employed to cause expression of a subject FKHL7 polypeptide in the tissue of an animal. Most non-viral methods of gene transfer rely on normal mechanisms used by mammalian cells for the uptake and intracellular transport of macromolecules. In preferred embodiments, non-viral targeting means of the present invention rely on endocytic pathways for the uptake of the subject FKHL7 polypeptide gene by the targeted cell. Exemplary targeting means of this type include liposomal derived systems, poly-lysine conjugates, and artificial viral envelopes.

In other embodiments, transgenic animals, described in more detail below could be used to produce recombinant proteins.

4.4. Polypeptides of the Present Invention

The present invention makes available FKHL7 polypeptides which are isolated from, or otherwise substantially free of other cellular proteins. The term "substantially free of other cellular proteins" (also referred to herein as "contaminating proteins") or "substantially pure or purified preparations" are defined as encompassing preparations of FKHL7 polypeptides having less than about 20% (by dry weight) contaminating protein, and preferably having less than about 5% contaminating protein. Functional forms of the subject polypeptides can be prepared, for the first time, as purified preparations by using a cloned gene as described herein.

Preferred FKHL7 proteins of the invention have an amino acid sequence which is at least about 60%, 65%, 66%, 67%, 68%, 69%, 70%, 71%, 72%, 73%, 74% 75%, 76%, 77%, 78%, 79%, 80%, 85%, 90%, or 95% identical or homologous to an amino acid sequence of SEQ ID NO. 2. Even more preferred FKHL7 proteins comprise an amino acid sequence which is at least about 97, 98, or 99% homologous or identical to an amino acid sequence of SEQ ID NO. 2. Such proteins can be recombinant proteins, and can be, e.g., produced in vitro from nucleic acids comprising a nucleotide sequence set forth in SEQ ID NOS. 1 or 3 or homologs thereof. For example, recombinant polypeptides preferred by the present invention can be encoded by a nucleic acid, which is at least about 85% homologous and more preferably at least about 90% homologous and most preferably at least about 95% homologous with a nucleotide sequence set forth in SEQ ID NOS. 1 or 3. Polypeptides which are encoded by a nucleic acid that is at least about 98–99% homologous with the sequence of SEQ ID NOS. 1 or 3 are also within the scope of the invention.

In a preferred embodiment, an FKHL7 protein of the present invention is a mammalian FKHL7 protein. In a particularly preferred embodiment an FKHL7 protein is set forth as SEQ ID NO. 2. In particularly preferred embodiments, an FKHL7 protein has an FKHL7 bioactivity. It will be understood that certain post-translational modifications, e.g., phosphorylation and the like, can increase the apparent molecular weight of the FKHL7 protein relative to the unmodified polypeptide chain.

The invention also features protein isoforms encoded by splice variants of the present invention. Such isoforms may have biological activities identical to or different from those possessed by the FKHL7 proteins specified by SEQ ID NO. 2.

FKHL7 polypeptides preferably are capable of functioning as either an agonist or antagonist of at least one biological activity of a wild-type ("authentic") FKHL7 protein of the appended sequence listing. The term "evolutionarily related to", with respect to amino acid sequences of FKHL7 proteins, refers to both polypeptides having amino acid sequences which have arisen naturally, and also to mutational variants of human FKHL7 polypeptides which are derived, for example, by combinatorial mutagenesis.

Full length proteins or fragments corresponding to one or more particular motifs and/or domains or to arbitrary sizes, for example, at least 5, 10, 25, 50, 75 and 100, amino acids in length are within the scope of the present invention.

For example, isolated FKHL7 polypeptides can be encoded by all or a portion of a nucleic acid sequence shown in any of SEQ ID NOS. 1 or 3. Isolated peptidyl portions of FKHL7 proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, an FKHL7 polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") FKHL7 protein.

Preferred FKHL7 polypeptides contain the forkhead domain located from about amino acid 73 to about 178 of SEQ ID NO. 2 (i.e. the underlined region of the protein shown in FIG. 1). Other preferred FKHL7 polypeptides bind to an RTAAAYA; SEQ ID NO:22 target region of a nucleic acid.

In general, polypeptides referred to herein as having an FKHL7 activity (e.g., are "bioactive") are defined as polypeptides which include an amino acid sequence encoded by all or a portion of the nucleic acid sequences shown in one of SEQ ID NOS. 1 or 3 and which mimic or antagonize all or a portion of the biological/biochemical activities of a naturally occurring FKHL7 protein. Examples of such biological activity include: regulation of gene expression. Furthermore these fragments can either promote or inhibit these processes or agonize or antagonize the activity of another agent which itself promotes or inhibits these processes. Other biological activities of the subject FKHL7 proteins will be reasonably apparent to one of skill in the art. According to the present invention, a polypeptide has biological activity if it is a specific agonist or antagonist of a naturally-occurring form of an FKHL7 protein. Assays for determining whether a compound, e.g, a protein, such as an FKHL7 protein or variant thereof, has one or more of the above biological activities are well known in the art.

Other preferred proteins of the invention are those encoded by the nucleic acids set forth in the section pertaining to nucleic acids of the invention. In particular, the invention provides fusion proteins, e.g., FKHL7-immunoglobulin fusion proteins. Such fusion proteins can provide, e.g., enhanced stability and solubility of FKHL7 proteins and may thus be useful in therapy. Fusion proteins can also be used to produce an immunogenic fragment of an FKHL7 protein. For example, the VP6 capsid protein of rotavirus can be used as an immunologic carrier protein for portions of the FKHL7 polypeptide, either in the monomeric form or in the form of a viral particle. The nucleic acid sequences corresponding to the portion of a subject FKHL7 protein to which antibodies are to be raised can be incorporated into a fusion gene construct which includes coding sequences for a late vaccinia virus structural protein to produce a set of recombinant viruses expressing fusion proteins comprising FKHL7 epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an FKHL7 protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple antigen peptide system for peptide-based immunization can also be utilized to generate an immunogen, wherein a desired portion of an FKHL7 polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of FKHL7 proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the FKHL7 polypeptides of the present invention. For example, FKHL7 polypeptides can be generated as glutathione-S-transferase (GST-fusion) proteins. Such GST-fusion proteins can enable easy purification of the FKHL7 polypeptide, as for example by the use of glutathione-derivatized matrices (see, for example, Current Protocols in Molecular Biology, eds. Ausubel et al. (N.Y.: John Wiley & Sons, 1991)).

The present invention further pertains to methods of producing the subject FKHL7 polypeptides. For example, a host cell transfected with a nucleic acid vector directing expression of a nucleotide sequence encoding the subject polypeptides can be cultured under appropriate conditions to allow expression of the peptide to occur. Suitable media for cell culture are well known in the art. The recombinant FKHL7 polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptides. In a preferred embodiment, the recombinant FKHL7 polypeptide is a fusion protein containing a domain which facilitates its purification, such as GST fusion protein.

Moreover, it will be generally appreciated that, under certain circumstances, it may be advantageous to provide homologs of one of the subject FKHL7 polypeptides, which function in a limited capacity as one of either an FKHL7 agonist (mimetic) or an FKHL7 antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of FKHL7 proteins.

Homologs of each of the subject FKHL7 proteins can be generated by mutagenesis, such as by discrete point mutation(s), or by truncation. For instance, mutation can give rise to homologs which retain substantially the same, or merely a subset, of the biological activity of the FKHL7 polypeptide from which it was derived. Alternatively, antagonistic forms of the protein can be generated which are able to inhibit the function of the naturally occurring form of the protein, such as by competitively binding to an FKHL7 receptor.

The recombinant FKHL7 polypeptides of the present invention also include homologs of the wildtype FKHL7 proteins, such as versions of those protein which are resistant to proteolytic cleavage, as for example, due to mutations which alter ubiquitination or other enzymatic targeting associated with the protein.

FKHL7 polypeptides may also be chemically modified to create FKHL7 derivatives by forming covalent or aggregate conjugates with other chemical moieties, such as glycosyl groups, lipids, phosphate, acetyl groups and the like. Covalent derivatives of FKHL7 proteins can be prepared by linking the chemical moieties to functional groups on amino acid sidechains of the protein or at the N-terminus or at the C-terminus of the polypeptide.

Modification of the structure of the subject FKHL7 polypeptides can be for such purposes as enhancing therapeutic or prophylactic efficacy, stability (e.g., ex vivo shelf life and resistance to proteolytic degradation), or post-translational modifications (e.g., to alter phosphorylation pattern of protein). Such modified peptides, when designed to retain at least one activity of the naturally-occurring form of the protein, or to produce specific antagonists thereof, are considered functional equivalents of the FKHL7 polypeptides described in more detail herein. Such modified peptides can be produced, for instance, by amino acid substitution, deletion, or addition. The substitutional variant may be a substituted conserved amino acid or a substituted non-conserved amino acid.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, $2^{nd}$ ed., Ed. by L. Stryer, WH Freeman and Co.: 1981). Whether a change in the amino acid sequence of a peptide results in a functional FKHL7 homolog (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject FKHL7 proteins as well as truncation mutants, and is especially useful for identifying potential variant sequences (e.g., homologs). The purpose of screening such combinatorial libraries is to generate, for example, novel FKHL7 homologs which can act as either agonists or antagonist, or alternatively, possess novel activities all together. Thus, combinatorially-derived homologs can be generated to have an increased potency relative to a naturally occurring form of the protein.

In one embodiment, the variegated library of FKHL7 variants is generated by combinatorial mutagenesis at the nucleic acid level, and is encoded by a variegated gene library. For instance, a mixture of synthetic oligonucleotides can be enzymatically ligated into gene sequences such that the degenerate set of potential FKHL7 sequences are expressible as individual polypeptides, or alternatively, as a set of larger fusion proteins (e.g., for phage display) containing the set of FKHL7 sequences therein.

There are many ways by which such libraries of potential FKHL7 homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential FKHL7 sequences. The synthesis of degenerate oligonucleotides is well known in the art (see for example, Narang, S A (1983) Tetrahedron 39:3; Itakura et al. (1981) Recombinant DNA, Proc $3^{rd}$ Cleveland Sympos. Macromolecules, ed. A G Walton, Amsterdam: Elsevier pp 273–289; Itakura et al.

(1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) PNAS 89:2429–2433; Devlin et al. (1990) Science 249: 404–406; Cwirla et al. (1990) PNAS 87: 6378–6382; as well as U.S. Pat. Nos. 5,223,409, 5,198,346, and 5,096,815).

Likewise, a library of coding sequence fragments can be provided for an FKHL7 clone in order to generate a variegated population of FKHL7 fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of an FKHL7 coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of FKHL7 homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate FKHL7 sequences created by combinatorial mutagenesis techniques. Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recursive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, PNAS USA 89:7811–7815; Yourvan et al., 1992, Parallel Problem Solving from Nature, 2., In Maenner and Manderick, eds., Elsevir Publishing Co., Amsterdam, pp. 401–410; Delgrave et al., 1993, Protein Engineering 6(3):327–331).

The invention also provides for reduction of the FKHL7 proteins to generate mimetics, e.g., peptide or non-peptide agents, such as small molecules, which are able to disrupt binding of an FKHL7 polypeptide of the present invention with a molecule, e.g. target peptide. Thus, such mutagenic techniques as described above are also useful to map the determinants of the FKHL7 proteins which participate in protein—protein interactions involved in, for example, binding of the subject FKHL7 polypeptide to a target peptide. To illustrate, the critical residues of a subject FKHL7 polypeptide which are involved in molecular recognition of its receptor can be determined and used to generate FKHL7 derived peptidomimetics or small molecules which competitively inhibit binding of the authentic FKHL7 protein with that moiety. By employing, for example, scanning mutagenesis to map the amino acid residues of the subject FKHL7 proteins which are involved in binding other proteins, peptidomimetic compounds can be generated which mimic those residues of the FKHL7 protein which facilitate the interaction. Such mimetics may then be used to interfere with the normal function of an FKHL7 protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffinan et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the $9^{th}$ American Peptide Symposium) Pierce Chemical Co. Rockland, Ill., 1985), b-turn dipeptide cores (Nagai et al. (1985) Tetrahedron Lett 26:647; and Sato et al. (1986) J Chem Soc Perkin Trans 1:1231), and β-aminoalcohols (Gordon et al. (1985) Biochem Biophys Res Commun 126:419; and Dann et al. (1986) Biochem Biophys Res Commun 134:71).

4.5. Anti-FKHL7 Antibodies and Uses Therefor

Another aspect of the invention pertains to an antibody specifically reactive with a mammalian FKHL7 protein, e.g., a wild-type or mutated FKHL7 protein. For example, by using immunogens derived from an FKHL7 protein, e.g., based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a mammalian FKHL7 polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of an FKHL7 protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of an FKHL7 protein of a mammal, e.g., antigenic determinants of a protein set forth in SEQ ID No: 2 or closely related homologs (e.g., at least 90% homologous, and more preferably at least 94% homologous).

Following immunization of an animal with an antigenic preparation of an FKHL7 polypeptide, anti-FKHL7 antisera can be obtained and, if desired, polyclonal anti-FKHL7 antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique originally developed by Kohler and Milstein ((1975) *Nature*, 256: 495–497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with a mammalian FKHL7 polypeptide of the present invention and monoclonal antibodies isolated from a culture comprising such hybridoma cells. In one embodiment anti-human FKHL7 antibodies specifically react with the protein encoded by a nucleic acid having SEQ ID NO. 1 or 3.

The term antibody as used herein is intended to include fragments thereof which are also specifically reactive with one of the subject mammalian FKHL7 polypeptides. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific, single-chain, and chimeric and humanized molecules having affinity for an FKHL7 protein conferred by at least one CDR region of the antibody. In preferred embodiments, the antibody further comprises a label attached thereto and able to be detected, (e.g., the label can be a radioisotope, fluorescent compound, enzyme or enzyme co-factor).

Anti-FKHL7 antibodies can be used, e.g., to monitor FKHL7 protein levels in an individual for determining, e.g., whether a subject has a disease or condition associated with an aberrant FKHL7 protein level, or allowing determination of the efficacy of a given treatment regimen for an individual afflicted with such a disorder. The level of FKHL7 polypeptides may be measured from cells in bodily fluid, such as in blood samples.

Another application of anti-FKHL7 antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of an FKHL7 protein, e.g., other orthologs of a particular FKHL7 protein or other paralogs from the same species, can then be detected with antibodies, as, for example, reacting nitrocellulose filters lifted from infected plates with anti-FKHL7 antibodies. Positive phage detected by this assay can then be isolated from the infected plate. Thus, the presence of FKHL7 homologs can be detected and cloned from other animals, as can alternate isoforms (including splice variants) from humans.

4.6. Transgenic Animals

The invention further provides for transgenic animals, which can be used for a variety of purposes, e.g., to identify FKHL7 therapeutics. Transgenic animals of the invention include non-human animals containing a heterologous FKHL7 gene or fragment thereof under the control of an FKHL7 promoter or under the control of a heterologous promoter. Accordingly, the transgenic animals of the invention can be animals expressing a transgene encoding a wild-type FKHL7 protein or fragment thereof or variants thereof, including mutants and polymorphic variants thereof Such animals can be used, e.g., to determine the effect of a difference in amino acid sequence of an FKHL7 protein from the sequence set forth in SEQ ID NO. 2, such as a polymorphic difference. These animals can also be used to determine the effect of expression of an FKHL7 protein in a specific site or for identifying FKHL7 therapeutics or confirming their activity in vivo.

The transgenic animals can also be animals containing a transgene, such as reporter gene, under the control of an FKHL7 promoter or fragment thereof. These animals are useful, e.g., for identifying compound that modulate production of FKHL7, such as by modulating FKHL7 gene expression. An FKHL7 gene promoter can be isolated, e.g., by screening of a genomic library with an FKHL7 cDNA fragment and characterized according to methods known in the art. In a preferred embodiment of the present invention, the transgenic animal containing said FKHL7 reporter gene is used to screen a class of bioactive molecules known as steroid hormones for their ability to modulate FKHL7 expression. In a more preferred embodiment of the invention, the steroid hormones screened for FKHL7 expression modulating activity belong to the group known as androgens. In a still more preferred embodiment of the invention, the steroid hormone is testosterone or a testosterone analog. Yet other non-human animals within the scope of the invention include those in which the expression of the endogenous FKHL7 gene has been mutated or "knocked out". A "knock out" animal is one carrying a homozygous or heterozygous deletion of a particular gene or genes. These animals could be useful to determine whether the absence of FKHL7 will result in a specific phenotype, in particular whether these mice have or are likely to develop a specific disease, such as high susceptibility to heart disease or cancer. Furthermore these animals are useful in screens for drugs which alleviate or attenuate the disease condition resulting from the mutation of the FKHL7 gene as outlined below. These animals are also useful for determining the effect of a specific amino acid difference, or allelic variation, in an FKHL7 gene. That is, the FKHL7 knock out animals can be crossed with transgenic animals expressing, e.g., a mutated form or allelic variant of FKHL7, thus resulting in an animal which expresses only the mutated protein and not the wild-type FKHL7 protein.

In a preferred embodiment of this aspect of the invention, a transgenic FKHL7 knock-out mouse, carrying the mutated FKHL7 locus on one or both of its chromosomes, is used as a model system for transgenic or drug treatment of the condition resulting from loss of FKHL7 expression.

Methods for obtaining transgenic and knockout non-human animals are well known in the art. Knock out mice are generated by homologous integration of a "knock out" construct into a mouse embryonic stem cell chromosome which encodes the gene to be knocked out. In one embodiment, gene targeting, which is a method of using homologous recombination to modify an animal's genome, can be used to introduce changes into cultured embryonic stem cells. By targeting a FKHL7 gene of interest in ES cells, these changes can be introduced into the germlines of animals to generate chimeras. The gene targeting procedure is accomplished by introducing into tissue culture cells a DNA targeting construct that includes a segment homologous to a target FKHL7 locus, and which also includes an intended sequence modification to the FKHL7 genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a FKHL7 gene function through the use of a targeting transgene construct designed to undergo homologous recombination with one or more FKHL7 genomic sequences. The targeting construct can be arranged so that, upon recombination with an element of a FKHL7 gene, a positive selection marker is inserted into (or replaces) coding sequences of the gene. The inserted sequence functionally disrupts the FKHL7 gene, while also providing a positive selection trait. Exemplary FKHL7 targeting constructs are described in more detail below.

Generally, the embryonic stem cells (ES cells) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) *J. Embryol. Exp. MoFKHL7hol.* 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934). Still another preferred ES cell line is the WW6 cell line (Ioffe et al. (1995) *PNAS* 92:7357–7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986]).

A knock out construct refers to a uniquely configured fragment of nucleic acid which is introduced into a stem cell line and allowed to recombine with the genome at the chromosomal locus of the gene of interest to be mutated. Thus a given knock out construct is specific for a given gene to be targeted for disruption. Nonetheless, many common elements exist among these constructs and these elements are well known in the art. A typical knock out construct contains nucleic acid fragments of not less than about 0.5 kb nor more than about 10.0 kb from both the 5' and the 3' ends of the genomic locus which encodes the gene to be mutated. These two fragments are separated by an intervening fragment of nucleic acid which encodes a positive selectable marker, such as the neomycin resistance gene ($neo^R$). The resulting nucleic acid fragment, consisting of a nucleic acid from the extreme 5' end of the genomic locus linked to a nucleic acid encoding a positive selectable marker which is in turn linked to a nucleic acid from the extreme 3' end of the genomic locus of interest, omits most of the coding sequence for FKHL7 or other gene of interest to be knocked out. When the resulting construct recombines homologously with the chromosome at this locus, it results in the loss of the omitted coding sequence, otherwise known as the structural gene, from the genomic locus. A stem cell in which such a rare homologous recombination event has taken place can be selected for by virtue of the stable integration into the genome of the nucleic acid of the gene encoding the positive selectable marker and subsequent selection for cells expressing this marker gene in the presence of an appropriate drug (neomycin in this example).

Variations on this basic technique also exist and are well known in the art. For example, a "knock-in" construct refers to the same basic arrangement of a nucleic acid encoding a 5' genomic locus fragment linked to nucleic acid encoding a positive selectable marker which in turn is linked to a nucleic acid encoding a 3' genomic locus fragment, but which differs in that none of the coding sequence is omitted and thus the 5' and the 3' genomic fragments used were initially contiguous before being disrupted by the introduction of the nucleic acid encoding the positive selectable marker gene. This "knock-in" type of construct is thus very useful for the construction of mutant transgenic animals when only a limited region of the genomic locus of the gene to be mutated, such as a single exon, is available for cloning and genetic manipulation. Alternatively, the "knock-in" construct can be used to specifically eliminate a single functional domain of the targeted gene, resulting in a transgenic animal which expresses a polypeptide of the targeted gene which is defective in one function, while retaining the function of other domains of the encoded polypeptide. This type of "knock-in" mutant frequently has the characteristic of a so-called "dominant negative" mutant because, especially in the case of proteins which homomultimerize, it can specifically block the action of (or "poison") the polypeptide product of the wild-type gene from which it was derived. In a variation of the knock-in technique, a marker gene is integrated at the genomic locus of interest such that expression of the marker gene comes under the control of the transcriptional regulatory elements of the targeted gene. A marker gene is one that encodes an enzyme whose activity can be detected (e.g., β-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

As mentioned above, the homologous recombination of the above described "knock out" and "knock in" constructs is very rare and frequently such a construct inserts nonhomologously into a random region of the genome where it has no effect on the gene which has been targeted for deletion, and where it can potentially recombine so as to disrupt another gene which was otherwise not intended to be altered. Such nonhomologous recombination events can be selected against by modifying the abovementioned knock out and knock in constructs so that they are flanked by negative selectable markers at either end (particularly through the use of two allelic variants of the thymidine kinase gene, the polypeptide product of which can be selected against in expressing cell lines in an appropriate tissue culture medium well known in the art—i.e. one containing a drug such as 5-bromodeoxyuridine). Thus a preferred embodiment of such a knock out or knock in construct of the invention consist of a nucleic acid encoding a negative selectable marker linked to a nucleic acid encoding a 5' end of a genomic locus linked to a nucleic acid of a positive selectable marker which in turn is linked to a nucleic acid encoding a 3' end of the same genomic locus which in turn is linked to a second nucleic acid encoding a negative selectable marker Nonhomologous recombination between the resulting knock out construct and the genome will usually result in the stable integration of one or both of these negative selectable marker genes and hence cells which have undergone nonhomologous recombination can be selected against by growth in the appropriate selective media (e.g. media containing a drug such as 5-bromodeoxyuridine for example). Simultaneous selection for the positive selectable marker and against the negative selectable marker will result in a vast enrichment for clones in which the knock out construct has recombined homologously at the locus of the gene intended to be mutated. The presence of the predicted chromosomal alteration at the targeted gene locus in the resulting knock out stem cell line can be confirmed by means of Southern blot analytical techniques which are well known to those familiar in the art. Alternatively, PCR can be used.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. For example, if the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knock out construct as explained above. Where more than one construct is to be introduced into the ES cell, each knockout construct can be introduced simultaneously or one at a time.

After suitable ES cells containing the knockout construct in the proper location have been identified by the selection techniques outlined above, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, the transformed ES cells can be microinjected into blastocytes. The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the FKHL7 gene knocked out in various tissues of the offspring by probing the Western blot with an antibody against the particular FKHL7 protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of an FKHL7-gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

A FKHL7 transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a FKHL7 protein can be essential for many forms of lineage analysis and can additionally provide a means to assess the effects of, for example, lack of FKHL7 expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques, which allow for the expression of transgenes can be regulated via site-specific genetic manipulation in vivo, are known to those skilled in the art. For instance, genetic systems are available which allow for the regulated expression of a recombinase that catalyzes the genetic recombination of a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject FKHL7 proteins. For example, excision of a target sequence which interferes with the expression of a recombinant FKHL7 gene, such as one which encodes an antagonistic homolog or an antisense transcript, can be designed to activate expression of that gene. This interference with expression of the protein can result from a variety of mechanisms, such as spatial separation of the FKHL7 gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant FKHL7 protein can be regulated via control of recombinase expression.

Use of the cre/loxP recombinase system to regulate expression of a recombinant FKHL7 protein requires the construction of a transgenic animal containing transgenes encoding both the Cre recombinase and the subject protein. Animals containing both the Cre recombinase and a recombinant FKHL7 gene can be provided through the construction of "double" transgenic animals. A convenient method for providing such animals is to mate two transgenic animals each containing a transgene, e.g., an FKHL7 gene and recombinase gene.

One advantage derived from initially constructing transgenic animals containing a FKHL7 transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic FKHL7 transgene is silent will allow the study of progeny from that founder in which disruption of FKHL7 mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the FKHL7 transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a FKHL7 transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H\text{-}2^b$, $H\text{-}2^d$ or $H\text{-}2^q$ haplotypes such as C57BL/6 or DBA/1. The line(s) used to practice this invention may themselves be transgenics, and/or may be knock-outs (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1–2pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a FKHL7 protein (either agonistic or antagonistic), and antisense transcript, or a FKHL7 mutant. Further, in such embodiments the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

4.7. Screening Assays for FKHL7 Therapeutics

The invention further provides screening methods for identifying FKHL7 therapeutics, e.g., for treating and/or preventing the development of a congenital heart disease.

An FKHL7 therapeutic can be any type of compound, including a protein, a peptide, peptidomimetic, small molecule, and nucleic acid. A nucleic acid can be, e.g., an FKHL7 gene, an antisense nucleic acid, a ribozyme, or a triplex molecule. An FKHL7 therapeutic of the invention can be an agonist or an antagonist. Preferred FKHL7 agonists include FKHL7 genes or proteins or derivatives thereof which mimic at least one FKHL7 activity. Other preferred agonists include compounds which are capable of increasing the production of an FKHL7 protein in a cell, e.g., compounds capable of upregulating the expression of an FKHL7 gene, and compounds which are capable of enhancing an FKHL7 activity and/or the interaction of an FKHL7 protein with another molecule, such as a target peptide. Preferred FKHL7 antagonists include FKHL7 proteins which are dominant negative proteins. Other preferred antagonists include compounds which decrease or inhibit the production of an FKHL7 protein in a cell and compounds which are capable of downregulating expression of an FKHL7 gene, and compounds which are capable of downregulating an FKHL7 activity and/or interaction of an FKHL7 protein with another molecule. In another preferred embodiment, an FKHL7 antagonist is a modified form of a target peptide, which is capable of binding to a gene, but which does not regulate expression of the gene.

The invention also provides screening methods for identifying FKHL7 agonist and antagonist compounds, comprising selecting compounds which are capable of interacting with an FKHL7 protein or with a molecule capable of interacting with an FKHL7 protein. In general, a molecule which is capable of interacting with an FKHL7 protein is referred to herein as "FKHL7 binding partner".

The compounds of the invention can be identified using various assays depending on the type of compound and activity of the compound that is desired. In addition, as described herein, the test compounds can be further tested in animal models. Set forth below are at least some assays that can be used for identifying FKHL7 therapeutics. However, based on the instant disclosure, one of skill in the art could use additional assays for identifying FKHL7 therapeutics without requiring undue experimentation.

4.7.1. Cell-free Assays

Cell-free assays can be used to identify compounds which are capable of interacting with an FKHL7 protein or binding partner, to thereby modify the activity of the FKHL7 protein or binding partner. Such a compound can, e.g., modify the structure of an FKHL7 protein or binding partner and thereby effect its activity. Cell-free assays can also be used to identify compounds which modulate the interaction between an FKHL7 protein and an FKHL7 binding partner, such as a target peptide. In a preferred embodiment, cell-free assays for identifying such compounds consist essentially in a reaction mixture containing an FKHL7 protein and a test compound or a library of test compounds in the presence or absence of a binding partner. A test compound can be, e.g., a derivative of an FKHL7 binding partner, e.g., a biologically inactive target peptide, or a small molecule.

Accordingly, one exemplary screening assay of the present invention includes the steps of contacting an FKHL7 protein or functional fragment thereof or an FKHL7 binding partner with a test compound or library of test compounds and detecting the formation of complexes. For detection purposes, the molecule can be labeled with a specific marker and the test compound or library of test compounds labeled with a different marker. Interaction of a test compound with an FKHL7 protein or fragment thereof or FKHL7 binding partner can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the FKHL7 protein, functional fragment thereof, FKHL7 analog or FKHL7 binding partner is then flown continuously over the sensor surface. A change in the resonance angle as shown on a signal recording, indicates that an interaction has occurred. This technique is further described, e.g., in BIAtechnology Handbook by Pharmacia.

Another exemplary screening assay of the present invention includes the steps of (a) forming a reaction mixture including: (i) an FKHL7 polypeptide, (ii) an FKHL7 binding partner, and (iii) a test compound; and (b) detecting interaction of the FKHL7 and the FKHL7 binding protein. The FKHL7 polypeptide and FKHL7 binding partner can be produced recombinantly, purified from a source, e.g., plasma, or chemically synthesized, as described herein. A statistically significant change (potentiation or inhibition) in the interaction of the FKHL7 and FKHL7 binding protein in the presence of the test compound, relative to the interaction in the absence of the test compound, indicates a potential agonist (mimetic or potentiator) or antagonist (inhibitor) of FKHL7 bioactivity for the test compound. The compounds of this assay can be contacted simultaneously. Alternatively, an FKHL7 protein can first be contacted with a test compound for an appropriate amount of time, following which the FKHL7 binding partner is added to the reaction mixture. The efficacy of the compound can be assessed by generating dose response curves from data obtained using various concentrations of the test compound. Moreover, a control assay can also be performed to provide a baseline for comparison. In the control assay, isolated and purified FKHL7 polypeptide or binding partner is added to a composition containing the FKHL7 binding partner or FKHL7 polypeptide, and the formation of a complex is quantitated in the absence of the test compound.

Complex formation between an FKHL7 protein and an FKHL7 binding partner may be detected by a variety of techniques. Modulation of the formation of complexes can be quantitated using, for example, detectably labeled proteins such as radiolabeled, fluorescently labeled, or enzymatically labeled FKHL7 proteins or FKHL7 binding partners, by immunoassay, or by chromatographic detection.

Typically, it will be desirable to immobilize either FKHL7 or its binding partner to facilitate separation of complexes from uncomplexed forms of one or both of the proteins, as well as to accommodate automation of the assay. Binding of FKHL7 to an FKHL7 binding partner, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/FKHL7 (GST/FKHL7) fusion proteins can be adsorbed onto glutathione sepharose beads (Sigma Chemical, St. Louis, Mo.) or glutathione derivatized microtitre plates, which are then combined with the FKHL7 binding partner, e.g., an $^{35}$S-labeled FKHL7 binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of FKHL7 protein or FKHL7 binding partner found in the bead fraction quantitated from the gel using standard electrophoretic techniques such as described in the appended examples.

Other techniques for immobilizing proteins on matrices are also available for use in the subject assay. For instance, either FKHL7 or its cognate binding partner can be immobilized utilizing conjugation of biotin and streptavidin. For instance, biotinylated FKHL7 molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with can be derivatized to the wells of the plate, and FKHL7 trapped in the wells by antibody conjugation. As above, preparations of an FKHL7 binding protein and a test compound are incubated in the FKHL7 presenting wells of the plate, and the amount of complex trapped in the well can be quantitated. Exemplary methods for detecting such complexes, in addition to those described above for the GST-immobilized complexes, include immunodetection of complexes using antibodies reactive with the FKHL7 binding partner, or which are reactive with FKHL7 protein and compete with the binding partner; as well as enzyme-linked assays which rely on detecting an enzymatic activity associated with the binding partner, either intrinsic or extrinsic activity. In the instance of the latter, the enzyme can be chemically conjugated or provided as a fusion protein with the FKHL7 binding partner. To illustrate, the FKHL7 binding partner can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as anti-FKHL7 antibodies, can be used. Alternatively, the protein to be detected in the complex can be "epitope tagged" in the form of a fusion protein which includes, in addition to the FKHL7 sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharmacia, NJ).

Cell-free assays can also be used to identify compounds which interact with an FKHL7 protein and modulate an activity of an FKHL7 protein. Accordingly, in one embodiment, an FKHL7 protein is contacted with a test compound and the catalytic activity of FKHL7 is monitored. In one embodiment, the ability of FKHL7 to bind a target molecule is determined. The binding affinity of FKHL7 to a target molecule can be determined according to methods known in the art. Determination of the enzymatic activity of FKHL7 can be performed with the aid of the substrate furanacryloyl-L-phenylalanyl-glycyl-glycine (FAPGG) under conditions described in Holmquist et al. (1979) Anal. Biochem. 95:540 and in U.S. Pat. No. 5,259,045.

4.7.2. Cell Based Assays

In addition to cell-free assays, such as described above, FKHL7 proteins as provided by the present invention, facilitate the generation of cell-based assays, e.g., for identifying small molecule agonists or antagonists. Cell based assays can be used, for example, to identify compounds which modulate expression of an FKHL7 gene, modulate translation of an FKHL7 mRNA, which modulate the stability of an FKHL7 mRNA or protein or which otherwise interfere with an interaction between an FKHL7 gene or protein and an FKHL7 binding partner. Accordingly, in one embodiment, a cell which is capable of producing FKHL7 is incubated with a test compound and the amount of FKHL7 produced in the cell medium is measured and compared to that produced from a cell which has not been contacted with the test compound. The specificity of the compound vis a vis FKHL7 can be confirmed by various control analysis, e.g., measuring the expression of one or more control genes. Compounds which can be tested include small molecules, proteins, and nucleic acids. In particular, this assay can be used to determine the efficacy of FKHL7 antisense molecules or ribozymes.

In another embodiment, the effect of a test compound on transcription of an FKHL7 gene is determined by transfection experiments using a reporter gene operatively linked to at least a portion of the promoter of an FKHL7 gene. A promoter region of a gene can be isolated, e.g., from a genomic library according to methods known in the art. The reporter gene can be any gene encoding a protein which is readily quantifiable, e.g, the luciferase or CAT gene. Such reporter gene are well known in the art.

This invention further pertains to novel agents identified by the above-described screening assays and uses thereof for treatments as described herein.

4.8. Predictive Medicine

The invention further features predictive medicines, which are based, at least in part, on the identity of the novel FKHL7 gene and alterations in the genes and related pathway genes, which affect the expression level and/or function of the encoded FKHL7 protein in a subject.

For example, as described herein, FKHL7 mutations that are particularly likely to cause or contribute to the development of a congenital heart disease are those mutations that negatively impact normal (wildtype) functioning of the forkhead domain that is involved with the DNA binding properties of FKHL7. Examples of such mutations include: i) upstream mutations that encode truncated transcripts that lack the DNA-binding, forkhead domain (e.g. an 11 base pair deletion encoding an FKHL7 transcript that is missing 477 amino acids); and ii) missense mutations occurring within the forkhead domain (e.g. a cytosine to thymine transition that causes an amino acid change at position 131 from serine to leucine (Ser131Leu); a cytosine to guanine transition that causes an amino acid change at position 126 from isoleucine to methionine (Ile126Met); and a thymine to cytosine transition, which results in a replacement of phenylalanine with serine at position 112 (Phe112Ser). In addition, mutations or translocations that result in expression of only one copy of FHKL7 (e.g. monosomy of 6p25), can result in a congenital heart disease phenotype.

Information obtained using the diagnostic assays described herein (alone or in conjunction with information on another genetic defect, which contributes to the same disease) is useful for prognosing, diagnosing or confirming that a subject has a genetic defect (e.g. in an FKHL7 gene or in a gene that regulates the expression of an FKHL7 gene), which causes or contributes to the development of glaucoma. Based on prognostic information, a doctor can recommend a regimen (e.g. diet or exercise) or therapeutic protocol, which is useful for preventing or prolonging onset of congenital heart disease in the individual.

In addition, knowledge of the particular alteration or alterations, resulting in defective or deficient FKHL7 genes or proteins in an individual (the FKHL7 genetic profile), alone or in conjunction with information on other genetic defects contributing to a congenital heart disease (the congenital heart disease genetic profile) allows customization of therapy to the individual's genetic profile, the goal of "pharmacogenomics". For example, an individual's FKHL7 genetic profile or the congenital heart disease genetic profile, can enable a doctor to: 1) more effectively prescribe a drug that will address the molecular basis of the glaucoma; and 2) better determine the appropriate dosage of a particular drug for the particular individual. For example, the expression level of FKHL7 proteins, alone or in conjunction with the expression level of other genes, known to contribute to the same disease, can be measured in many patients at various stages of the disease to generate a transcriptional or expression profile of the disease. Expression patterns of individual patients can then be compared to the expression profile of the disease to determine the appropriate drug and dose to administer to the patient.

The ability to target populations expected to show the highest clinical benefit, based on the FKHL7 or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since the use of FKHL7 as a marker is useful for optimizing effective dose).

These and other methods are described in further detail in the following sections.

4.8.1. Prognostic and Diagnostic Assays

The present methods provide means for determining if a subject has (diagnostic) or is at risk of developing (prognostic) a disease, condition or disorder that is associated with an aberrant FKHL7 activity, e.g., an aberrant level of FKHL7 protein or an aberrant bioactivity, such as results in the development of a congenital heart disease.

Accordingly, the invention provides methods for determining whether a subject has or is likely to develop a congenital heart disease, comprising determining the level of an FKHL7 gene or protein, an FKHL7 bioactivity and/or the presence of a mutation or particular polymorphic variant in the FKHL7 gene.

In one embodiment, the method comprises determining whether a subject has an abnormal mRNA and/or protein level of FKHL7, such as by Northern blot analysis, reverse transcription-polymerase chain reaction (RT-PCR), in situ hybridization, immunoprecipitation, Western blot hybridization, or immunohistochemistry. According to the method, cells are obtained from a subject and the FKHL7 protein or mRNA level is determined and compared to the level of FKHL7 protein or mRNA level in a healthy subject. An abnormal level of FKHL7 polypeptide or mRNA level is likely to be indicative of an aberrant FKHL7 activity.

In another embodiment, the method comprises measuring at least one activity of FKHL7. For example, regulation of the expression of a gene by an FKHL7 can be determined, e.g., as described herein. Comparison of the results obtained with results from similar analysis performed on FKHL7 proteins from healthy subjects is indicative of whether a subject has an abnormal FKHL7 activity.

In preferred embodiments, the methods for determining whether a subject has or is at risk for developing a disease, which is caused by or contributed to by an aberrant FKHL7 activity is characterized as comprising detecting, in a sample of cells from the subject, the presence or absence of a genetic alteration characterized by at least one of: (i) an alteration affecting the integrity of a gene encoding an FKHL7 polypeptide, or (ii) the mis-expression of the FKHL7 gene. For example, such genetic alterations can be detected by ascertaining the existence of at least one of: (i) a deletion of one or more nucleotides from an FKHL7 gene, (ii) an addition of one or more nucleotides to an FKHL7 gene, (iii) a substitution of one or more nucleotides of an FKHL7 gene, (iv) a gross chromosomal rearrangement of an FKHL7 gene, (v) a gross alteration in the level of a messenger RNA transcript of an FKHL7 gene, (vi) aberrant modification of an FKHL7 gene, such as of the methylation pattern of the genomic DNA, (vii) the presence of a non-wild type splicing pattern of a messenger RNA transcript of an FKHL7 gene, (viii) a non-wild type level of an FKHL7 polypeptide, (ix) allelic loss of an FKHL7 gene, and/or (x) inappropriate post-translational modification of an FKHL7 polypeptide. As set out below, the present invention provides a large number of assay techniques for detecting alterations in an FKHL7 gene. These methods include, but are not limited to, methods involving sequence analysis, Southern blot hybridization, restriction enzyme site mapping, and methods involving detection of the absence of nucleotide pairing between the nucleic acid to be analyzed and a probe. These and other methods are further described infra.

Specific diseases or disorders, e.g., genetic diseases or disorders, are associated with specific allelic variants of polymorphic regions of certain genes, which do not necessarily encode a mutated protein. Thus, the presence of a specific allelic variant of a polymorphic region of a gene, such as a single nucleotide polymorphism ("SNP"), in a subject can render the subject susceptible to developing a specific disease or disorder. Polymorphic regions in genes, e.g, FKHL7 genes, can be identified, by determining the nucleotide sequence of genes in populations of individuals. If a polymorphic region, e.g., SNP is identified, then the link with a specific disease can be determined by studying specific populations of individuals, e.g, individuals which developed a specific disease, such as glaucoma. A polymorphic region can be located in any region of a gene, e.g., exons, in coding or non coding regions of exons, introns, and promoter region.

It is likely that FKHL7 genes comprise polymorphic regions, specific alleles of which may be associated with specific diseases or conditions or with an increased likelihood of developing such diseases or conditions. Thus, the invention provides methods for determining the identity of the allele or allelic variant of a polymorphic region of an FKHL7 gene in a subject, to thereby determine whether the subject has or is at risk of developing a disease or disorder that is associated with a specific allelic variant of a polymorphic region.

In an exemplary embodiment, there is provided a nucleic acid composition comprising a nucleic acid probe including a region of nucleotide sequence which is capable of hybridizing to a sense or antisense sequence of an FKHL7 gene or naturally occurring mutants thereof, or 5' or 3' flanking sequences naturally associated with the subject FKHL7 genes or naturally occurring mutants thereof The nucleic acid of a cell is rendered accessible for hybridization, the probe is contacted with the nucleic acid of the sample, and the hybridization of the probe to the sample nucleic acid is detected. Such techniques can be used to detect alterations or allelic variants at either the genomic or mRNA level, including deletions, substitutions, etc., as well as to determine mRNA transcript levels.

A preferred detection method is allele specific hybridization using probes overlapping the mutation or polymorphic site and having about 5, 10, 20, 25, or 30 nucleotides around the mutation or polymorphic region. In a preferred embodiment of the invention, several probes capable of hybridizing specifically to allelic variants, such as single nucleotide polymorphisms, are attached to a solid phase support, e.g., a "chip". Oligonucleotides can be bound to a solid support by a variety of processes, including lithography. For example a chip can hold up to about 250,000 oligonucleotides. Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

In certain embodiments, detection of the alteration comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligase chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the FKHL7 gene (see Abravaya et al. (1995) *Nuc Acid Res* 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to an FKHL7 gene under conditions such that hybridization and amplification of the FKHL7 gene (if present) occurs, and (iv) detecting the presence or absence of an amplification product, or detecting the size of the amplification product and comparing the length to a control sample. It is anticipated that PCR, LCR or any other amplification procedure (e.g. self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), or Q-Beta Replicase (Lizardi, P. M. et al., 1988, Bio/Technology 6:1197)), may be used as a preliminary step to increase the amount of sample on which can be performed, any of the techniques for detecting mutations described herein.

In a preferred embodiment of the subject assay, mutations in, or allelic variants, of an FKHL7 gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the FKHL7 gene and detect mutations by comparing the sequence of the sample FKHL7 with the corresponding wild-type (control) sequence. Exemplary sequencing reactions include those based on techniques developed by Maxim and Gilbert (*Proc. Natl Acad Sci USA* (1977) 74:560) or Sanger (Sanger et al (1977) *Proc. Nat. Acad. Sci* 74:5463). It is also contemplated that any of a variety of automated sequencing procedures may be utilized when performing the subject assays (*Biotechniques* (1995) 19:448), including sequencing by mass spectrometry (see, for example PCT publication WO 94/16101; Cohen et al. (1996) *Adv Chromatogr* 36:127–162; and Griffin et al. (1993) *Appl Biochem Biotechnol* 38:147–159). It will be evident to one skilled in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers, et al. (1985) *Science* 230:1242). In general, the art technique of "mismatch cleavage" starts by providing heteroduplexes formed by hybridizing (labelled) RNA or DNA containing the wild-type FKHL7 sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl Acad Sci USA* 85:4397; Saleeba et al (1992) Methods Enzymol. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in FKHL7 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an FKHL7 sequence, e.g., a wild-type FKHL7 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations or the identity of the allelic variant of a polymorphic region in FKHL7 genes. For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) *Mutat Res* 285:125–144; and Hayashi (1992) *Genet Anal Tech Appl* 9:73–79). Single-stranded DNA fragments of sample and control FKHL7 nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of mutant or wild-type fragments in polyacrylamide gels containing a gradient of denaturant is assayed using denaturing gradient gel electrophoresis (DGGE) (Myers et al (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting point mutations or the identity of the allelic variant of a polymorphic region include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al. (1986) *Nature* 324:163); Saiki et al (1989) *Proc. Natl Acad. Sci USA* 86:6230). Such allele specific oligonucleotide hybridization techniques may be used to test one mutation or polymorphic region per reaction when oligonucleotides are hybridized to PCR amplified target DNA or a number of different mutations or polymorphic regions when, the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al (1989) *Nucleic Acids Res.* 17:2437–2448) or at the extreme 3' end of one primer where, under appropriate conditions, mismatch can prevent, or reduce polymerase extension (Prossner (1993) *Tibtech*

11:238. In addition it may be desirable to introduce a novel restriction site in the region of the mutation to create cleavage-based detection (Gasparini et al (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren, U. et al., Science 241:1077–1080 (1988). The OLA protocol uses two oligonucleotides which are designed to be capable of hybridizing to abutting sequences of a single strand of a target. One of the oligonucleotides is linked to a separation marker, e.g,. biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., Proc. Natl. Acad. Sci. (U.S.A.) 87:8923–8927 (1990). In this method, PCR is used to achieve the exponential amplification of target DNA, which is then detected using OLA.

Several techniques based on this OLA method have been developed and can be used to detect specific allelic variants of a polymorphic region of an FKHL7 gene. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) Nucleic Acids Res 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting single nucleotide polymorphisms in an FKHL7 gene. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent No. 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779–7784 (1989); Sokolov, B. P., Nucl. Acids Res. 18:3671 (1990); Syvanen, A. -C., et al., Genomics 8:684–692 (1990); Kuppuswamy, M. N. et al., Proc. Natl. Acad. Sci. (U.S.A.) 88:1143–1147 (1991); Prezant, T. R. et al., Hum. Mutat. 1:159–164 (1992); Ugozzoli, L. et al., GATA 9:107–112 (1992); Nyren, P. et al., Anal. Biochem. 208:171–175 (1993)). These methods differ from GBA TM in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A. -C., et al., Amer.J. Hum. Genet. 52:46–59 (1993)).

For mutations that produce premature termination of protein translation, the protein truncation test (PTT) offers an efficient diagnostic approach (Roest, et. al., (1993) *Hum. Mol. Genet.* 2:1719–21; van der Luijt, et. al., (1994) *Genomics* 20:1–4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

The methods described herein may be performed, for example, by utilizing pre-packaged diagnostic kits comprising at least one probe nucleic acid, primer set; and/or antibody reagent described herein, which may be conveniently used, e.g., in clinical settings to diagnose patients exhibiting symptoms or family history of a disease or illness involving an FKHL7 polypeptide.

Any cell type or tissue may be utilized in the diagnostics described below. In a preferred embodiment a bodily fluid, e.g., blood, is obtained from the subject to determine the presence of a mutation or the identity of the allelic variant of a polymorphic region of an FKHL7 gene. A bodily fluid, e.g, blood, can be obtained by known techniques (e.g. venipuncture). Alternatively, nucleic acid tests can be performed on dry samples (e.g. hair or skin). For prenatal diagnosis, fetal nucleic acid samples can be obtained from maternal blood as described in International Patent Application No. WO91/07660 to Bianchi. Alternatively, amniocytes or chorionic villi may be obtained for performing prenatal testing.

When using RNA or protein to determine the presence of a mutation or of a specific allelic variant of a polymorphic region of an FKHL7 gene, the cells or tissues that may be utilized must express the FKHL7 gene. Preferred cells for use in these methods include cardiac cells (see Examples). Alternative cells or tissues that can be used, can be identified by determining the expression pattern of the specific FKHL7 gene in a subject, such as by Northern blot analysis.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, N.Y.).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Antibodies directed against wild type or mutant FKHL7 polypeptides or allelic variants thereof, which are discussed above, may also be used in disease diagnostics and prognostics. Such diagnostic methods, may be used to detect abnormalities in the level of FKHL7 polypeptide expression, or abnormalities in the structure and/or tissue, cellular, or subcellular location of an FKHL7 polypeptide. Structural differences may include, for example, differences in the size, electronegativity, or antigenicity of the mutant FKHL7 polypeptide relative to the normal FKHL7 polypeptide. Protein from the tissue or cell type to be analyzed may easily be detected or isolated using techniques which are well known to one of skill in the art, including but not limited to western blot analysis. For a detailed explanation of methods for carrying out Western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of FKHL7 polypeptides. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the FKHL7 polypeptide, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an anti-FKHL7 polypeptide specific antibody is via linkage to an enzyme and use in an enzyme immunoassay (EIA) (Voller, "The Enzyme Linked Immunosorbent Assay (ELISA)", *Diagnostic Horizons* 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) *Enzyme Immunoassay*, CRC Press, Boca Raton, Fla., 1980; Ishikawa, et al., (eds.) *Enzyme Immunoassay*, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Moreover, it will be understood that any of the above methods for detecting alterations in a gene or gene product or polymorphic variants can be used to monitor the course of treatment or therapy.

4.8.2. Pharmacogenomics

Knowledge of the particular alteration or alterations, resulting in defective or deficient FKHL7 genes or proteins in an individual (the FKHL7 genetic profile), alone or in conjunction with information on other genetic defects contributing to the same disease (the genetic profile of the particular disease) allows a customization of the therapy for a particular disease to the individual's genetic profile, the goal of "pharmacogenomics". For example, subjects having a specific allele of an FKHL7 gene may or may not exhibit symptoms of a particular disease or be predisposed of developing symptoms of a particular disease. Further, if those subjects are symptomatic, they may or may not respond to a certain drug, e.g., a specific FKHL7 therapeutic, but may respond to another. Thus, generation of an FKHL7 genetic profile, (e.g., categorization of alterations in FKHL7 genes which are associated with the development of glaucoma), from a population of subjects, who are symptomatic for a disease or condition that is caused by or contributed to by a defective and/or deficient FKHL7 gene and/or protein (an FKHL7 genetic population profile) and comparison of an individual's FKHL7 profile to the population profile, permits the selection or design of drugs that are expected to be safe and efficacious for a particular patient or patient population (i.e., a group of patients having the same genetic alteration).

For example, an FKHL7 population profile can be performed, by determining the FKHL7 profile, e.g., the identity of FKHL7 genes, in a patient population having a disease, which is caused by or contributed to by a defective or deficient FKHL7 gene. Optionally, the FKHL7 population profile can further include information relating to the response of the population to an FKHL7 therapeutic, using any of a variety of methods, including, monitoring: 1) the severity of symptoms associated with the FKHL7 related disease, 2) FKHL7 gene expression level, 3) FKHL7 mRNA level, and/or 4) FKHL7 protein level. and (iii) dividing or categorizing the population based on the particular genetic alteration or alterations present in its FKHL7 gene or an FKHL7 pathway gene. The FKHL7 genetic population profile can also, optionally, indicate those particular alterations in which the patient was either responsive or non-responsive to a particular therapeutic. This information or population profile, is then useful for predicting which individuals should respond to particular drugs, based on their individual FKHL7 profile.

In a preferred embodiment, the FKHL7 profile is a transcriptional or expression level profile and step (i) is comprised of determining the expression level of FKHL7 proteins, alone or in conjunction with the expression level of other genes, known to contribute to the same disease. The FKHL7 profile can be measured in many patients at various stages of the disease.

Pharmacogenomic studies can also be performed using transgenic animals. For example, one can produce transgenic mice, e.g., as described herein, which contain a specific allelic variant of an FKHL7 gene. These mice can be created, e.g, by replacing their wild-type FKHL7 gene with an allele of the human FKHL7 gene. The response of these mice to specific FKHL7 therapeutics can then be determined.

4.8.3. Monitoring of Effects of FKHL7 Therapeutics During Clinical Trials

The ability to target populations expected to show the highest clinical benefit, based on the FKHL7 or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since the use of FKHL7 as a marker is useful for optimizing effective dose).

The treatment of an individual with an FKHL7 therapeutic can be monitored by determining FKHL7 characteristics, such as FKHL7 protein level or activity, FKHL7 mRNA level, and/or FKHL7 transcriptional level. This measurements will indicate whether the treatment is effective or whether it should be adjusted or optimized. Thus, FKHL7 can be used as a marker for the efficacy of a drug during clinical trials.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a preadministration sample from a subject prior to administration of the agent; (ii) detecting the level of expression of an FKHL7 protein, mRNA, or genomic DNA in the preadministration sample; (iii) obtaining one or more post-administration samples from the subject; (iv) detecting the level of expression or activity of the FKHL7 protein, mRNA, or genomic DNA in the post-administration samples; (v) comparing the level of expression or activity of the FKHL7 protein, mRNA, or genomic DNA in the preadministration sample with the FKHL7 protein, mRNA, or genomic DNA in the post administration sample or samples; and (vi) altering the administration of the agent to the subject accordingly. For example, increased administration of the agent may be desirable to increase the expression or activity of FKHL7 to higher levels than detected, i.e., to increase the effectiveness of the agent. Alternatively, decreased administration of the agent may be desirable to decrease expression or activity of FKHL7 to lower levels than detected, i.e., to decrease the effectiveness of the agent.

Cells of a subject may also be obtained before and after administration of an FKHL7 therapeutic to detect the level of expression of genes other than FKHL7, to verify that the FKHL7 therapeutic does not increase or decrease the expression of genes which could be deleterious. This can be done, e.g., by using the method of transcriptional profiling. Thus, mRNA from cells exposed in vivo to an FKHL7 therapeutic and mRNA from the same type of cells that were not exposed to the FKHL7 therapeutic could be reverse transcribed and hybridized to a chip containing DNA from numerous genes, to thereby compare the expression of genes in cells treated and not treated with an FKHL7-therapeutic. If, for example an FKHL7 therapeutic turns on the expression of a proto-oncogene in an individual, use of this particular FKHL7 therapeutic may be undesirable.

4.8.4 Kits

The invention further provides kits for use in diagnostics or prognostic methods for glaucoma or for determining which FKHL7 therapeutic should be administered to a subject, for example, by detecting the presence of FKHL7 mRNA or protein in a biological sample. For example, the kit can comprise a labeled compound or agent capable of detecting FKHL7 protein or mRNA in a biological sample; means for determining the amount of FKHL7 in the sample; and means for comparing the amount of FKHL7 in the sample with a standard. The compound or agent can be packaged in a suitable container. The kit can further comprise instructions for using the kit to detect FKHL7 mRNA or protein. Such a kit can comprise, e.g., one or more nucleic acid probes capable of hybridizing specifically to at least a portion of an FKHL7 gene or allelic variant thereof, or mutated form thereof.

4.9. Methods of Treatment

The present invention provides for both prophylactic and therapeutic methods of treating a subject having a congenital heart disease. Subjects at risk for such a disease can be identified by a diagnostic or prognostic assay, e.g., as described herein. Administration of a prophylactic agent can occur prior to the manifestation of symptoms characteristic of the FKHL7 aberrancy, such that development of the congenital heart disease is prevented or, alternatively, delayed in its progression. In general, the prophylactic or therapeutic methods comprise administering to the subject an effective amount of a compound which is capable of agonizing a wildtype FKHL7 activity or antagonizing a mutant (defective) FKHL7 activity. Examples of suitable compounds include the antagonists, agonists or homologues described in detail herein.

4.9.1. Effective Dose

Toxicity and therapeutic efficacy of such compounds can be determined by standard pharmaceutical procedures in cell cultures or experimental animals, e.g., for determining The $Ld_{50}$ (The Dose Lethal To 50% Of The Population) And The $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.9.2. Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insulation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remrnington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the e.g. heart or other organs without causing inflammation or ischemia. The administered therapeutic is slowly released from these microspheres and taken up by surrounding tissue cells (e.g. endothelial cells).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

In clinical settings, a gene delivery system for the therapeutic FKHL7 gene can be introduced into a patient by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) PNAS 91: 3054–3057). An FKHL7 gene, such as any one of the sequences represented in the group consisting of SEQ ID NOS 1 and 3 or a sequence homologous thereto can be delivered in a gene therapy construct by electroporation using techniques described, for example, by Dev et al. ((1994) Cancer Treat Rev 20:105–115).

The pharmaceutical preparation of the gene therapy construct or compound of the invention can consist essentially of the gene delivery system in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization(B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

5. EXAMPLES
5.1. Cloning and Analysis of Human FKHL7

Methods

Construction of Somatic Cell Hybrids. Lymphoblastoid cell lines (LCLs) were established whole blood from the two translocations patients. Somatic cell hybrids were created from the LCLs of patient with the balanced translocation using a modification of previously published protocols (Puck, J. M. et al., *J. Clin. Invest.* 79: 1395–1400 (1987); Nussbaum, R. L. et al., *Hum. Genet.* 64: 148–150 (1983)). Briefly, LCLs were expanded to roughly $2-5\times10^7$ cells in RPMI 1640 media with 10% inactivated fetal calf serum. The were pelleted at 1200 g in a table top centrifuge and resuspended in 2 m. of Dulbecco's Modified Eagles Medium with 10% uninactivated fetal calf serum (DMEM/UFCS). The plate was then incubated overnight in 4 ml of DMEM/UFCS.

The following day, the cells were trypsinized and split 1:5 into 100 mm plates. The cells grown in 5 ml of DMEM/UFC supplemented with $10^{-4}$M hypoxanthine and $4\times10^{-5}$M azaserine. This supplemented media was placed as needed until the colonies started to appear (2 to 4 weeks post-fusion). The individual colonies were allowed to grow until they were clearly visible without magnification. They were then removed from the plate using cloning rings to avoid contamination of the hybrid from others on the plate and put in 12-well tissue culture plates.

Marker typing. PCR amplification for the analysis of short tandem repeat polymorphism's (STRPs) was performed using 20 ng of genomic DNA in 5-pl reactions contain 0.5 $\mu$l of 10×PCR buffer [100 mM Tris-HCl (pH 8.8), 500 mM $MgCl_2$ 0.01% gelatin (w/v)], 200 $\mu$m each of dATP, dCTP, dGTP and dTTP, 2.5 pmol of each primer and 0.2 unit of Taq polymerase (BMB, ISC). Samples were subjected to 35 cycles of 94° C. as required) for 30 s and 72° C. for 30s. Amplification products were electrophoresed on 6% polyacrylamide gels contain 7.7 M urea at 60 W for approximately 2 h. The bands are detected by silver staining (Bassam, B. J., et al., *Anal. Biochem.* 196: 80–83 (1991)).

Marker typing for physical mapping performed on 2% agarose gels using a PCR reaction size 10 $\mu$l. Reaction conditions were as described above with the following exception. For markers which proved difficult to amplify using the standard Taq polymerase, we substituted an equal amount of AmpliTaq (ABI) along with an initial incubation of the PCR mixture at 94° C. for 10 m. For the amplification of the FKHL7 fragments, 10% DMSO was also added to the reaction mixture. For PCR reactions involving YAC, BAC or plasmid DNA, 1 to 2 ng of DNA was utilized as template. For colony PCR, a small number of cells were inoculated into 20 $\mu$l of dd$H_2$O. 1 $\mu$l of this suspension was used as template for the PCR reaction.

Oligonucleotide primers for the STRPs were obtained as MapPairs (Research Genetics). The custom primers required for this study were designed using the PRIMER 0.5 program and synthesized commercially (Research Genetics). Primer sequences for the screening assay and expected amplification sizes are available on request. Size standards for the 2% agarose gels were 100 bp ladder (Gibco/BRL) and for the denaturing acrylamide gels a 50 bp ladder (Gibco/BRL). For the 0.8% agarose gels, lambda DNA digested with StyT was used as a size marker.

YAC, BAC and cDNA Identification. Initial YACs were identified by searching a database at the Whitehead Institute/MIT Genome Center (http://www-genome.wi.mit.edu) (Hudson, T. J. et al., *Science* 270: 1945–1954 (1995) with STSs known to be in the 6p25 and 13q22 region. Subsequently, YACs and BACs were identified by a PCR-based screening assay of pooled libraries (Research Genetics) using various STSs within each region. A few of the chimeric YACs that were in critical areas were also obtained from a second source (Genome Systems). cDNA clones were identified by a BLASTN search of the public dbEST database available through a web interface (http://www.ncbi.nlm.nih.gov).

DNA Isolation. DNA was prepared from the somatic cell hybrid cell lines using a rapid salt isolation procedure (Laitinen, J. et al., Biotechniques 17: 316, 318, 320–322). The initial screening of the cell lines utilized a 500 ol volume of cells, while for the second stage of the DNA preparation the entire contents of a T75 flask was used. YAC DNA was isolated using the DNA-Pure yeast genomic kit (CPG Inc.). BAC DNA was prepared via an alkaline lysis protocol as implemented in the Wizard Plus Miniprep Kit (Promega) with the following modification to the protocol. Instead of loading the supernatant onto a vacuum column, it as precipitated with a 2× volume of absolute EtOH. In addition, 150 $\mu$l volumes were used for the commercial solutions in place of the 200 $\mu$l volumes suggested in the protocol. The precipitated DNA was then washed with 70% EtOH and dried. The DNA pellet was then resuspended in 50 $\mu$l of dd$H_2$O. Finally, plasmid DNA was prepared using a Wizard Plus Miniprep kit (Promega) following the recommended protocol. Culture sizes for DNA preparation from YACs, BACs and plasmnids were 1.5 ml of the appropriate media and antibiotics for each construct.

Subeloning of BACs. BAC DNA was digested with either EcoRI or HindIII for 8 h at 37° C. in a 50 $\mu$l reaction volume. Vector DNA (pUC19) was also digested with either EcoRI or HindIII under similar conditions. All restriction digests were purified by drop dialysis against dd$H_2$O using VS filters with a pore size of 0.025 $\mu$M (Millipore) for 15 minutes. Integrity of the digest was verified by gel electrophoresis of a portion of the reaction on 0.8% agarose gels. Equal amounts of digested BAC DNA and pUC19 vector were mixed and ligated overnight at 14° C. 1 to 3 $\mu$l of ligation mix was transformed into DH5α competent cells (Gibco/BRL). Recombinant clones were selected and the inserts were characterized by restriction enzyme digestion.

Sequencing plasmids and PCR products. PCR products for sequencing were amplified in a 50 $\mu$l reaction size and purified using the Quiaquick PCR Clean-up kit (Promega). 500 ng of plasmid DNA (in 4.5 $\mu$l) or 4.5 $\mu$l of purified PCR product was used as template for a sequencing reaction. 1 $\mu$l of primer (20 pmoles) and 4.5 $\mu$l of terminator sequencing mix (Amersham) was added for a final reaction size of 10 $\mu$l. Cycling conditions were performed as specified by the manufacturer. The sequencing reactions were precipitated in the presence of linear acrylamide and resuspended in 2 ol of loading buffer. The reactions were analyzed on an ABI 377 using a run time of 3 h.

Gene Identification and Characterization. Raw SCF files from ABI 373A and 377 sequences were imported directly into the Sequencher v3.0 program (GeneCodes). Contigs were generated by comparing all fragments in a project with the parameters of at least a 50 bp overlap in sequence with a 75% level of homology. Genomic sequence of both the 6p25 and 13q22 regions were submitted to the BLAST server at NCBI for a BLASTN analysis on both the NR and dbEST databases. Any region which gave a significant score ($p<10^{-5}$) was also submitted for a BLASTX screen of the SWISS-PROT database. EST sequence was obtained from GENBANK and SCF files from the WashU-Merck ftp site (ftp://genome.wusd.edu).

RNA Isolation and Blot Analysis. Freshly dissected embryos and adult tissues from NIH Swiss mice were rapidly frozen in liquid nitrogen and stored at −70° C. until use. Total cellular RNA was prepared using RNA STAT-60 (Tel-Test "B", Inc.) according to the manufacturer's specifications. Poly (A) mRNA was isolated using a Poly (A) Quick mRNA Isolation Kit (Stratagene). Two μg of poly (A) mRNA were electrophoresed through a 0.8% agarose gel containing formaldehyde. RNA length standards (0.4–9.5 kb) were obtained from Gibco-BRL. The gel was stained with ethidium bromide, destained overnight in 0.1 M ammonium acetate and the RNA was transferred to Gene Screen Plus (NEN) following the manufacturer's specifications.

Hybridization probes were gel-purified inserts of the following plasmids: human FKHL7 cDNA corresponding to the 3' UTR (I.M.A.G.E. Consortium Clone ID 864392, Research Genetics), murine Fkhl7 cDNA corresponding to the same region (I.M.A.G.E. Consortium Clone ID 864300, Research Genetics), the murine cDNA homologue of mannose dehydratase (I.M.A.G.E. Consortium Clone ID 717347, Research Genetics) and murine B-actin (Clontech). Hybridization probes were labeled with $^{32}$P-(dCTP) and hybridized for 16 h at 42° C. in 50% formamide, 5×SSC (SCC is a standard saline citrate: 0.15 M NaCl, 0.015 M Na citrate), 1×Denhardt's solution, 20 mM phosphate buffer (pH 7.6), 1% sodium dodecyl sulfate (SDS), 100 μg/ml salmon sperm DNA and 10% dextran sulfate. The filter was then washed twice at room temperature in 1×SSC followed by 2 rinses at 65° C. in 1×SSC—1% SDS and a final room temperature wash in 0.1×SSC. Kodak XAR-5 film was exposed at −70° C. with Dupont Cronex Lightning Plus intensifying screens (Dupont). Following autoradiography, the filter was stripped of radioactivity and subsequently rehybridized.

Mutation Detection and Confirmation. Mutation detection was performed using single strand conformation polymorphism (SSCP) analysis and direct sequencing of PCR products, PCR products were electrophoresed on SSCP gels (5 ml glycerol, 5 ml 5×TBE, 12.5 ml 37.5:1 acrylamide/bis and 77.5 ml ddH$_2$O) for 3 to 4 hr in 0.25×TBE at room temperature. Gels were silver stained as described above. Abnormal variants were sequenced and compared to a control sample to detect any changes from that of the normal sequence. Mutations were confirmed by amplification-refractory mutation system (ARMS) analysis (Newton, C. R. et al., *Nucleic Acids Res.* 17: 2503–2516 (1989).

RESULTS

Clinical features of translocation patients An infant female was delivered at 38 weeks gestation with an apparent de novo balanced translocation: 46,XX,t(6;13) (p25.3;q22.3). She was noted to have a number of congenital anomalies including a small mandible, cleft palate, hypoplastic lungs, segmental abnormalities of the cervical spine, and agenesis of the corpus callosum. Eye findings included nasolacrimal duct obstruction, persistent tunica vasculosa lentis, lower lid epiblepharon, ectropion, fistula to the nasolacrimal system, fat prolapse in the left eye and hypertelorism. She was diagnosed with PCG at the age of 6 months. Her parents and siblings are phenotypically normal and her parents have normal karyotypes.

Cytogenetic evaluation of a second infant female presenting with multiple congenital anomalies (cardiac defects, poor muscle tone, craniofacial abnormalities and hydronephrosis) revealed an unbalanced translocation: 46,XX,der(6)t(2;6)(q35;p25) with the loss of the region 6p25->pter and gain of 2q35->qter. At 5 days of age, she was found to have PCG based on diffuse corneal haze, presence of posterior embryotoxon, increased axial eye lengths, barely visible irides and elevated intraocular pressures.

Since the rearrangements in the above two patients appeared to occur in the same region of chromosome 6, we hypothesized that a gene causing PCG was present in this region, and that identification of the 6p25 breakpoint from the balanced translocation patient would allow for the identification of the gene responsible for PCG.

Mapping of the balanced translocation breakpoints. To facilitate the identification and cloning of the t(6;13) breakpoints, somatic cell hybrids were constructed from cell lines derived from the balanced translocation patient. Such hybrids are a useful tool in the mapping of chromosomal rearrangements as they allow for the molecular analysis of the derivative chromosomes apart from their normal homologues. Two somatic cell hybrids (H14 and H17) that each contained a single derivative chromosome were identified by genotyping with highly polymorphic markers. H17 was found to contain the derivative 13 chromosome and the normal human chromosome 6. H14 was found to contain the derivative 6 chromosome in the absence of the normal 6 and 13 chromosomes.

To map the t(6;13) breakpoints, DNA from hybrids H14 and H17 along with DNA from controls (CEPH individuals 1331-01 and 1331-02, the balanced translocation patient and the hamster cell line, RJK88) were used as PCR templates to screen genetic markers to identify those markers flanking the chromosome 6 and 13 breakpoints. Markers within the genetic map of 6p25 were selected for the screen. The 6p25 breakpoint was found to be located in a 5 cM region flanked by the markers D6S344 and D6S477. Similarly markers within the genetic map of 13q22 (Murray J. C. et al., (1994) *Science* 265: 2049–2054) were evaluated. The chromosome 13q22 breakpoint was found to be contained in a 3 cM region flanked by the markers D13S160 and D13S170.

A high resolution physical map of the 6p25 region was constructed to aid in the cloning of the 6p breakpoint. This map, along with the development of STSs from YACs, allowed mapping of the breakpoint to a small region near D6S344. BACs were then isolated from the region surrounding D6S344. Two BACs (185d15 and 471g19) were selected for subcloning based on their ability to cover the region as determined by STS content analysis. Primers derived from these BAC subclones were screened by PCR using hybrid H14 as template. This allowed identification of a clone that contained the 6p25 breakpoint. STS content mapping within the clone as compared to hybrid H14 allowed precise localization of the 6p25 breakpoint and obtainment of the surrounding sequence. The junction fragment from the H14 hybrid DNA was isolated using a primer flanking the 6p25 breakpoint in combination with a set of Alu-based primers (Dorin, J. R. et al., *Hum. Mol. Genet.* 1: 53–59 (1992)). Sequence analysis of this fragment confirmed that it was the junction fragment from hybrid H14. Since this junction fragment contained chromosome 13 sequence adjacent to the breakpoint, an STS was developed from this sequence and mapped onto the YAC/BAC contig of 13q22. This STS mapped distal to the 13q22 breakpoint and its location within the physical map of 13q22 was consistent with it being in close proximity to the breakpoint. This marker also mapped to the BAC 163n9 which had been isolated with markers that were proximal to the breakpoint. This result indicated that BAC 163n9 contained the 13q22 breakpoint of the balanced translocation patient.

Subclones from the 163n9 BAC were screened using the STS developed from the hybrid H14 junction fragment. A 3.5 kb subclone was identified that contained the 13q22 breakpoint. Sequence comparison with the normal chromosome 6 sequence and that from the hybrid H14 junction fragment revealed the location of the 13q22 breakpoint within the normal 13q22 sequence. Finally, the junction fragment from the hybrid H17 was evaluated to determine if there had been any gain or loss of material at the site of the translocation. Using hybrid H17 DNA, a single fragment was generated by PCR using a primer proximal to the 13q22 breakpoint and one distal to the 6p25 breakpoint. Sequence analysis confirmed that this fragment was the junction fragment from hybrid H17. Comparison of normal chromosome 6p25 sequence and normal chromosome 13q22 sequence along with that from the two junction fragments revealed that there had been a loss of 11 bp.

Identification of candidate genes within 6p25. Sequence generated from both sides of the 6p25 breakpoint (total of 10 kb) was analyzed for the presence of gene sequences by using both BLASTN (Alstchul, S. F. et al., *J. Mol. Biol.* 215:403–410 (1990) and BLASTX (Gish, W. et al., *Nat. Genet.* 3: 266–272 (1993)) to search public databases for homology to known genes. This sequence analysis resulted in the identification of a novel human gene showing strong homology to the GDP-Mannose 4,6-Dehydratase gene (E.C.4.2.1.47) that has been identified in a number of other organisms (Currie, H. L. et al., *Clin. Diagn. Lab. Immunol.* 2: 554–562 (1995); Li. Y et al., *Virology* 212: 134–150 (1995); Stevenson et al., *Bacteriol.* 178: 4885–4893 (1996); Bonin, C. P. et al. *Proc. Natl. Acad. Sci. USA* 94: 2085–2090 (1997)). By comparing the genomic sequence to the human cDNA sequence, the 6p25 breakpoint was localized to an intron upstream of the penultimate exon of this gene. Sequence analysis of BACs containing this gene has been used to determine the partial intron/exon boundaries for this gene. Human mannose dehydratase appears to be 1.1 kb in size and has at least 7 exons. The genornic structure of two areas of coding sequence (345 and 253 bp) remain to be determined.

Physical mapping of the 6p25 region indicated that a human forkhead transcription factor gene, FKHL7, is within 25 kb of the 6p25 breakpoint and is translocated to the derivative 13 chromosome. Sequence of the forkhead domain of FKHL7 has been published (Pierrou, S. et al., *EMBO J.* 13: 5002–5012 (1994)), along with FISH and somatic cell mapping data that confirm the localization of this gene to 6p25.

To determine if a gene on chromosome 13 could be considered a candidate gene for the glaucoma in the balanced translocation patient, 2 kb of DNA surrounding the 13q22 breakpoint was sequenced. GRAIL (Xu, Y. et al., *Gen. Engin.* 16: (241–253 (1994); and Uberbacher, E. C. and R. J. Mural *Proc. Natl. Acad Sci. USA* 88: 11261–11265 (1991))analysis of this sequence failed to find evidence for the presence of any predicted exons in close proximity to the breakpoint. BLAST (Alstchul, S. F. et al., *J. Mol. Biol.* 215:403–410 (1990), Gish, W. et al., *Nat. Genet.* 3: 266–272 (1993)) analysis also failed to identify any homologies to known genes or ESTs. The failure to detect a gene within the 13q22 region sequenced does not rule out the presence of a transcript as the possibility exists that the 13q22 breakpoint has occurred within a large intron.

Analysis of the t(2;6) unbalanced translocation patient. The patient with the t(2;6) unbalanced translocation is monosomic for a portion of distal 6p. In order to determine if this patient is monosomic for the t(6;13) breakpoint region of the balanced translocation patient, highly polymorphic genetic markers were amplified using genomic DNA from the unbalanced translocation patient as template. Markers proximal to D6S2652 were found to be heterozygous and markers distal to D6S2652 were found to be homozygous. This indicates that mannose dehydratase and FKHL7 which are distal to D6S2652 are present in only a single copy in the t(2;6) patient. Co-amplification of STSs in this region using quantitative PCR confirms the loss of chromosomal material containing mannose dehydratase and FKHL7 in this patient.

Expression studies of FKHL7 and mannose dehydratase. In order to prioritize FKHL7 and mannose dehydratase as candidates for congenital glaucoma, the expression pattern of each gene was evaluated by Northern blot analysis. Previous expression studies of FKHL7 demonstrated that a 3.9 kb transcript was widely expressed in a variety of human adult and fetal tissues, while the expression of a second 3.4 kb transcript was limited to fetal kidney (Pierrou, S et al., *EMBO J.* 13: 5002–5012 (1994)). Northern blot analysis of a variety of human adult tissues (brain, heart, kidney, spleen, liver and colon) confirmed the broad expression pattern of the 3.9 kb transcript and showed the co-expression of a 3.0 kb transcript. These multiple FKHL7 transcripts may arise by differential polyadenylation, consistent with the presence of several polyadenylation signals in the FKHL7 3'UTR. Using a murine orthologue of the FKHL7 3'UTR, expression was analyzed in staged mouse embryos and in various adult tissues including the eye. A 3.7 and 3.0 kb doublet was most abundantly expressed during embryogenesis, and of the adult tissues tested, expression in the eye and kidney were significantly higher than that seen in other adult tissues.

The expression pattern of mouse mannose dehydratase was also analyzed on the identical Northern blot used for the FKHL7 experiments. A basal level of expression was found during embryogenesis as well as in most adult tissues, including the eye. The transcript size of mouse mannose dehydratase appears to be approximately 1.9 kb in size which is in agreement with the size predicted from the human mannose dehydratase coding sequence.

Based on expression, both FKHL7 and mannose dehydratase are viable candidate genes for causing glaucoma phenotypes. However, based on the higher level of expression in the eye, the developmental regulation and putative function (Semina, E. V. et al., *Nat. Genet.* 14:392–399 (1966); Alward, W. L. M. et al., *Am. J. Ophthalmol.* 125:98–100 (1998); Glaser, T. et al., *Nat. Genet.* 2: 232–239 (1992); Jordan, T. et al., *Nat. Genet.* 1: 328–332 (1992) FKHL7 was favored as the better candidate.

Characterization of FKHL7 gene. FKHL7 is a monomeric DNA binding protein that shares a core binding site (RTAAAYA; SEQ ID NO: 22) with four other FKHL-like proteins (Pierrou, S. et al., *EMBO J.* 13: 5002–5012 (1994). The forkhead domain shows strong homology to the human gene, FKHL14, and the mouse genes Fkh1 and FKH14 by BLASTN (Altschul, S. F. et al., *J. Mol. Biol.* 215: 403–410 (1990) analysis. A 9.8 kb subclone of BAC 471g19 was partially sequenced and determined to contain the entire coding region of FKHL7 as well as 5 and 3' untranslated sequences. The human FKHL7 coding sequence is 1.7 kb in size (553 amino acids) and contains no introns. The 1659 bp open reading frame was found to contain the previously published DNA binding forkhead domain of FKHL7 (Pierrou, S. et al., *EMBO J.* 13: 5002–5012 (1994). The first in-frame ATG was found to match well to the Kozak consensus sequence (Kozak, M. *Annu. Rev. Cell. Biol.* 8: 197–225 (1992); Kozak, M. *Annu. Rev. Cell Biol.* 8: 197–225 (1992)). The COOH-terminal domain contains several stretches of homopolymeric runs of alanine and glycine. The FKHL7 coding region contains 5 recognition sites for the restriction enzyme NotI. The large number of NotI sites within the coding region of FKHL7 has adversely affected the identification of a full-length cDNA since many cDNA libraries are constructed with this restriction enzyme to prevent cloning at an internal site. A BLASTN (Altschul, S. F. et al., *J. Mol. Biol.* 215: 403–410 (1990) screen of the public dbEST database with the FKHL7 genomic sequence yields only partial human and mouse cDNA coverage of this gene. Based on the analysis of cDNA clones identified in the public databases, there is evidence for the utilization of at least two different polyadenylation signals within the 3' untranslated region.

Mutation screen. Although molecular analysis of the two translocation patients was extremely useful for identifying FKHL7 and mannose dehydratase as candidates for causing glaucoma, neither gene was conclusively demonstrated to be disease causing. Therefore, these two genes were screened for mutations in a cohort of unrelated probands with either PCG or anterior segment defects (RA and/or IH). Twenty-nine Caucasian probands were initially identified. Of these, 10 proved to have SSCP evidence of a mutation in another glaucoma related gene (either CYP1B1 or PITX2), and were therefore eliminated from the screen. The remaining 19 probands (6 PCG and 13 anterior chamber defect patients) were screened by SSCP for mutations in mannose dehydratase and FKHL7. No mannose dehydratase mutations were identified in a screen of 60% of the coding sequence of this gene. FKHL7 mutations were found in four probands and subsequently in related affected family members.

An 11 bp deletion upstream of the FKHL7 forkhead domain was identified in two brothers diagnosed with different anterior segment defects (RA and IH). Both brothers had glaucoma, and neither had the extra-ocular manifestations of Rieger syndrome (RS). Their father was found to have isolated posterior embryotoxon (PE), suggesting that the disease was inherited through him as an autosomal dominant. He was also found to carry the deletion. A second mutation was found in a proband and her mother who both were diagnosed with classic RA and glaucoma. This mutation, a C to T transition within the forkhead domain causes a change from a serine to a leucine (SER131Leu). A third mutation, a C to G transversion within the forkhead domain, was found in a proband with severe Axenfeld anomaly and glaucoma. This change results in the replacement of isoleucine with methionine (Ile126MET) and is also found in the father who was diagnosed with AA. Finally, a T to C transition was found in a proband of an extended family with a spectrum of anterior segment defects. This change results in the replacement of phenylalanine with serine (Phe112Ser) within the forkhead domain. Three of the mutations were not found in 128 unrelated normal individuals from an ethnically similar control population (Caucasian). The fourth mutation (Phe112Ser) was only detected by direct sequencing of PCR products from patient genomic DNA. This mutation was found to segregate with the disease in an extended pedigree and was not present in an additional 12 Caucasian individuals by sequence analysis.

The 11 bp deletion upstream of the FKHL7 forkhead domain is predicted to cause a truncated transcript (missing 477 aa) lacking the DNA-binding forkhead domain. All three missense mutations occur within highly conserved regions of the forkhead domain that has been implicated in the DNA binding properties of the molecule (Pierrou, S. et al., *EMBO J.* 13:5002–5012). The alteration of amino acids at these sites would be expected to have an effect on the DNA binding specificity of FKHL7. Finally, screening of FKHL7 in the translocation patients failed to identify mutations, suggesting that the presence of one abnormally expressed copy of the gene results in a disease phenotype.

We claim:

1. A method for determining whether a subject has or is at risk of developing a congenital heart disease, comprising measuring in the subject or in a sample obtained from the subject at least one FKHL7 activity, wherein a difference in the FKHL7 activity relative to the FKHL7 activity in a normal subject indicates that the subject has or is at risk of developing congenital heart disease.

2. The method of claim 1, wherein an FKHL7 activity is determined by measuring the protein level of an FKHL7 protein.

3. The method of claim 1, comprising determining whether an FKHL7 gene of the subject comprises a genetic alteration.

4. The method of claim 2, wherein FKHL7 protein levels are detected or quantified in an immunoassay using an antibody.

5. The method of claim 3, wherein determining whether a subject's FKHL7 gene comprises a genetic alteration further comprises the steps of:
   (a) contacting a nucleic acid comprising at least a portion of the FKHL7 gene from a subject with at least one nucleic acid probe which hybridizes with a wild-type FKHL7 gene; and
   (b) detecting the formation of a hybrid between the portion of the FKHL7 gene from the subject and at least one nucleic acid probe, wherein the absence of hybrid formation indicates that the subject's FKHL7 gene contains a genetic alteration.

6. The method of claim 3, wherein said genetic alteration is detected by: i) providing a probe or primer which hybridizes to a sense or antisense sequence of an FKHL7 gene or naturally occurring mutant thereof, or 5' or 3' flanking sequences naturally associated with the FKHL7 gene; (ii) contacting said probe or primer with an appropriate nucleic acid containing sample; and (iii) detecting, by hybridization of the probe or primer to the nucleic acid, the presence or absence of the genetic alteration.

7. The method of claim 3, wherein the FKHL7 genetic alteration is selected from the group consisting of (i) an upstream mutation that encodes a truncated transcript that lacks the DNA-binding, forkhead domain; (ii) a missense mutation occurring within the forkhead domain; and (iii) a mutation or translocation that results in expression of only one copy of FKHL7.

8. The method of claim 3, wherein said FKHL7 gene or FKHL7 genetic alteration is detected using a detection technique selected from the group consisting of Northern blot analysis, polymerase chain reaction (PCR), reverse transcriptase PCR (RT-PCR), anchor PCR, RACE PCR, ligase chain reaction (LCR), in situ hybridization, immunoprecipitation, Western blot analysis, immunohistochemistry, Genetic Bit Analysis, primer guided nucleotide incorporation, oligonucleotide ligation assay (OLA) and protein truncation test (PTT).

9. The method of claim 7, wherein said upstream mutation is an 11 base pair deletion encoding an FKHL7 transcript that is missing 477 amino acids.

10. The method of claim 7, wherein said missense mutation is selected from the group consisting of (i) a cytosine to thymine transition that causes an amino acid change at position 131 from serine to leucine (Ser131Leu); (ii) a cytosine to guanine transition that causes an amino acid change at position 126 from isoleucine to methionine (Ile126Met); and (iii) a thymine to cytosine transition, which results in a replacement of phenylalanine with serine at position 112 (Phe112Ser).

11. The method of claim 9, wherein said mutation or translocation that results in expression of only one copy of FKHL7 is monosomy of 6p25.

12. A method for establishing an FKHL7 genetic population profile in a population of individuals having a congenital heart disease, comprising determining an FKHL7 genetic profile of the individuals in the population and establishing a relationship between the FKHL7 genetic profiles and specific characteristics of the individuals.

13. The method of claim 12, wherein the specific characteristics of the individual include the individual's response to treatment.

14. A method for pharmacogenomically selecting a therapy to administer to an individual having a congenital heart disease, comprising determining an FKHL7 genetic profile of an individual and comparing the individual's FKHL7 genetic profile to an FKHL7 genetic population profile, to thereby select a therapy for administration to the individual.

15. The method of claim 14, wherein determining the FKHL7 genetic profile of an individual comprises determining the identity of a single nucleotide polymorphism.

16. A kit for determining whether a subject has or is likely to develop a congenital heart disease, comprising a probe or primer which hybrdizes to an FKHL7 nucleic acid and instructions for use.

17. The kit of claim 16, wherein the probe further includes a label group attached thereto, which is capable of being detected.

18. The kit of claim 16, wherein the probe or primer comprises at least about 12 consecutive nucleotides of sense or anti-sense sequence selected from the group consisting of SEQ ID NO:1, SEQ ID NO:3 and naturally occurring mutants thereof.

* * * * *